US009453923B2

(12) United States Patent
Eguchi

(10) Patent No.: US 9,453,923 B2
(45) Date of Patent: *Sep. 27, 2016

(54) PORTABLE RADIATION IMAGE CAPTURING APPARATUS AND RADIATION IMAGE CAPTURING SYSTEM

(71) Applicant: KONICA MINOLTA INC, Tokyo (JP)

(72) Inventor: Yoshihiko Eguchi, Tokorozawa (JP)

(73) Assignee: KONICA MINOLTA INC, Tokyo (JP)

( * ) Notice: Subject to any disclaimer, the term of this patent is extended or adjusted under 35 U.S.C. 154(b) by 153 days.

This patent is subject to a terminal disclaimer.

(21) Appl. No.: 14/197,785

(22) Filed: Mar. 5, 2014

(65) Prior Publication Data

US 2014/0183373 A1    Jul. 3, 2014

(30) Foreign Application Priority Data

Dec. 24, 2008  (JP) .................................. 2008-327069
Dec. 25, 2008  (JP) .................................. 2008-329758
Dec. 25, 2008  (JP) .................................. 2008-329800

(51) Int. Cl.
H05G 1/58    (2006.01)
G01T 1/175   (2006.01)
(Continued)

(52) U.S. Cl.
CPC ............. *G01T 1/175* (2013.01); *A61B 6/4233* (2013.01); *A61B 6/4283* (2013.01);
(Continued)

(58) Field of Classification Search
CPC .... G01N 23/04; G01N 23/08; G01N 23/083; A61B 6/4405; A61B 6/54; A61B 6/4233; A61B 6/46; A61B 6/465; H04N 5/335; G01T 1/2928; H05G 1/10; H05G 1/56

USPC .................... 378/62, 91, 98.8, 101, 114–116
See application file for complete search history.

(56) References Cited

U.S. PATENT DOCUMENTS

| 7,193,219 B2 | 3/2007 | Schick et al. |
| 8,705,700 B2 * | 4/2014 | Eguchi ................ A61B 6/4233 378/116 |
| 2007/0045552 A1 | 3/2007 | Masazumi |

FOREIGN PATENT DOCUMENTS

| JP | 06342099 A | 12/1994 |
| JP | 09073144 A | 3/1997 |

(Continued)

OTHER PUBLICATIONS

Japanese Notification of Reasons for Refusal corresponding to Patent Application No. 2014-002065; Dispatch Date: Nov. 25, 2014, with English translation.

(Continued)

*Primary Examiner* — Jurie Yun
(74) *Attorney, Agent, or Firm* — Cantor Colburn LLP

(57) ABSTRACT

A portable radiation image capturing apparatus is described. In the portable radiation image capturing apparatus multiple image capturing elements are two-dimensionally arranged, the apparatus is provided with a current detecting means for detecting a current flowing in the apparatus, a read-out circuit having a power supply mode in which the charge generated in each image capturing element can be read out and converted into an electric signal and a stand-by mode in which charge is not read out and power is consumed less than in the power supply mode, and a control means for causing the read-out circuit to change from the stand-by mode to the power supply mode when detecting start of irradiation with radiation on the basis of an increase in the current value detected by the current detecting means while the read-out circuit is in the stand-by mode.

3 Claims, 24 Drawing Sheets

(51) Int. Cl.
*A61B 6/00* (2006.01)
*G03B 42/04* (2006.01)
*H04N 5/32* (2006.01)
*H04N 5/369* (2011.01)

(52) U.S. Cl.
CPC .......... *A61B 6/4411* (2013.01); *A61B 6/4494* (2013.01); *A61B 6/566* (2013.01); *G03B 42/04* (2013.01); *H04N 5/32* (2013.01); *H04N 5/3698* (2013.01)

(56) References Cited

FOREIGN PATENT DOCUMENTS

| | | |
|---|---|---|
| JP | H11155847 A | 6/1999 |
| JP | 2000139889 A | 5/2000 |
| JP | 2000263339 A | 9/2000 |
| JP | 2000308630 A | 11/2000 |
| JP | 2002125960 A | 5/2002 |
| JP | 2002165142 A | 6/2002 |
| JP | 2003307569 A | 10/2003 |
| JP | 2004121385 A | 4/2004 |
| JP | 2005013536 A | 1/2005 |
| JP | 2005287937 A | 10/2005 |
| JP | 2006025828 A | 2/2006 |
| JP | 2006058124 A | 3/2006 |
| JP | 2006208301 A | 8/2006 |
| JP | 2007067622 A | 3/2007 |
| JP | 2008132216 A | 6/2008 |
| WO | 2006095538 A1 | 9/2006 |
| WO | 2006109551 A1 | 10/2006 |
| WO | 2008111355 A1 | 9/2008 |

OTHER PUBLICATIONS

International Search Report for PCT/JP2009/070449 dated Jan. 26, 2010.
Japanese Notification of Reasons for Refusal for Japanese Patent Application No. 2010-543994; Date of Mailing: Nov. 12, 2013, with English Translation.
Japanese Notification of Refusal corresponding to Application No. 2015-122565; Date of Mailing: May 10, 2016, with English translation.

\* cited by examiner

FIG. 10

| POWER CONSUMPTION MODE | | CONSUMED POWER [W] | OPERATION STATE OF EACH UNIT | | | | |
|---|---|---|---|---|---|---|---|
| MODE | STATE | | COMMUNICATION UNIT | IMAGE CAPTURING ELEMENT | TFT | S | IC |
| MODE1 | SLEEP | 1.6 | (ON) | — | — | OFF | OFF |
| MODE2 | WAITING FOR IRRADIATION | 5.2 | OFF(ON) | APPLIED | OPERATING | ON | OFF |
| MODE3 | ACCUMULATING | 8.8 | OFF(ON) | APPLIED | OPERATING | OFF | ON |
| MODE4 | READING | 13.6 | OFF(ON) | APPLIED | OPERATING | OFF | ON |

FIG.16

| IMAGE CAPTURING ORDER ID | PATIENT ID | PATIENT NAME | GENDER | AGE | DEPARTMENT | IMAGE CAPTURING PART | IMAGE CAPTURING DIRECTION | MODE OF IMAGE CAPTURING |
|---|---|---|---|---|---|---|---|---|
| 001 | 100085 | A | MALE | 25 | SURGERY | CHEST | SIDE L | SIMPLE |
| 002 | 100085 | A | MALE | 25 | SURGERY | CHEST | SIDE R | SIMPLE |
| 003 | 100085 | A | MALE | 25 | SURGERY | LEG | L | SIMPLE |
| 004 | 100085 | A | MALE | 25 | SURGERY | LEG | R | SIMPLE |
| 005 | 100125 | B | FEMALE | 55 | GENECOLOGY | BREAST | MLO-R | SIMPLE |
| 006 | 100125 | B | FEMALE | 55 | GENECOLOGY | BREAST | MLO-L | SIMPLE |
| 007 | 100125 | B | FEMALE | 55 | GENECOLOGY | BREAST | CC-L | SIMPLE |
| 008 | 100125 | B | FEMALE | 55 | GENECOLOGY | BREAST | CC-R | SIMPLE |
| 009 | 100320 | C | MALE | 15 | SURGERY | CHEST | FRONT | SUBTRACTION |
| 010 | 100325 | D | MALE | 60 | SURGERY | CHEST | FRONT | DYNAMIC IMAGE CAPTURING |

P1, P2, P3, P4, P5, P6, P7, P8, P9

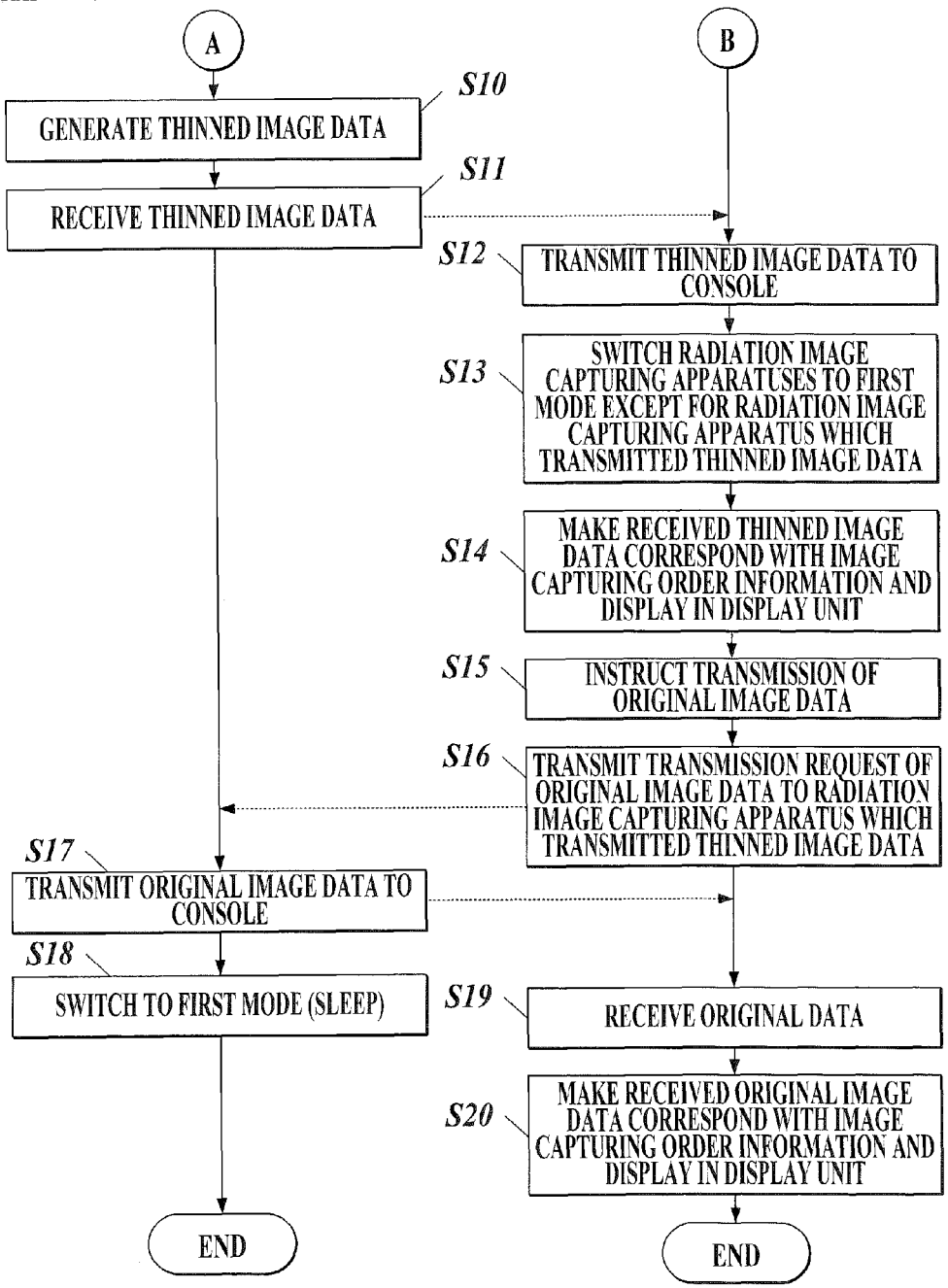

PLEASE INPUT IMAGE CAPTURING ORDER INFORMATION OF SCHEDULED IMAGE CAPTURING

| IMAGE CAPTURING ORDER ID | PATIENT ID | PATIENT NAME | GENDER | AGE | DEPARTMENT | IMAGE CAPTURING PART | IMAGE CAPTURING DIRECTION | MODE OF IMAGE CAPTURING |
|---|---|---|---|---|---|---|---|---|
| 001 | 100085 | A | MALE | 25 | SURGERY | CHEST | SIDE L | SIMPLE |
| 002 | 100085 | A | MALE | 25 | SURGERY | CHEST | SIDE R | SIMPLE |
| 003 | 100085 | A | MALE | 25 | SURGERY | LEG | L | SIMPLE |
| 004 | 100085 | A | MALE | 25 | SURGERY | LEG | R | SIMPLE |
| 005 | 100125 | B | FEMALE | 55 | GENECOLOGY | BREAST | MLO-R | SIMPLE |
| 006 | 100125 | B | FEMALE | 55 | GENECOLOGY | BREAST | MLO-L | SIMPLE |
| 007 | 100125 | B | FEMALE | 55 | GENECOLOGY | BREAST | CC-L | SIMPLE |
| 008 | 100125 | B | FEMALE | 55 | GENECOLOGY | BREAST | CC-R | SIMPLE |
| 009 | 100320 | C | MALE | 15 | SURGERY | CHEST | FRONT | SUBTRACTION |
| 010 | 100325 | D | MALE | 60 | SURGERY | CHEST | FRONT | DYNAMIC IMAGE CAPTURING |

P1　P2　P3　P4　P5　P6　P7　P8　P9

H1 h11 h12

RETURN  h14

PLEASE SELECT IMAGE CAPTURING ROOM TO CARRY OUT IMAGE CAPTURING

| IMAGE CAPTURING ROOM | RADIATION IMAGE CAPTURING APPARATUSES IN IMAGE CAPTURING ROOM (CASSETTE ID) | | | | |
|---|---|---|---|---|---|
| R1 | 1001 | 1002 | 1003 | 1004 | 1005 |
| R2 (IN USE) | 1006 | 1007 | — | — | — |
| R3 | 1008 | 1009 | 1010 | — | — |
| R4 | 1011 | 1012 | 1013 | 1014 | — |

RETURN  OK

PORTABLE RADIATION IMAGE CAPTURING APPARATUS AND RADIATION IMAGE CAPTURING SYSTEM

The present application is a divisional application of U.S. patent application Ser. No. 13/141,125, filed 21 Jun. 2011, the entire contents of which are incorporated herein by reference. Application Ser. No. 13/141,125 is the U.S. National Stage of Application No. PCT/JP2009/070449, filed on 7 Dec. 2009. Priority under 35 U.S.C. 119(a) and 35 U.S.C. 365(b) is claimed from Japanese Application Nos. 2008-327069, filed 24 Dec. 2008; 2008-329758, filed 25 Dec. 2008; and 2008-329800, filed 25 Dec. 2008 the disclosure of each of which are also incorporated herein by reference.

TECHNICAL FIELD

The present invention relates to a portable radiation image capturing apparatus and a radiation image capturing system.

BACKGROUND ART

Various types of so-called direct-type radiation image capturing apparatuses and so-called indirect-type radiation image capturing apparatuses are being developed. The direct-type radiation image capturing apparatus is a type that generates electric charge by a detection device according to the amount of radiation such as x-ray which is irradiated and converts the generated electric charge to electric signal. The indirect-type radiation image capturing apparatus is a type that converts the irradiated radiation to electromagnetic wave of other wave length such as visible light by a scintillator or the like, and thereafter, generates electric charge by a photoelectric conversion device such as a photodiode according to the energy of the electromagnetic wave which is converted and irradiated, and converts the generated electric charge to electric signal. Here, in the present invention, the detection device in the direct-type radiation image capturing apparatuses and the photoelectric conversion device in the indirect-type radiation image capturing apparatuses are called image capturing devices.

Such types of radiation image capturing apparatuses are known as FPD (Flat Panel Detector), and conventionally, they are integrally formed with a support platform (or a bucky) (for example, see Patent Document 1). However, in recent years, a portable radiation image capturing apparatus which is made to be portable by placing the image capturing device in a housing is developed and is being put to practical use (for example, see Patent Document 2 and 3). Normally, such portable radiation image capturing apparatus has a battery embedded therein.

As for the inner structure of the portable radiation image capturing apparatus, a plurality of image capturing elements 7 are two dimensionally arranged (matrix form) by each of the image capturing elements 7 being arranged in each of small regions which are marked off by a plurality of scanning lines 5 and a plurality of signal lines 6 which are arranged on the substrate 4 so as to cross over each other, as shown in the after-mentioned FIG. 7. Further, each of the image capturing elements 7 is connected to a bias line 9 and each of the image capturing elements 7 is made to be conductive by reverse bias voltage being applied from the reverse bias power source 14 via the bias lines 9. Thereby, each of the image capturing elements 7 is made to be in an image capturing state.

Moreover, in the radiation image capturing, when radiation is irradiated to the radiation image capturing apparatus, electric charge is generated in the image capturing elements 7 according to the amount of radiation which is irradiated and the electric charge of each of the image capturing elements 7 is read by the reading circuits 17, and then, each of the read electric charge is amplified by the charging/voltage conversion or the like to be taken out as an electric signal.

However, when each of the image capturing elements 7, the reading circuits 17 and the like are made to be conductive for the radiation image capturing, relatively large amount of power is to be consumed when considering the radiation image capturing apparatus as a whole. In the above mentioned radiation image capturing apparatus which is integrally formed with the support platform or the bucky, the situation where the radiation image capturing cannot be carried out will not occur even when a relatively large amount of power is being consumed because power is supplied constantly via the support platform or the bucky. However, in the battery embedded type portable radiation image capturing apparatus, the battery will die when a large amount of power is consumed and there will be problems that radiation image capturing cannot be carried out consecutively, that the battery needs to be charged frequently and the like.

In view of the above problems, in Patent Document 4, there is suggested an example of a radiation image capturing apparatus which is integrally formed with a support platform and the bucky. However, this example of a radiation image capturing apparatus is an image capturing apparatus which is structured by having separate power supply units for supplying power to each of the sensor region in which the image capturing elements 7 are provided and to the reading circuits 17 and the like, the radiation image capturing apparatus supplies power to the image capturing elements 7 and the like in the sensor region first, and then, supplies power to the reading circuits 17 and the like.

PRIOR ART DOCUMENTS

Patent documents

Patent Document 1: JP H9-73144
Patent Document 2: JP H6-342099
Patent Document 3: JP 2006-58124
Patent Document 4: JP 2002-165142
Patent Document 5: JP 2002-125960
Patent Document 6: JP 2000-263339
Patent Document 7: JP 2000-139889
Patent Document 8: JP 2000-308630

SUMMARY OF THE INVENTION

Problem to be Solved by the Invention

However, in the image capturing apparatus described in Patent Document 4, great amount of power is consumed, after all, when the image capturing apparatus is seen as a whole when it takes a long time until radiation is actually irradiated to the image capturing apparatus after supplying power to the image capturing elements 7 in the sensor region and after supplying power to the reading circuits 17 and the like.

In order to avoid the above problem, Patent Document 4 describes that power is supplied to the image capturing elements 7 in the sensor region based on a signal for activating such as the radiation source of the radiation generation device which emits radiation to the radiation image capturing apparatus and power is supplied to such as the reading circuits 17 when the irradiation of radiation is requested to the radiation generation device and when the irradiation of radiation is completed.

However, in such structure, there is a need to control so as to have an interface between the radiation generation device and the radiation image capturing apparatus. However, in many cases, the radiation generation device and the radiation image capturing apparatus are manufactured by different manufacturers, and there are problems such that the control structure cannot be established easily and the like.

In view of the above problems, the present invention is achieved and its object is to provide a portable radiation image capturing apparatus in which the irradiation of ration can be detected without having an interface between the radiation generation device and in which power consumption can be reduced when capturing a radiation image.

On the other hand, such portable radiation image capturing apparatus is normally structured so as to be used by being loaded in the cassette holing unit of the bucky. In recent years, there are many cases where a radiation image is captured by irradiation radiation from a portable radiation generation device by placing such as a hand of a patient which is the target on the radiation incidence surface of the radiation image capturing apparatus, for example, by using the radiation image capturing apparatus in a state not being loaded in the bucky, that is, using the radiation image capturing apparatus by itself taking advantage of the portability of the radiation image capturing apparatus.

Further, there is developed a portable radiation image capturing apparatus which carries out sending and receiving of image data and the like between an external apparatus such as a console via a wireless communication unit such as an antenna device (for example, see Patent Document 5). In such portable radiation image capturing apparatus which includes the wireless communication unit, power is to be supplied from the power source housed in a case, and a chargeable battery can be housed (for example, see Patent Document 6).

When the above described portable radiation image capturing apparatus which can carry out wireless communication with a console is used, the radiation image capturing apparatus can be disposed in the image capturing room in advance and the radiation image capturing apparatus which was used for image capturing can be left in the image capturing room after the image capturing. Therefore, there is no need for an operator to carry the radiation image capturing apparatus into the image capturing room for every image capturing. Thus, operation load of an operator is small and it is convenient.

Especially, in the portable radiation image capturing apparatus in which a battery is embedded, there are many cases where it is structured so as to switch the supplying state of power to the radiation detection elements and the like between a image capturable mode in which the radiation image capturing can be carried out by supplying power to the radiation detection elements and the like and a sleep mode in which power supply to the radiation detection elements and the like is stopped and power is supplied only to the needed parts. Then, the radiation image capturing apparatus in the image capturing room is disposed in a state being switched to the sleep mode and the radiation image capturing apparatus is switched to the image capturable mode from the sleep mode at the time of image capturing to capture an image. Normally, it takes time for the radiation image capturing apparatus to actually be in the image capturable state after carrying out the control to activate the radiation image capturing apparatus in the sleep mode.

In view of the above, there is known a radiation image capturing apparatus in which the radiation image capturing can be started promptly when actually carrying out the image capturing by putting the radiation image capturing apparatus which is disposed in the image capturing room in an activation state at once at the timing when an operator inputs selections of image capturing order information, image capturing condition for the image capturing parts and the like and information necessary for image processing by a console or the like (for example, see Patent Document 7).

However, in a system where the radiation image capturing apparatus is controlled to be in a driven state at the timing when information needed to the image capturing is input as in the radiation image capturing apparatus disclosed in Patent Document 7, the timing of starting and ending of radiation irradiation need to be informed to the radiation image capturing apparatus from the console after the radiation image capturing apparatus is in the state capable of image capturing. Therefore, a control unit for sending and receiving signals for notifying the timings of starting and ending of radiation irradiation between the console and the radiation generation device and between the console and the radiation image capturing apparatus is needed, and there is a problem that the control configuration be complicated.

Further, after moving to the driven state, when the time period until the radiation is to be irradiated is long, consumption of driving power be a great amount, especially, in a case of a portable radiation image capturing apparatus in which a battery is embedded, there is a possibility that electricity for radiation image capturing, image transmission and the like run short.

Moreover, when the above system is applied to a system where a plurality of radiation image capturing apparatuses are disposed in an image capturing room and configured so that all of the radiation image capturing apparatuses in the image capturing room are to be in a state capable of image capturing in advance before the image capturing, not only that regular image data are transmitted to the console from the radiation image capturing apparatus used for the image capturing by the transmission instruction from the console, but also, so-called ghost images are transmitted from the radiation image capturing apparatuses not used for image capturing. Thereby, unnecessary power consumption occurs. Further, an operation of making a regular image and image capturing order information correspond with each other need to be carried out in the console, and there is a possibility that the regular image and the image capturing order information may not be corresponded with each other correctly.

In view of the above, there is developed a radiation image capturing system in which a switch for selecting the radiation image capturing apparatus as the radiation image capturing apparatus to be used for image capturing is provided to each of the plurality of radiation image capturing apparatuses disposed in the image capturing room and in which the radiation image capturing apparatuses are controlled so that only the radiation image capturing apparatus which is selected by the switch is switched to the image capturing capable mode and the radiation image capturing apparatuses which are not selected are to be in sleep mode (for example, see Patent Document 8). In such system, it is configured that a lamp or the like of the radiation image capturing apparatus which is made to be in the image capturing capable mode by the selecting of an operator lights up, and the radiation image capturing apparatus which is in the image capturing capable mode and the radiation image capturing apparatuses in the sleep mode can be discriminated by looking at the lamp.

When it is configured so as to make only one radiation image capturing apparatus be in the image capturing capable mode for one image capturing as in the radiation image capturing system disclosed in the above Patent Document 8, needles power consumption of the radiation image capturing apparatuses not used for the image capturing can be prevented and ghost images can be prohibited from being transmitted to the console.

However, in the system where only the radiation image capturing apparatus to be used for image capturing is made to be in the image capturing capable mode in advance and executing the image capturing by using the radiation image capturing apparatus which is made to be in the image capturing capable mode as in the radiation image capturing system disclosed in Patent Document 8 or in a system in which the radiation image capturing system disclosed in Patent Document 7 is applied to a system in which a plurality of radiation image capturing apparatuses are disposed in an image capturing room and all of the radiation image capturing apparatuses in the image capturing room are made to be in the image capturing capable mode in advance, there is a possibility that the following problems may occur.

For example, when it is configured so that an operator selects the radiation image capturing apparatus to be used for image capturing and makes the apparatus be in the image capturing capable mode in advance and the selected radiation image capturing apparatus can be determined among a plurality of radiation image capturing apparatuses by looking at a display device such as a lamp indicating the power supply state, there is a possibility that an operator forgets to confirm the display device indicating the power supply state and mistakenly executes image capturing by using a radiation image capturing apparatus which is not selected. Further, when a radiation image capturing apparatus is housed in the bucky of standing position type and recumbent position type, there is a possibility that the display device is difficult to be confirmed from outside or cannot be confirmed from outside. In such case, the possibility of mistakenly using wrong radiation image capturing apparatus is even greater.

Moreover, when it is configured that once the radiation image capturing apparatus to be used is selected, the state of the radiation image capturing apparatus being selected continues until another radiation image capturing apparatus is selected, the selected radiation image capturing apparatus is difficult to be recognized especially when there is a long time period until next image capturing, when the operator changes or the like.

Furthermore, when an operator identifies the radiation image capturing apparatus by a cassette ID which is assigned uniquely to each radiation image capturing apparatus, there is a possibility that the cassette ID recognized by an operator and the actual cassette ID do not match each other and the wring radiation image capturing apparatus is to be used. For example, when there are two radiation image capturing apparatuses which are a radiation image capturing apparatus having cassette ID of "1004" and a radiation image capturing apparatus having cassette ID of "1005" being disposed in the image capturing room, an operator may mistakenly use the radiation image capturing apparatus having cassette ID on "1005" thinking that he/she is using the radiation image capturing apparatus having cassette ID of "1004" and further, he/she may not be able to even recognize that the radiation image capturing apparatus which he/she used is the radiation image capturing apparatus having cassette ID of "1005".

In such way, when a plurality of radiation image capturing apparatuses are disposed in an image capturing room, there is a possibility that an operator may mistake the radiation image capturing apparatus which is not to be used for the image capturing for the radiation image capturing apparatus to be used for the image capturing and mistakenly execute the image capturing by using the radiation image capturing apparatus which is not to be used for the image capturing in the conventional system. Further, in the conventional system, an operator needs to identify the radiation image capturing apparatus to be used for the image capturing among a plurality of radiation image capturing apparatus, and therefore, this is an operational strain and a psychological burden for an operator.

When an operator mistakes the radiation image capturing apparatus which is not to be used to the image capturing for the radiation image capturing apparatus to be used for the image capturing and executes the image capturing, there is a possibility that the following problems may occur in addition.

First, when the cassette ID recognized by an operator and the actual cassette ID do not match and an image capturing is mistakenly executed by using a radiation image capturing apparatus which is in sleep mode in the system where only the radiation image capturing apparatus to be used for the image capturing is made to be in the image capturing capable mode and the image capturing is to be executed by using the radiation image capturing apparatus which is made to be in the image capturing capable mode, image data itself cannot be obtained even when radiation is irradiated to the radiation image capturing apparatus and image capturing needs to be executed again. Thereby, unnecessary electricity is consumed. Further, whether image capturing needs to be carried out again or not is determined after confirming the image in the console, and therefore, the patient needs to wait for long time and a great strain is put on to the operator and the patient.

Moreover, when an image capturing is executed by using the radiation image capturing apparatus having cassette ID which is different from the cassette ID recognized by an operator in the system where all of the radiation image capturing apparatuses in the image capturing room are made to be in the image capturing capable mode in advance, there is a possibility that an operator may request a transmission of an image to the radiation image capturing apparatus which is actually not used for the image capturing due to the cassette ID recognized by him/her not matching to the actual cassette ID after the image capturing.

That is, a case where an operator requests an image transmission to the radiation image capturing apparatus having cassette ID of "1004" which is not actually used for the image capturing when an operator mistakenly uses the radiation image capturing apparatus having cassette ID of "1005" thinking that he/she is using the radiation image capturing apparatus having cassette ID of "1004" as described above.

In such case, not only that the correct image data cannot be obtained from the radiation image capturing apparatus (the radiation image capturing apparatus having cassette ID of "1005") which is actually used for the image capturing in the console after the image capturing, but also, there is a possibility that image data of different patient may be transmitted from the radiation image capturing apparatus (the radiation image capturing apparatus having cassette ID of "1004") which is not actually used for the image capturing.

At this time, when an operator does not recognize that the image data is data of a different patient from the radiation image capturing apparatus which is not used for the image capturing by looking at the image, there is a possibility that a serious medical mistake such as confusion of image data may occur.

Moreover, even when image data of a different patient is not to be transmitted from the radiation image capturing apparatus which is not used for the image capturing, the radiation image capturing apparatus used for the image capturing needs to be searched to obtain correct image data from the radiation image capturing apparatus used for the image capturing. Therefore, more time is needed and is more troublesome. Further, when the radiation image capturing apparatus used for the image capturing cannot be determined and image capturing needs to be executed again, this is a great strain for a patient and further, power consumption increases.

In the research for solving the problems of the above described portable radiation image capturing apparatus itself, the inventors of the present application found out that the problems of the above mentioned radiation image capturing system can be solved by using a portable radiation image capturing apparatus which can solve the above problems.

An object of the present invention is to solve the above problems of the radiation image capturing system and to provide a radiation image capturing system in which an operator does not need to use each of the portable radiation image capturing apparatuses by consciously identifying each of them, and further, in which correct image data can be obtained from the portable radiation image capturing apparatus actually used for the image capturing even when mistakenly identifying the portable radiation image capturing apparatus and in which unnecessary power consumption can be inhibited.

Means for Solving the Problem

In order to solve the above problems, a portable radiation image capturing apparatus includes a plurality of scanning lines and a plurality of signal lines which are disposed so as to intersect with each other, a plurality of image capturing elements which are two dimensionally arranged in regions defined by the plurality of scanning lines and the plurality of signal lines, respectively, and which generate electric charge according to an amount of radiation which is irradiated, an electric current detection unit which detects an electric current that flow in the apparatus due to a radiation irradiation, a reading circuit having a power supply mode in which electric charge generated and accumulated in each of the image capturing elements is read and converted into an electric signal and a waiting mode in which the electric charge is not read and power consumption is smaller comparing to the power supply mode, a battery which supplies power to each unit of the apparatus and a control unit which switches the reading circuit to the power supply mode from the waiting mode when the control unit detects that the radiation irradiation is started by detecting that a current amount of the electric current which is detected by the electric current detection unit increased when the reading circuit is in the waiting mode.

Further, a radiation image capturing system includes a radiation generation device which emits radiation, a plurality of portable radiation image capturing apparatuses of the above invention which are disposed in one image capturing room, each of which comprising a communication unit and a console which is made to correspond with the image capturing room in advance and which communicates with the portable radiation image capturing apparatuses in the image capturing room, and the control unit of the portable radiation image capturing apparatus switches a power consumption mode of the apparatus between a first mode in which power is not supplied to the reading circuit, a second mode in which the reading circuit is made to be in the waiting mode and a third mode in which the reading circuit is switched to the power supply mode from the waiting mode, the console comprises an input unit for inputting a predetermined information, the console switches a power consumption mode of all of the portable radiation image capturing apparatuses in the image capturing room to the second mode according to an input of the predetermined information by the input unit, and when the control unit of each of the portable radiation image capturing apparatuses which are switched to the second mode detects that a radiation irradiation is started, the control unit switches the power consumption mode to the third mode from the second mode, generates image data based on an electric charge which is read from the image capturing elements and transmits the generated image data to the console via the communication unit.

Further, a radiation image capturing system includes a plurality of image capturing rooms, a radiation generation device which emits radiation and which is disposed in each of the image capturing rooms, the portable radiation image capturing apparatuses of the above invention each of which comprises a communication unit, a plurality of the portable radiation image capturing apparatuses are disposed in each of the image capturing rooms and a console which communicates with each of the portable radiation image capturing apparatuses, and the control unit of the portable radiation image capturing apparatus switches a power consumption mode of the apparatus between a first mode in which power is not supplied to the reading circuit, a second mode in which the reading circuit is made to be in the waiting mode and a third mode in which the reading circuit is switched to the power supply mode from the waiting mode, the console comprises a selecting unit for selecting an image capturing room to be used for an image capturing among the image capturing rooms, the console switches a power consumption mode of all of the portable radiation image capturing apparatuses in the image capturing room which is selected by the selecting unit to the second mode according to a selecting of the image capturing room to be used for the image capturing by the selecting unit, when the control units of the portable radiation image capturing apparatuses which are switched to the second mode detect that the radiation irradiation is started, each of the control units switches the power consumption mode of the portable radiation image capturing apparatus to the third mode from the second mode, generates image data based on an electric charge read from the image capturing elements and transmits the generated image data to the console via the communication unit and the console stores the image data which is received from the selected image capturing room by making the image data correspond with the image capturing room.

Advantageous Effect of the Invention

According to the radiation image capturing apparatus of the present invention, the control unit detects that the radiation irradiation is started by detecting the increase in the current amount of the current that flows in the apparatus detected by the electric current detection unit. Further, when the starting of the radiation irradiation is detected, the reading circuits are switched to the normal power supply mode from the waiting mode in which power consumption is small.

Therefore, the reading circuits are maintained to be in the waiting mode in which power consumption is even smaller until radiation is irradiation to the radiation image capturing apparatus, the time period for the reading circuits to be in the power supply mode in which the power consumption is greater can be inhibited from being unnecessarily long. Thus, the amount of power consumption at the time of radiation image capturing can be reduced and the consumption rate of the battery can be reduced.

Further, there is not need for the control unit to control so as to have an interface with the radiation generation device in order to detect that the radiation irradiation is started by itself. Thus, even when the radiation generation apparatus and the radiation image capturing apparatus are manufactured by different manufacturers, for example, the starting of the radiation irradiation can be detected easily and accurately in the radiation image capturing apparatus itself and the mode of the reading circuits can be switched. Therefore, the starting of the radiation irradiation can be detected correctly regardless of where the main target body (area of interest) is positioned with respect to the radiation image capturing apparatus.

Moreover, according to the radiation image capturing system having the method as in the present invention, the console switches the power consumption mode of all of the portable radiation image capturing apparatuses in the image capturing room to the second mode in which the reading circuits are to be in the waiting mode according to the input of a predetermined information by the input unit. Then, when the control unit of the portable radiation image capturing apparatus which is switched to the second mode by the control of the console detects that radiation irradiation is started by detecting the increase in the current amount of the electric current that flows in the apparatus detected by the electric current detection unit, the control unit switches the power consumption mode thereof to the third mode in which the reading circuits are switched to the power supply mode from the second mode when the starting of radiation irradiation is detected. Further, the control unit of the portable radiation image capturing apparatuses which are switched to the third mode according to the detection of the starting of radiation irradiation generates image data based on the electric charge readout from the image capturing elements and transmits the image data to the console.

Therefore, even when a plurality of portable radiation image capturing apparatuses are disposed in the image capturing room, the image data is to be transmitted to the console only from the portable radiation image capturing apparatus which is actually used for the image capturing without an operator selecting the portable radiation image capturing apparatus which is to be used for the image capturing before the image capturing. Thus, there is no need for an operator to consciously identify each of the portable radiation image capturing apparatuses.

In particular, the radiation irradiation can be detected correctly in the portable radiation image capturing apparatus regardless of the positional relation of the target body with respect to the portable radiation image capturing apparatus which is to be used for the image capturing. Therefore, image data is transmitted to the console only from the portable radiation image capturing apparatus which was actually used for the image capturing every time. Thereby, the image capturing can be prevented from needing to be carried out again, and the radiation amount to be irradiated to the target body does not increase.

Further, image data is transmitted to the console only from the portable radiation image capturing apparatus which was actually used for the image capturing, even when an operator uses a portable radiation image capturing apparatus by incorrectly identifying it (when the portable radiation image capturing apparatus which is different from the portable radiation image capturing apparatus which was planned to be used for the image capturing in advance), the correct image data from the portable radiation image capturing apparatus which was actually used for the image capturing can be obtained in the console.

Furthermore, because the reading circuits are maintained to be in the waiting mode in which the power consumption is even smaller until radiation is irradiated to the portable radiation image capturing apparatus, the time period for the reading circuits to be in the power supply mode in which the power consumption is greater comparing to being in the waiting mode can be inhibited from being unnecessarily long. Thus, the amount of power consumption at the time of radiation image capturing can be reduced and the power can be prevented from being wasted.

Moreover, according to the radiation image capturing system having the method as in the present invention, when the image capturing room in which image capturing is to be carried out is selected among a plurality of image capturing rooms by the selecting unit, the console switches the power consumption mode of all of the portable radiation image capturing apparatuses in the image capturing room which is selected as the image capturing room in which the image capturing is to be carried out to the second mode in which the reading circuits are made to be in the waiting mode. Then, when the portable radiation image capturing apparatuses which are switched to the second mode by the control of the console detects that radiation irradiation is started by detecting increase in the current amount of the electric current that flows in the apparatus which is detected by the electric current detection unit, the portable radiation image capturing apparatus switches the power consumption mode to the third mode in which the reading circuits are made to switch to the power supply mode from the second mode by the control unit when the starting of the radiation irradiation is detected. Further, the portable radiation image capturing apparatus which is switched to the third mode according to the detection of starting of the radiation irradiation generates image data based on the electric charge readout from the image capturing elements and transmits the image data to the console.

Therefore, even when a plurality of portable radiation image capturing apparatuses are disposed in the image capturing room, by an operator only selecting the image capturing room in which the image capturing is to be carried out, the image data is to be transmitted to the console only from the portable radiation image capturing apparatus in the image capturing room which is actually used for the image capturing without an operator selecting the portable radiation image capturing apparatus 1 which is to be used for the image capturing before the image capturing. Thus, there is no need for an operator to consciously identify each of the portable radiation image capturing apparatuses.

Therefore, also in the radiation image capturing system having the above configuration, the same effective advantages as in the above described radiation image capturing system can be obtained.

Further, because the image data obtained in the console are stored by being corresponded with the selected image capturing room by the image capturing room units, an operator such as a technologist can extract only the image data of the image capturing which he/she handled by inputting the number of the image capturing room or the like in the console even when an arbitrary image capturing room among the plurality of image capturing rooms is used. Therefore, even when the system is configured so as to share the console among a plurality of operators such as technologists and among a plurality of image capturing rooms, image data can be made to respectively correspond with image capturing information correctly.

BRIEF DESCRIPTION OF THE DRAWINGS

FIG. 10 This is a table showing power consumption modes of the radiation image capturing apparatus, consumed power in each mode and operation state of each unit.

FIG. 16 This is a diagram showing an example of image capturing information.

FIG. 18 This is the second diagram of the flowchart showing an example of the process procedure in the radiation image capturing system according to the second embodiment.

FIG. 19 This is an example of a selecting screen of image capturing order information displayed in a display unit in the console.

FIG. 24 This is an example of a selecting screen of an image capturing room displayed in a display unit of the console.

BEST MODE FOR CARRYING OUT THE INVENTION

Figure 1:
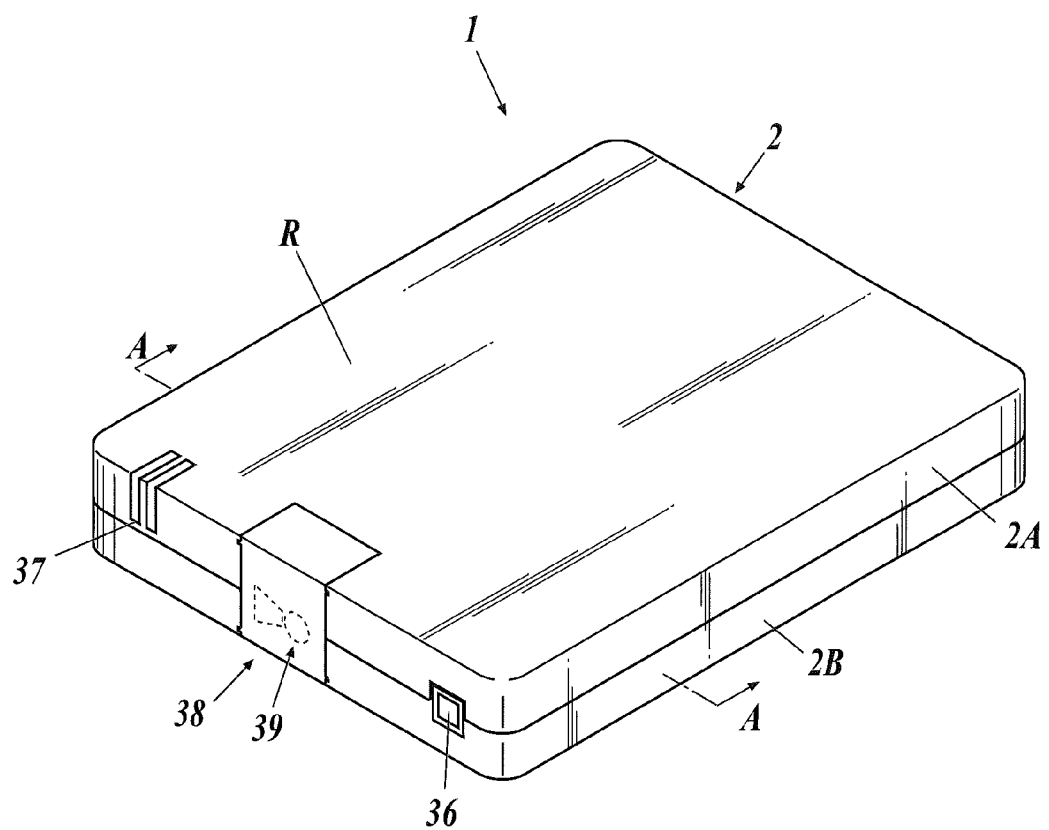
FIG. 1 This is a schematic diagram showing a radiation image capturing apparatus according to the first to the third embodiments.

Hereinafter, embodiments of a portable radiation image capturing apparatus and a radiation image capturing system according to the present invention will be described with reference to the drawings. However, the present invention is not limited to the following examples shown in the drawings.

Hereinafter, a portable radiation image capturing apparatus is to be simply indicated as a radiation image capturing apparatus. Further, hereinafter, an indirect type radiation image capturing apparatus which includes a scintillator and the like and obtains electric signal by converting the irradiated radiation into an electromagnetic wave of other wavelength such as visible light will be described as the radiation image capturing apparatus. However, the present invention can be applied to a so-called direct type radiation image capturing apparatus which directly detects radiation by image capturing elements without involving a scintillator and the like.

First Embodiment

Figure 2:
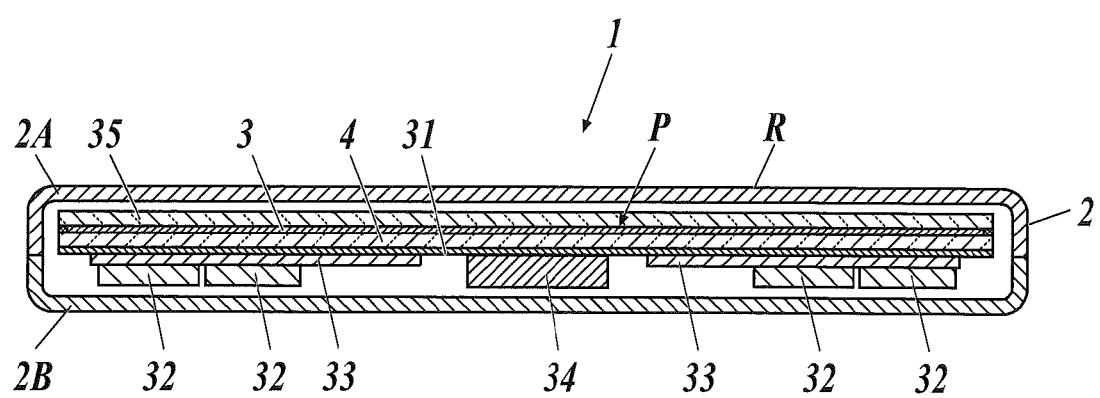
FIG. 2 This is a sectional view when cut along a line A-A of FIG. 1.

In the first embodiment of the present invention, the radiation image capturing apparatus will be described. FIG. 1 is an outer schematic diagram of the radiation image capturing apparatus according to the embodiment, and FIG. 2 is a sectional view when cut along the line A-A of FIG. 1. The radiation image capturing apparatus 1 according to the embodiment is configured as a cassette type portable radiation image capturing apparatus where a scintillator 3, a substrate 4 and the like are housed in a housing 2 of a case form as shown in FIGS. 1 and 2.

In the housing 2, at least the surface R (hereinafter, called the radiation incidence surface R) which is the surface which receives radiation irradiation is formed of a material such as a carbon plate or plastic which radiation can transmit. Here, in FIGS. 1 and 2, a case where the housing 2 is shown in a box type shape being formed of a frame plate 2A and a back plate 2B is shown. However, the housing 2 may be a monocock type in which the housing 2 is formed integrally as the X-ray image capturing apparatus disclosed in JP 2002-311526, for example.

As shown in FIG. 2, a platform 31 is disposed below the substrate 4 in the housing 2, and a PCB board on which electronic components 32 and the like are arranged, a cushioning member 34 and the like are attached on the platform 31. Further, in the embodiment, a glass board 35 which protects the substrate 4 and the scintillator 3 are disposed on the radiation incedence surface R side of the substrate 4 and the scintillator 3.

As for the scintillator 3, a scintillator in which fluorescent material is the main component and which outputs electromagnetic wave by converting into the electromagnetic wave of 300 to 800 nm wavelength, that is, electromagnetic wave centering on visible light when receiving radiation incidence is used. The scintillator 3 is attached on to the after mentioned detection part P of the substrate 4.

Figure 3:
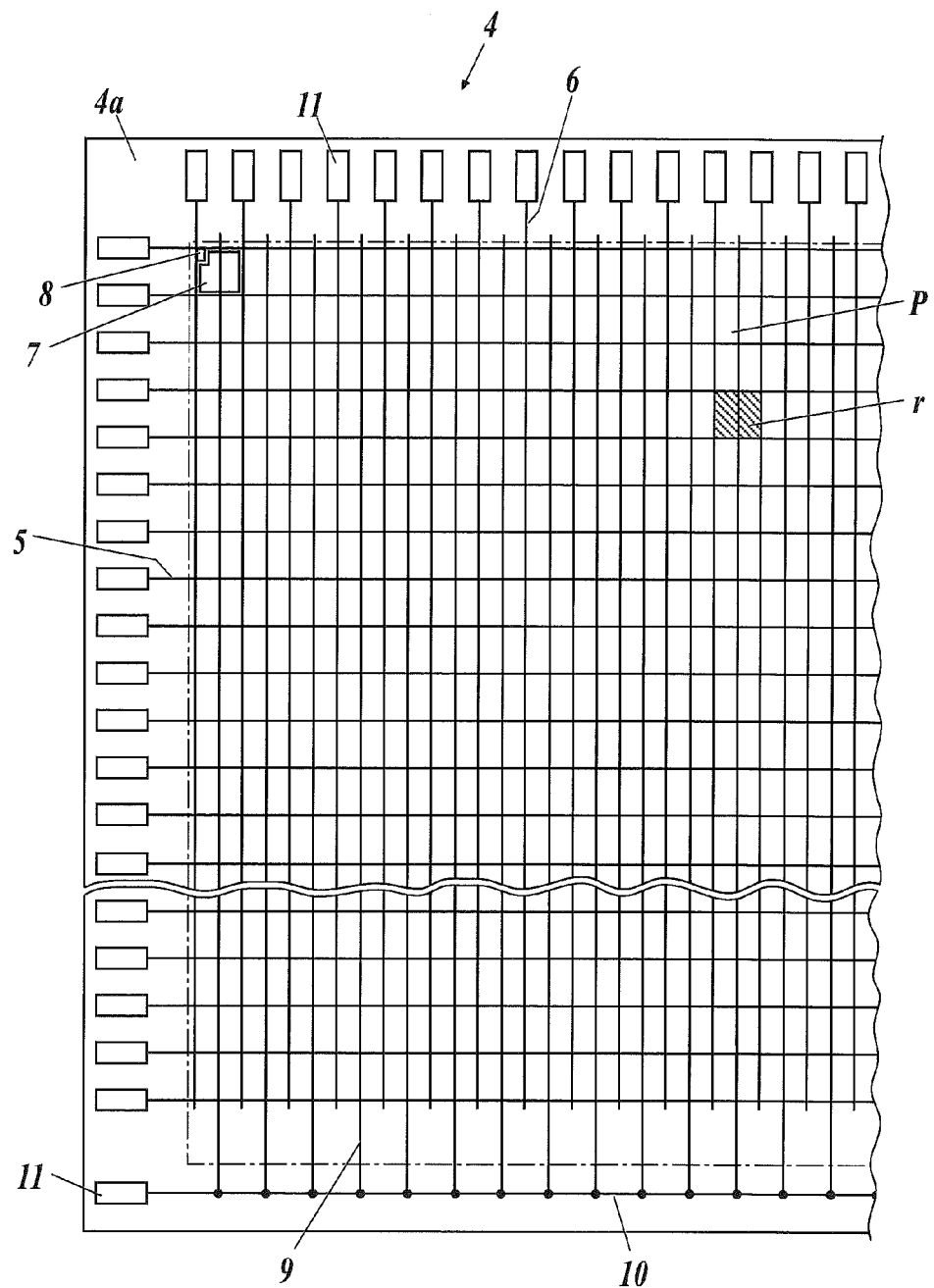
FIG. 3 This is a plane view showing a configuration of a substrate.

In the embodiment, the substrate 4 is configured of a glass board, and as shown in FIG. 3, a plurality of scanning lines 5 and a plurality of signal lines 6 are arranged on the surface 4a of the substrate 4, which faces the scintillator 3, so as to alternate with each other. In small areas r defined by the plurality of scanning lines 5 and the plurality of signal lines 6 on the surface 4a of the substrate 4, an image capturing elements 7 are provided respectively. In such way, the image capturing elements 7 are two dimensionally arranged on the substrate 4, and the entire area r in which a plurality of image capturing elements 7 are provided, that is the area indicated by dashed line in FIG. 3, is the detection part P.

In the embodiment, a photodiode which generates electric charge according to the amount of light (increases according to the amount of radiation entered into the scintillator 3) of the electromagnetic wave which is outputted by the radiation entered from the radiation incidence surface R being converted by the scintillator 3 is used as the image capturing element 7. However, a phototransistor or the like, for example, can be used other than photodiode. As shown in the enlarged views of FIGS. 3 and 4, each image capturing element 7 is connected to a source electrode 8s of TFT (thin film transistor) 8 which is a switch element. Further, a drain electrode 8d of the TFT 8 is connected to the signal line 6.

By the TFT 8 being in ON state, that is, by the gate of the TFT 8 being opened by ON voltage for signal reading being applied to the gate electrode 8g, electronic charge which is accumulated at the image capturing element 7 is to be released to the signal line 6. Further, by OFF voltage being applied to the scanning line 5 which is connected to the TFT 8 and by OFF voltage being applied to the gate electrode 8g, the TFT 8 be in OFF state, and the release of electronic charge to the signal line 6 from the image capturing element 7 is stopped and the electronic charge generated in the image capturing element 7 is retained and is accumulated in the image capturing element 7.

Here, the configuration of the image capturing elements 7 and the TFT 8 of the embodiment will be described briefly by using the sectional view shown in FIG. 5. FIG. 5 is a sectional view when cut along the line X-X of FIG. 4.

On the surface 4a of the substrate 4, the gate electrode 8g of the TFT 8 formed of Al, Cr or the like is formed by being laminated integrally with the scanning line 5. Further, at the part above the gate electrode 8g on the gate insulating layer 81 which is formed of silicon nitride (SiNx) and the like laminated on the gate electrode 8g and the surface 4a, the source electrode 8s which is connected with the first electrode 74 of the image capturing element 7 and the drain electrode 8d which is integrally formed with the signal line 6 are formed by being laminated via the semiconductor layer 82 which is formed of hydrogenated amorphous silicon (a-Si) or the like.

The source electrode 8s and the drain electrode 8d are divided by the first passivation layer 83 formed of silicon nitride (SiNx) or the like, and the first passivation layer 83 covers both of the electrodes 8s and 8d. Further, between the semiconductor layer 82 and the source electrode 8s and between the semiconductor layer 82 and the drain electrode 8d, ohmic contact layers 84a and 84b formed in n-type by doping a VI group element in hydrogenated amorphous silicon are respectively laminated. The TFT 8 is formed in the way as described above.

Moreover, in the part of the image capturing element 7, an auxiliary electrode 72 is formed by laminating Al, Cr or the like on the insulating layer 71 which is formed integrally with the gate insulating layer 81 on the surface 4a of the substrate 4. Further, the first electrode 74 which is formed of Al, Cr, Mo or the like is laminated above the auxiliary electrode 72 having the insulation layer 73 formed integrally with the first passivation layer 83 therebetween. The first electrode 74 is connected to the source electrode 8s of the TFT 8 via the hole H formed in the first passivation layer 83.

On the first electrode 74, a "n" layer 75 which is formed in n-type by doping a VI group element in hydrogenated amorphous silicon, an "i" layer 76 which is a conversion layer formed of hydrogenated amorphous silicon and a "p" layer 77 which is formed in p-type by doping a III group element in hydrogenated amorphous silicon are laminated in this order from the lower layer. Here, the order for laminating the "p" layer 77, the "i" layer 76 and the "n" layer 75 can be opposite of the above.

On the "p" layer 77, the second electrode 78 which is a transparent electrode such as ITO or the like is formed by being laminated, is configured so that the irradiated electromagnetic wave reaches the "i" layer 76 and the like. The image capturing element 7 is formed in the way as described above. Here, in the embodiment, a case where a so-called pin type image capturing element which is formed by laminating the "p" layer 77, the "i" layer 76 and the "n" layer 75 is used as the image capturing element 7 is described. However, the image capturing element 7 is not limited to the above pin type image capturing element.

Moreover, the bias line 9 which applies reverse bias voltage to the image capturing element via the second electrode 78 is connected to the upper surface of the second electrode 78 of the image capturing element 7. Here, upper surfaces of the second electrode 78 and the bias line 9 of the image capturing element 7, the first electrode 74 which extends to the TFT 8 side, the first passivation layer 83 of the TFT 8 and the like are covered with the second passivation layer 79 which is formed of silicon nitride (SiNx) from the above thereof.

Figure 4:
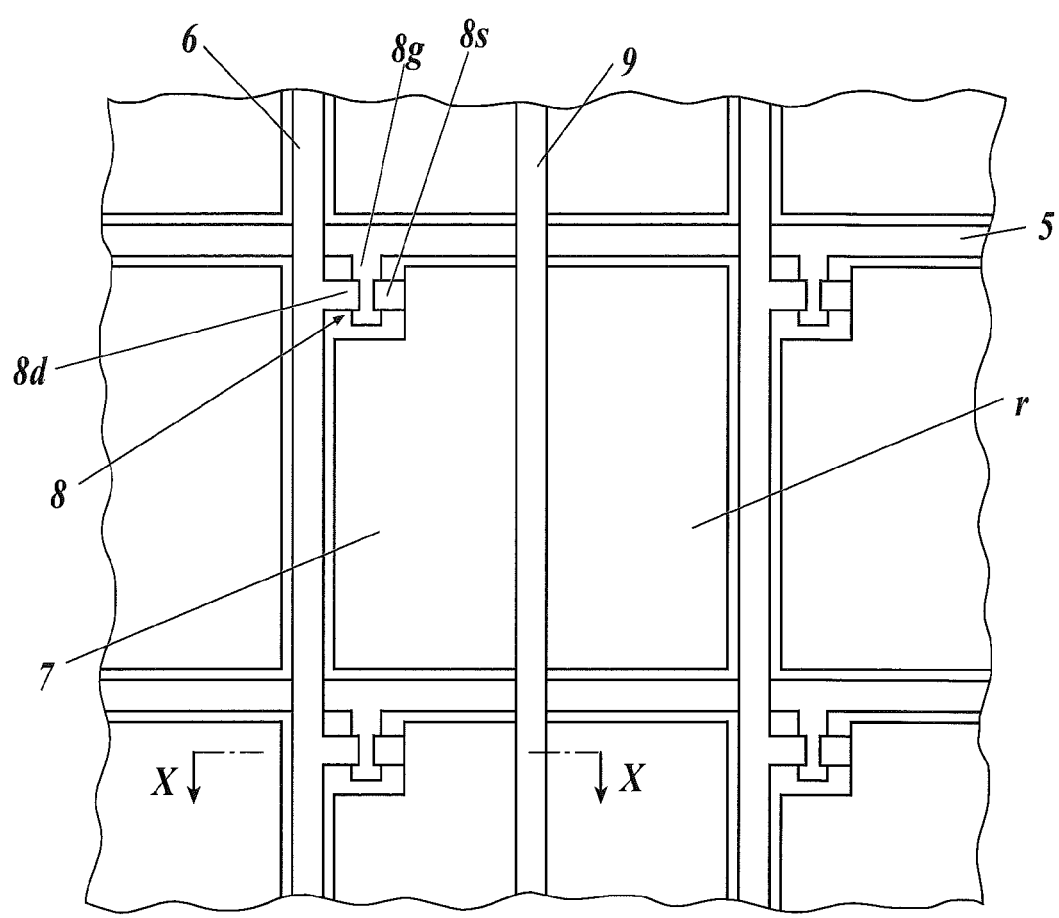
FIG. 4 This is an enlarged view showing a configuration of an image capturing element, a thin film transistor and the like formed in a small area on the substrate of FIG. 3.
Figure 5:
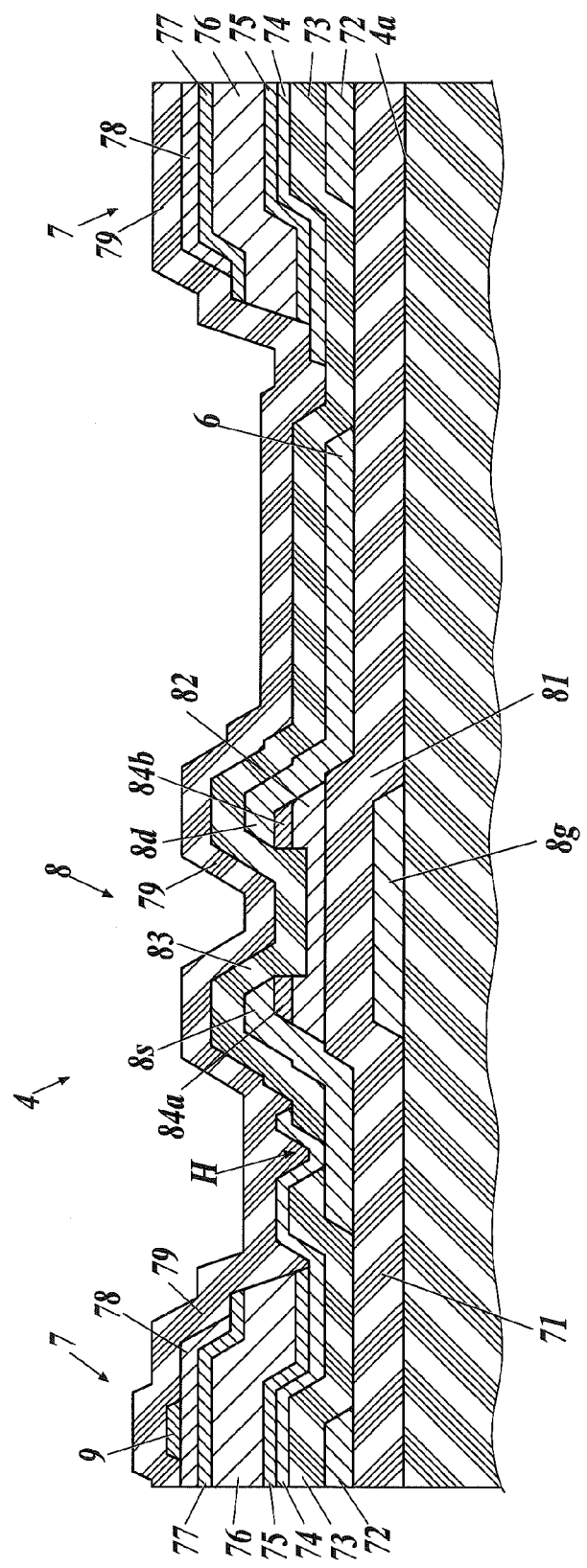
FIG. 5 This is a sectional view when cut along a line X-X of FIG. 4.

In the embodiment, one bias line 9 is connected to each of the plurality of image capturing elements 7 which are arranged in a line and each bias line 9 is disposed parallely to each signal line 6 as shown in FIGS. 3 and 4. Further, each bias line 9 is connected to the one connection 10 at the position outside of the detection part P of the substrate 4.

Figure 6:
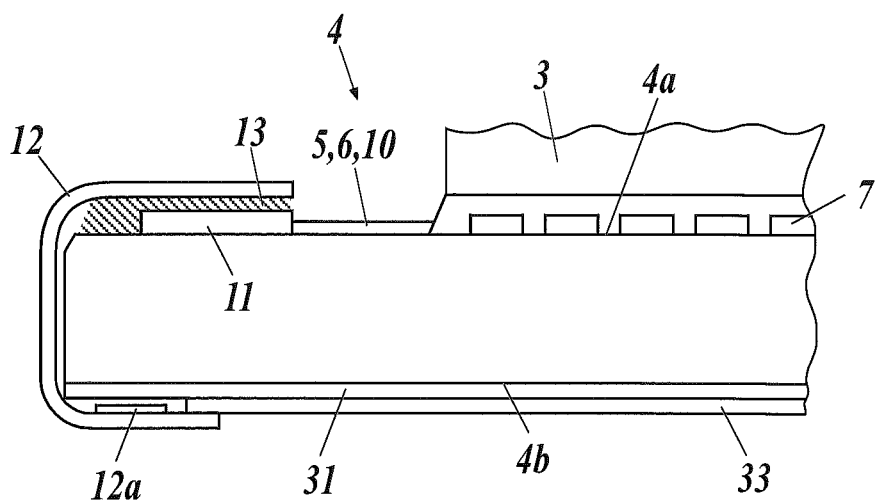
FIG. 6 This is a side view explaining the substrate in which COF and PCB boards and the like are attached.

In the embodiment, the connections 10 of the scanning lines 5, the signal lines 6 and the bias lines 9 is connected to the input/output terminals 11 (also called as a pad) which are disposed near the edge portion of the substrate 4. As shown in FIG. 6, the COF (Chip On Film) 12 in which a chip such as IC 12a is embedded is connected to each of the input/output terminal 11 via the anisotropic conductive adhesive 13 such as an anisotropic conductive film and an anisotropic conductive paste.

Further, the COF 12 is routed to the back surface 4b side of the substrate 4 and is to connect with the above mentioned PCB board 33 at the back surface 4b side. In such way, the substrate 4 portion of the radiation image capturing apparatus 1 is formed.

On the other hand, as shown in FIG. 1, at the side surface of one of the short sides of the housing 2, the power switch 36 of the radiation image capturing apparatus 1, an indicator 37 which displays the operation state of various kinds and the like are provided. Further, at this side surface, a lid member 38 for replacing the embedded battery which is not shown in FIG. 1 is provided, and an antenna device 39 for the radiation image capturing apparatus 1 to carrying out sending and receiving of data, signals and the like in a wireless format with an external device is embedded at the lid member 38.

The place where the antenna device 39 is to be provided is not limited to the side surface of one of the short sides of the housing 2 as in the embodiment, and the antenna device 39 can be provided at other place. Further, the number of the antenna device 39 is not necessarily limited to one, and the antenna devices can be suitably provided as much as needed.

Figure 7:
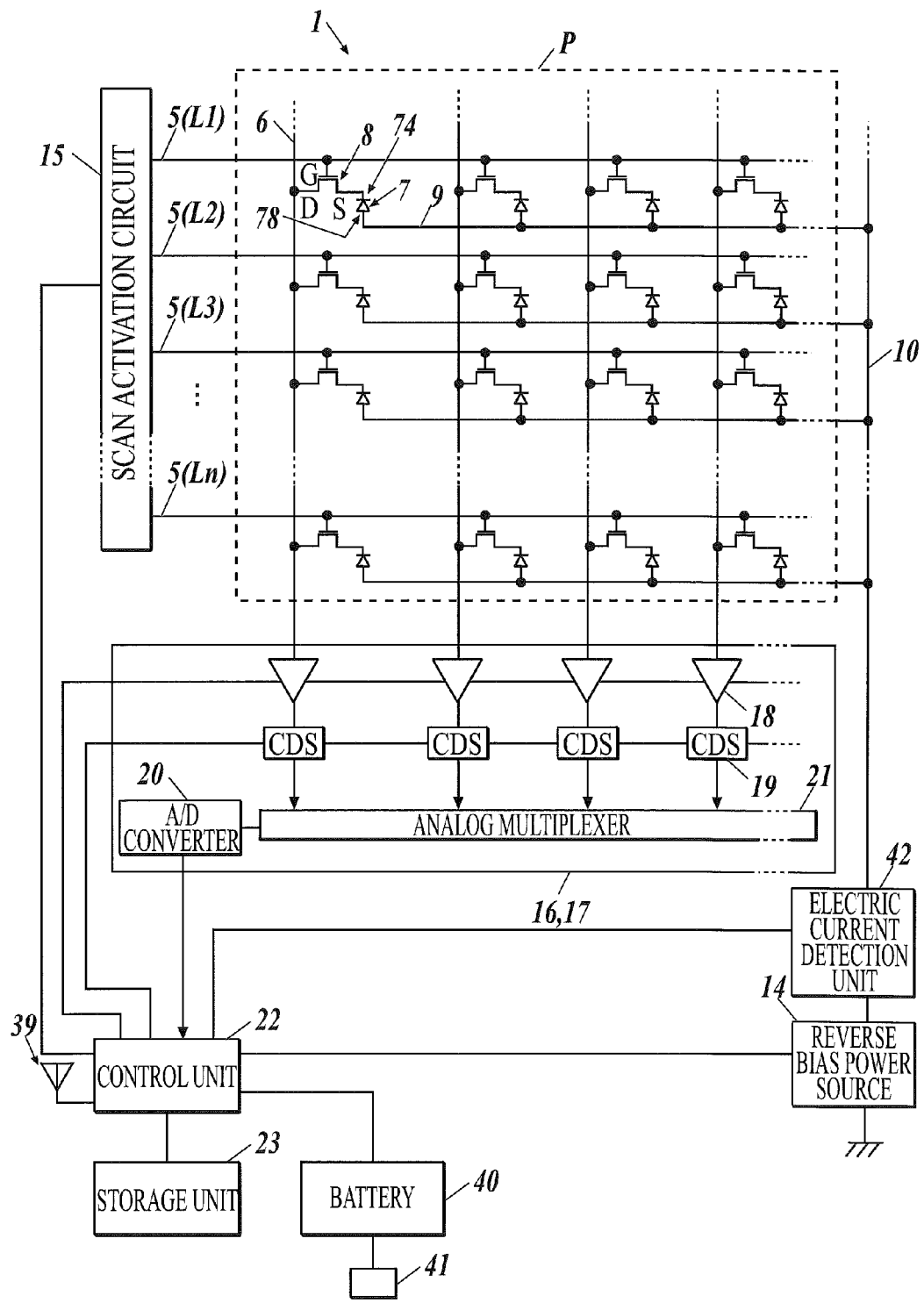
FIG. 7 This is a diagram showing an equivalent circuit schematic of the radiation image capturing apparatus.
Figure 8:
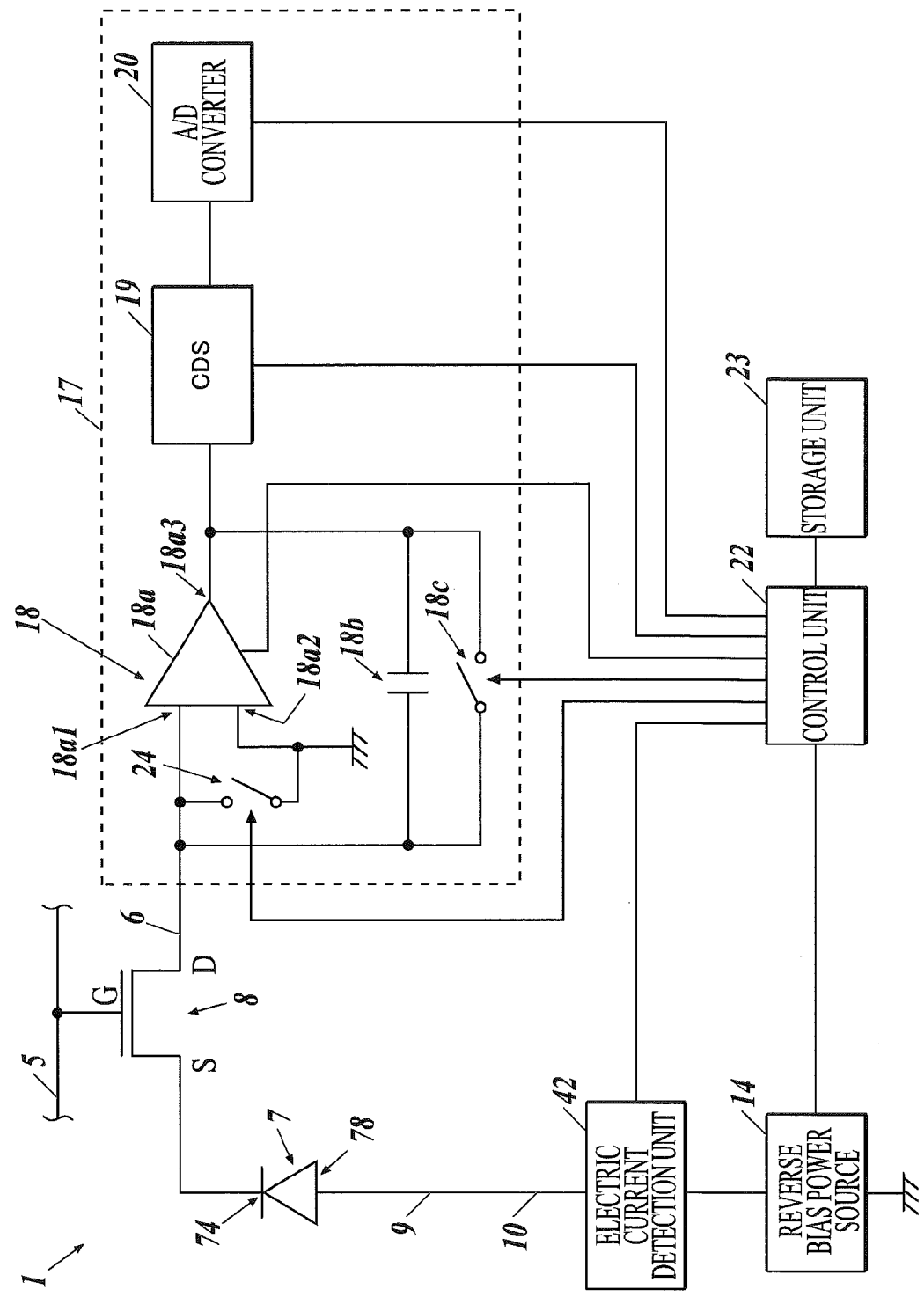
FIG. 8 This is an equivalent circuit schematic for one pixel of FIG. 7.

Here, the circuit configuration of the radiation image capturing apparatus 1 will be described. FIG. 7 is an equivalent circuit schematic of the radiation image capturing apparatus 1 according to the embodiment, and FIG. 8 is an equivalent circuit schematic for one of the pixels that constituted the detection part P.

As described above, in each of the image capturing elements 7 in the detection part P of the substrate 4, the second electrode 78 thereof is connected to the bias line 9 and the connection 10, and the connection 10 is connected to the reverse bias power source 14. The reverse bias power source 14 supplies reverse bias voltage to be applied to each of the image capturing elements 7 via the connection 10 and each of the bias lines 9. Further, the reverse bias power source 14 is connected to the control unit 22, and the control unit 22 controls the reverse bias voltage which is to be applied to each of the image capturing elements 7 from the reverse bias power source 14.

The first electrode 74 of each of the image capturing elements 7 is connected to the source electrode 8s (indicated as S in FIG. 7) of the TFT 8, and the gate electrode 8g (indicated as G in FIG. 7) of each of the TFT 8 is connected to each of the scanning lines 5 which extends from the scan activation circuit 15. Further, the drain electrode 8d (indicated as D in FIG. 7) of each of the TFT 8 is connected to each of the signal lines 6.

When the ON voltage for reading out signals is applied to the gate electrode 8g of the TFT 8 from the scan activation circuit 15 via the scanning line 5, the gate of the TFT 8 be in the ON state, and electrical charge which is accumulated in the image capturing element 7 is to be read out to the signal line 6 from the grain electrode 8d via the source electrode 8s of the TFT 8.

Each of the signal lines 6 is respectively connected to each of the reading circuits 17 formed in the reading IC 16. Here, a predetermined number of reading circuits 17 are provided in the reading IC 16, and the reading circuits 17 corresponding to the number of signal lines 6 are to be provided by providing a plurality of reading IC 16.

The reading circuit 17 is constituted of an amplifier circuit 18, the correlated double sampling circuit 19 and an A/D converter 20, and one reading circuit 17 is provided for one signal line 6. However, in the embodiment, the A/D converter 20 is shared by a plurality of circuits, and the electric signals which are outputted from the correlated double sampling circuits 19 are transmitted to the A/D converter in order via the analog multiplexer 21 and the electric signals are to be converted into digital values in order in the A/D converter 20.

Then, the electric charge is read out through the signal line 6 from the image capturing element 7 in the reading circuit 17, and charge-voltage conversion, amplifying and the like are carried out to the electric charge to be converted into electrical signal for each image capturing element 7. Here, the correlated double sampling circuit 19 is indicated as CDS in FIGS. 7 and 8. Further, the analog multiplexer 21 is omitted in FIG. 8.

In the embodiment, the amplifier circuit 18 is constituted of a charge amplifier circuit, and is configured of an operational amplifier 18a and a condensor 18b and the switch 18c for resetting the electric charge being connected parallely to the operational amplifier 18a. Further, the signal line 6 is connected to the inverting input terminal 18a1 at the input side of the operational amplifier 18a of the amplifier circuit 18, and the non-inverting input terminal 18a2 at the input side of the amplifier circuit 18 is grounded (GND).

Hereinafter, a case where the non-inverting input terminal 18a2 at the input side of the amplifier circuit 18 is grounded will be described. However, the configuration may be that a predetermined initial voltage is to be applied to the non-inverting input terminal 18a2 at the input side of the amplifier circuit 18 and the similar description as the following description can also be applied to such case. That is, the embodiment corresponds to the case where the initial voltage is set to 0 [V].

Further, the switch 18c for resetting the electric charge of the amplifier circuit 18 is connected to the after mentioned control unit 22, and ON/OFF of the switch 18c is to be control by the control unit 22. When the TFT 8 of the image capturing element 7 is made to be in the ON state while the switch 18c for resetting the electric charge is in OFF state (that is, when the ON voltage is applied to the gate electrode 8g of the TFT 8 via the scanning line 5), the electric charge released from the image capturing element 7 flows into the condensor 18b and is accumulated, and the voltage value according to the amount of accumulated electric charge is to be output from the output terminal 18a3 of the operational amplifier 18a. In such way, the amplifier circuit 18 outputs the voltage value according to the amount of electric charge outputted from each of the image capturing elements 7 to carry out the charge-voltage conversion and amplifying.

Furthermore, when the switch 18c for resetting the electric charge is made to be in the ON state, the input side and the output side of the amplifier circuit 18 are shunted and the electric charge accumulated in the condensor 18b is released so that the amplifier circuit 18 is reset. Here, the amplifier circuit 18 may be configured so as to output the current according to the electric charge which is outputted from the image capturing element 7.

At the output side of the amplifier circuit 18, the correlated double sampling circuit (CDS) 19 is connected. In the embodiment, the correlated double sampling circuit (CDS) 19 includes a sample holding function, and ON/OFF of the sample holding function in the correlated double sampling circuit 19 is controlled by a pulse signal which is transmitted from the control unit 22.

Figure 9:
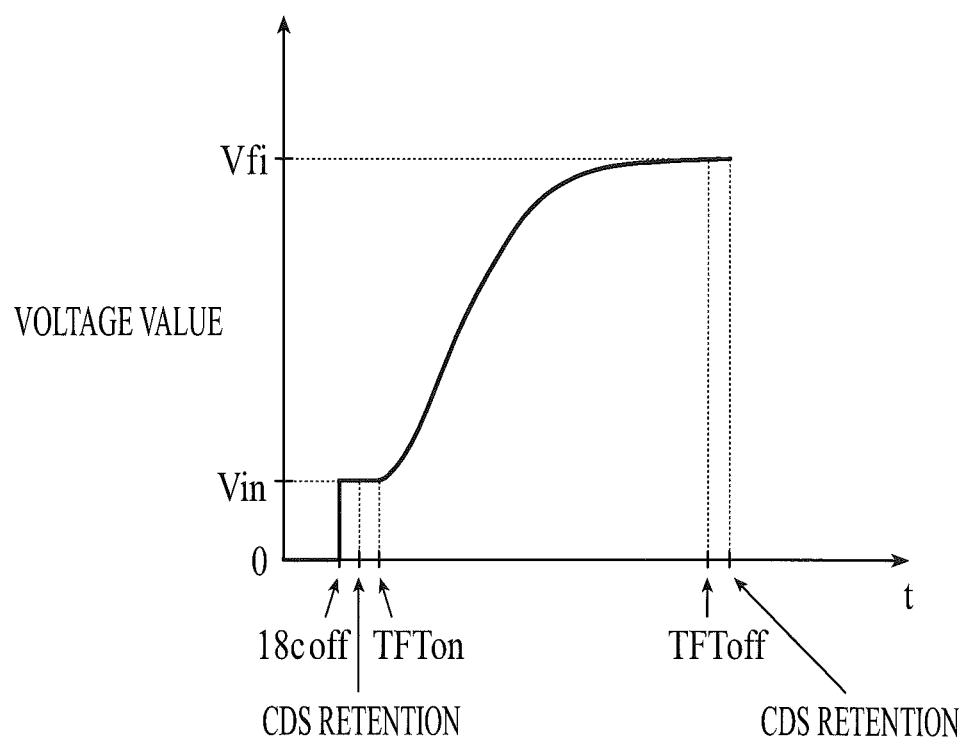
FIG. 9 This is a graph explaining a change in voltage value output from an amplifier circuit over time and an operation in a correlated double sampling circuit.

That is, as shown in FIG. 9, when the correlated double sampling circuit 19 receives the first pulse signal from the control unit 22 just after the switch 18c for resetting the electric charge is made to be in the OFF state (see "18c off" in the drawing), the correlated double sampling circuit 19 retains the voltage value Vin which is outputted from the amplifier circuit 18 at that time (see "CDS retention" on the left side of the drawing).

Here, when the switch 18c for resetting the electric charge is made to be in the OFF state, kTC noise occurs right at that time and the electric charge q caused by the kTC noise accumulates in the condensor 18b of the amplifier circuit 18. Therefore, the voltage value outputted from the amplifier circuit 18 increases to Vin from 0 [V] at the time when the switch 18c for resetting the electric charge is made to be in the OFF state.

Then, the TFT 8 of the image capturing element 7 is made to be in the ON state (see "TFT on" in the drawing) and the electric charge which is released from the image capturing element 7 flows in to the condensor 18b and is accumulated. Further when the second pulse signal is received from the control unit 22 just after the TFT 8 of the image capturing element 7 is made to be in the OFF state (see "TFT off" in the drawing) at the time when the voltage value outputted from the operational amplifier 18a increases, the correlated double sampling circuit 19 retains the voltage value Vfi which is outputted from the amplifier circuit 18 at that time (see "CDS retention" on the right side in the drawing).

Then, the correlated double sampling circuit 19 outputs the difference value Vfi-Vin of the voltage values to the downstream side as the electric signal. The electric signals corresponding to the electric charges generated in the image capturing elements 7 which are outputted from the correlated double sampling circuit 19 are transmitted to the analog multiplexer 21 (see FIG. 7) and are transmitted to the A/D converter 20 in order from the analog multiplexer 21. Then, the electric signals are converted into electric signals of digital values in the A/D converter 20 in order and are outputted and stored in the stored unit 23 in order.

The above described is the process of the reading circuits 17 to read out and convert the electric charge generated and accumulated in each of the image capturing elements into electric signal, or, the process of the reading circuits 17 in the power supply mode where the reading circuits 17 are capable of converting the electric charge which is at least read out as described above and convert into electric signal. However, the reading circuits 17 further include a waiting mode in which the reading circuits 17 do not carry out reading of electric charge from each of the image capturing elements 7. In order to describe the waiting mode, the electric current detection unit 42 needs to be described. Therefore, the waiting mode of the reading circuits 17 will be described after describing the after-mentioned electric current detection unit 42.

The control unit 22 is configured of a microcomputer including CPU (Central Processing Unit) and the like and a specialized control circuit, and the control unit 22 controls operation and the like of each unit of the radiation image capturing apparatus 1. Further, the storage unit 23 which is configured of RAM (Random Access memory) and the like is connected to the control unit 22.

As described above, the control unit 22 controls the reverse bias voltage to be applied to each of the image capturing elements 7 by controlling the reverse bias power source 14, and the control unit 22 drives the scan activation circuit 15 and controls the reading of electric signal from each of the image capturing elements 7 by controlling the amplifier circuit 18, the correlated double sampling circuit 19 and the like in each of the reading circuits 17.

Moreover, the above mentioned antenna device 39 is connected to the control unit 22, and further, the battery 40 for supplying power to each unit of each of the image capturing element 7 and the like is connected to the control unit 22. In such way, the battery 40 is embedded in the housing 2 of the radiation image capturing apparatus 1, and a joining terminal 41 which is used when charging the battery 40 by supplying power to the battery 40 from an external device is attached to the battery 40.

Furthermore, the electric current detection unit 42 is provided at the connection 10 of the bias line 9, and the electric current detection unit 42 is connected to the control unit 22.

The electric current detection unit 42 detects the electric current that flows in the connection 10 when the bias lines 9 are bound. In the embodiment, the electric current detection unit 42 is omitted from the drawings. However, the electric current detection unit 42 includes resistance having a predetermined resistance value which is serially connected to the connection 10 and a difference amplifier which measures the voltage between the terminals of the resistance. The electric current detection unit 42 detects the electric current that flows through the connection 10 by converting the electric flow into the voltage value by measuring the voltage between the terminals of the resistance by the difference amplifier.

As for the resistance to be provided to the electric current detection unit 42, a resistance having a large resistance value such as 100 kΩ or 1 MΩ in order to amplify the electric current that flows through the connection 10 which is not necessarily large. The electric current detection unit 42 outputs the voltage value corresponding to the current value that flows through the connection detected by converting as described above to the control unit 22.

Here, when the resistance value of the resistance provided in the electric current detection unit 42 is large as described above, there is a possibility of interfering greatly with the electric current that flows through the bias lines 9, the connection 10 and the like when reading out the electric charge accumulated by the radiation irradiation, for example. Therefore, it is preferable that a switch or the like is provided to the electric current detection unit 42 so that between the terminals of the resistance can be suitably shunted.

As will be described later, when the electron-hole pairs are generated in each image capturing element 7 by radiation being irradiated to the radiation image capturing apparatus 1, in the embodiment, the electron holes move to the second electrode 78 side in the image capturing element 7 and a part thereof flow into the bias line 9 to be collected and flow through the connection 10. Thereby, the electric current is detected by the electric current detection unit 42 and the voltage value V corresponding to the detection electric current is outputted as shown in the after-mentioned FIG. 11.

At that time, a closed loop including the image capturing element 7, the reverse bias power source and the like, or the electric current which flown out from the image capturing 7 does not flow in the bias line 9 and the connection 10. Therefore, in the present invention, the closed loop is to be formed when the above mentioned reading circuits 17 are in the waiting mode.

As described above, when the reading circuits 17 are in the waiting mode, the electric charge is not read out from each of the image capturing elements 7. Further, in the embodiment, when the reading circuits 17 are made to be in the waiting mode, current is not applied to the reading circuits 17 themselves and the charge amplifier circuit which constitutes the amplifier circuits 18 are made to be in a non-operating state.

When the charge amplifier circuit which constitutes the amplifier circuit 18 is made to be in the non-operating state, electric current does not flow between the inverting input terminal 18a1 and the non-inverting input terminal 18a2 at the input side of the operational amplifier 18a of the amplifier circuit 18 (see FIG. 8). Therefore, the loop which is electrically connected such as "grounding (GND)→reverse bias power source 14→(electric current detection unit 42)→image capturing element 7→TFT 8→signal line 6" is to be cut at the operational amplifier 18a part. Thus, the closed loop including the image capturing element 7, the reverse bias power source 14 and the like cannot be formed.

In view of the above, in the embodiment, at each of the operational amplifiers 18a of the amplifier circuits 18 of the reading circuits 17, a mode switching switch 24 which joins the inverting input terminal 18a1 to which the signal line 6 is connected and the non-inverting input terminal 18a2 which is grounded and switches the modes between shunt and shunt-release is provided on the upstream side of the operational amplifier 18a.

The mode switching switch 24 is configured of MOSFET (MOS type field effect transistor) in the embodiment. Further, the gate electrode (not shown in the drawing) of the MOSFET which is the mode switching switch 24 and the control unit 22 are connected, and ON/OFF of the mode switching switch 24 is controlled by switching between applying and stop applying of voltage to the gate electro from the control unit 22.

When the reading circuits 17 are made to be in the waiting mode, the control unit 22 does not apply current to the reading circuits 17 and makes the charge amplifier circuit which constituted the amplifier circuit 18 be in the non-operating state, and also, makes each of the mode switching switch 24 be in the ON state and makes the inverting input terminal 18a1 and the non-inverting input terminal 18a2 of each of the operational amplifier 18a of the amplifier circuits 18 of the reading circuits 17 be shunted.

In such way, when each of the mode switching switch 24 is made to be in the ON state, the closed loop of "grounding (GND)→reverse bias power source 14→(electric current detection unit 42)→image capturing element 7→TFT 8→mode switching switch 24→grounded (GND)" can be formed even when the charge amplifier circuit which constitutes the amplifier circuit 18 is in the non-operating state as shown in FIG. 8.

Furthermore, when each of the reading circuits 17 is made to be in the power supply mode, current is applied to the reading circuit 17 and the charge amplifier circuit which constitutes the amplifier circuit 18 is made to be in the operating state, and also, the mode switching switch 24 is made to be in the OFF state.

Therefore, the amount of power consumption is to be small in the reading circuits 17 when the reading circuits 17 are in the waiting mode where reading out of the electric charge is not carried out and the electric current that flows through the connection 10 of the bias line 9 can be detected easily by the electric current detection unit 42 by forming the closed loop than when the reading circuits 17 are in the power supply mode where the reading circuits 17 are capable of reading out the electric charge which is generated and accumulated in each of the image capturing elements 7 and converting into electric signals as described above.

Moreover, the control unit 22 detects that irradiation of radiation to the radiation image capturing apparatus 1 is started by the increase in the current amount of the electric current that flows through the connection 10 of the bias lines 9 detected by the electric current detection unit 42 when the reading circuits 17 are in the waiting mode. Further, when starting of radiation irradiation is detected, the control unit 22 makes the reading circuits 17 switch to the power supply mode from the waiting mode.

Hereinafter, the operation of the radiation image capturing apparatus 1 according to the embodiment will be described, and also, the detection of starting of radiation irradiation and switching of the reading circuits 17 to the power supply mode from the waiting mode which are carried out by the control unit 22 will be described.

In the embodiment, the mode of the reading circuits 17 can be switched as described above and the power consumption mode can be switched at least between mode 1 to mode 3 as shown in the table of FIG. 10 in the radiation image capturing apparatus 1. Here, in the table of FIG. 10, S indicates the mode switching switch 24 and IC indicates the reading circuits 17 and the reading IC 16.

First, in the first mode "mode 1" (sleep state) in which the power consumption is the smallest, the reverse bias voltage is not applied to each of the image capturing elements 7 from the reverse bias power supply 14 and voltage is not applied to each of the TFT 8 as shown in FIG. 10.

That is, when switching ON/OFF of each of the TFT 8, normally, the ON voltage for signal reading of +15 [v], for example, is applied to the gate electrode 8g when making each of the TFT 8 be in the ON state and the OFF voltage of −10 [v], for example, is applied to the gate electrode 8g when making each of the TFT 8 be in the OFF state. However, in the first mode "mode 1", both ON voltage and OFF voltage are not applied to the gate electrode 8g of each of the TFT 8.

Further, in the first mode "mode 1", voltage is not applied to the gate electrode of the mode switching switch 24 and the mode switching switch 24 is made to be in the OFF state and also, power is not supplied to the reading circuits 17 (the reading IC 16). That is, the radiation image capturing apparatus 1 is not in the state where power is completely off, however, the radiation image capturing apparatus 1 is in a state where power is supplied only to the necessary units such as the control unit 22, the storage unit 23 and the like as needed.

Therefore, as shown in the table of FIG. 10, the power consumption in the first mode "mode 1" is a small value such as 1.6 [W], for example, in the radiation image capturing apparatus 1 of the embodiment. Here, in the embodiment, the antenna device 39 which is the communication unit is in the ON state so that the radiation image capturing apparatus 1 can receive signals from outside even in the sleep state which is the first mode "mode 1". However, for example, when the radiation image capturing apparatus 1 is provided with an activation switch, for example, and ON/OFF of the antenna device 39 which is the communication unit can be switched by the activation switching operation of an operator and when the antenna device 39 is made to be in the OFF state in the first mode "mode 1", the power consumption in the first mode "mode 1" will be even smaller value such as 0.1 [W], for example.

Thereafter, when switching of the mode of the radiation image capturing apparatus 1 is instructed by the manual operation of an operator such as a radiation technologist or by receiving a signal from an external device in order to carry out radiation image capturing, the control unit 22 switches the power consumption mode of the radiation image capturing apparatus 1 to the second mode "mode 2" (waiting for irradiation state).

As shown in FIG. 10, the reverse bias voltage is applied to each of the image capturing elements 7 from the reverse bias power source 14 and, first, the OFF voltage is applied to each of the TFT 8 in the second mode "mode 2". Moreover, in order to form the above mentioned closed loop, the mode switching switch 24 is made to be in the ON state and the reading circuits 17 are made to be in the waiting mode. However, current is not applied to the reading circuits 17 themselves. In such way, as shown in the table of FIG. 10, the power consumption in the second mode "mode 2" is to be 5.2 [W], for example.

In the embodiment, when the control unit 22 switches the power consumption mode of the radiation image capturing apparatus 1 to the second mode "mode 2", the control unit 22 carries out the reset process of the image capturing element 7. In the reset process, the control unit 22 makes each of all of the TFT 8 be in the ON state by applying the ON voltage for signal reading to the gate electrode 8g of the TFT 8 which is the switch element of each of the image capturing elements 7 via each of the scanning line 5 from the scan activation circuit 15, and the control unit 22 makes each of the bias lines 9 release extra electric charge which is accumulated in the image capturing element 7.

Here, there is no need to detect the current that flows through the connection 10 of the bias lines 9 in the reset process. Therefore, it is preferable to shunt between the terminals of the resistance of the electric current detection unit 42 by making the switch of the electric current detection unit 42 be in the ON state so as not to interfere with the flowing of extra electric charge in the reset process.

When the reset process is finished, the control unit 22 applies the OFF voltage to the gate electrode 8g of the TFT 8 from the scan activation circuit 15 via the scanning line 5 and makes all of the TFT 8 be in the OFF state, and the control unit 22 waits for radiation irradiation to the radiation image capturing apparatus 1.

As described above, the control unit 22 detects the starting of radiation irradiation to the radiation image capturing apparatus 1 by the increase in the current amount of the electric current that flows through the connection 10 of the bias lines 9 being detected by the electric current detection unit 42. Hereinafter, the radiation irradiation to the radiation image capturing apparatus 1 and the increase in current amount of the electric current that flows through the connection 10 of the bias lines 9 will be described.

When radiation is irradiated to the radiation image capturing apparatus 1, the radiation which transmitted through the target body that exists on the radiation incidence surface R (see FIG. 1) of the radiation image capturing apparatus 1 and in proximity thereof enters the scintillator 3 (see FIG. 2) in the embodiment. Further, the radiation is converted into an electromagnetic wave in the scintillator 2 and the electromagnetic wave enters the image capturing elements 7 which are disposed below thereof.

In each image capturing element 7, when the electromagnetic wave which enters reaches the "i" layer 76 (see FIG. 5), the electron-hole pair is generated in the "i" layer 76 by the energy of the electromagnetic wave. Further, according to the potential gradient which is formed in the image capturing element 7 by the reverse bias voltage being applied, the electric charge of either one of the electrons and the holes which are generated (in the embodiment, holes) move to the second electrode 78 side and the electric charge of the other of the electrons and the holes (in the embodiment, electrons) move to the first electrode 74 side.

In such case, because the TFT 8 is in the OFF state by the OFF voltage being applied to the gate electrode 8g of the TFT 8. Therefore, the electrons which moved to the first electrode 74 side in the image capturing element 7 cannot flow out to the signal line 6. Thus, the electrons are accumulated near the first electrode 74. Further, holes in the same amount as the electrons are accumulated near the second electron 78.

However, normally, leaking of electrons to the signal line 6 cannot be prohibited completely in the TFT 8, and electrons in the image capturing element 7 leaks via the TFT 8 although the amount thereof is very small. Accordingly, holes in the same amount as the electrons leak to the bias line 9 from the second electrode 78 of the image capturing element 7. At that time, because the mode switching switch 24 of each of the reading circuits 17 is in the ON state in the second mode "mode 2" (see FIG. 10), the closed loop is formed and the electric current which leaked from the image capturing element 7 easily flows into the bias lines 9 and the connection 10.

Then, normally, as the amount of electrons and holes accumulated in the image capturing element 7 increases, the amount of electrons and holes to be leaked increases. Further, although the amount of holes that leak from the second electrode 78 of each of the image capturing element 7 to the bias line 9 is very small, the amount reaches the level that can be detected by the electric current detection unit 42 when the holes that leak from each of million to ten million to image capturing elements are collected to the connection 10 of the bias lines 9.

Figure 11:
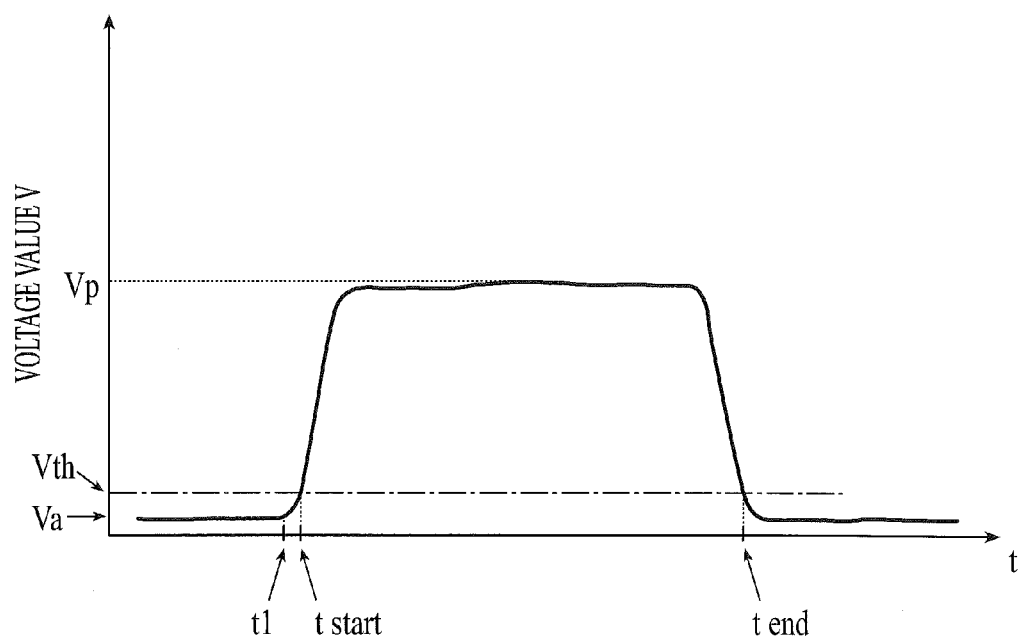
FIG. 11 This is a graph showing an example transition of outputted voltage value when the electric current flowing through a connection of a bias wire is converted into a voltage value by a electric current detection unit.

Therefore, when the switch of the electric current detection unit 42 is made to be in the OFF state and the shunt between the terminals of the resistance of the electric current unit 42 is released and when the current which is small amount that flows through the connection 10 of the bias lines 9 is amplified to be detected as a voltage value, the current that flows in the connection 10 increases when the radiation irradiation is started in the radiation image capturing apparatus and the holes among the electron-hole pairs generated in the image capturing elements 7 start to flow into the bias line 9 as shown in FIG. 11, for example, and the voltage value V to be output to the electric current detection unit 42 starts to increase as shown at the time t1 in FIG. 11.

Therefore, for example, the configuration may be such that a predetermined threshold value Vth is set for the voltage value V to be output from the electric current detection unit 42 in advance and to detect that the radiation irradiation is started at the time of "t start" when the voltage value V exceeded the threshold value Vth by the control unit 22 monitoring whether the output voltage value V exceeded the threshold value Vth or not.

In contrary, when the radiation irradiation is stopped and the radiation image capturing is finished, the electron-hole pairs are not generated in the image capturing elements 7 and now, the voltage value V starts to decrease. Therefore, for example, the configuration may be such that the radiation irradiation is determined as being ended at the time "t end" when the voltage value V outputted from the electric current detection unit 42 be equal to or smaller than the threshold value Vth.

In the embodiment, the control unit 22 detects the starting and finishing of the radiation irradiation to the radiation image capturing apparatus 1 in the way described above. By detecting the starting of the radiation irradiation to the radiation image capturing apparatus 1 as described above, the holes which flow out from each of million to ten million of image capturing elements are collected to the connection 10 of the bias lines 9 and reaches the amount of the level that can be detected by the electric current detection unit 42. Therefore, the starting of the radiation irradiation can be detected correctly regardless of where the main target body (area of interest) is positioned with respect to the radiation incidence surface R (see FIG. 1) of the radiation image capturing apparatus 1.

Here, even when radiation is not irradiated to the radiation image capturing apparatus 1, so-called dark electric charge is generated and accumulated due to thermal excitation by heat of the image capturing elements 7 themselves in the image capturing elements 7. Further, electric current caused by the dark electric charge leaks to the bias line 9 and accumulated in the connection 10. Therefore, a small amount of electric current flows in the connection 10 even when radiation is not irradiated to the radiation image capturing apparatus 1, and the voltage value Va corresponding to the electric current is outputted from the electric current detection unit 42.

Moreover, the configuration may be such that a threshold value $\Delta$Vth is set for the change rate $\Delta$V of the voltage value V, for example, instead of setting the threshold Vth for the voltage value V itself in order to detect starting and finishing of radiation irradiation, and detecting the time when the rate of increase of the voltage value V exceeded the threshold $\Delta$Vth as the starting time "t start" of radiation irradiation and detecting the time when the absolute value of the rate of decrease $\Delta$V of the voltage value V be equal to or greater than the threshold value $\Delta$Vth as the finishing time "t end" of radiation irradiation.

Further, for example, by integrating the voltage values V which are outputted from the electric current detection unit 42 during the time between the start time "t start" of radiation irradiation and the finish time "t end" of radiation irradiation to convert into the corresponding current value, the amount of radiation irradiated to the radiation image capturing apparatus 1 can be estimated.

Furthermore, by configuring so as to hold the peak value of the voltage value V which is outputted from the electric current detection unit 42 and by calculating the product of the maximum value Vp and the time interval between the start time "t start" of radiation irradiation and the finish time "t end" of radiation irradiation, the total amount of the voltage V can be estimated by making the trapezoidal shape transition of the voltage value V shown in FIG. 11 be close to a rectangular shape, and based on the estimation, the amount of radiation irradiated to the radiation image capturing apparatus 1 can be estimated.

In the embodiment, when the control unit 22 detects that the radiation irradiation is started by detecting the increase in the voltage value V which corresponds to the current value outputted from the electric current detection unit 42 by the current amount of the current that flows in the connection 10 of the bias line 9 increase as described above, the control unit 22 makes the reading circuits 17 be in the power supply mode from the waiting mode and switches the power consumption mode of the radiation image capturing apparatus 1 to the third mode "mode 3" (electric charge accumulating state) from the second mode "mode 2" (waiting for irradiation state".

As shown in FIG. 10, in the third mode "mode 3", applying of the reverse bias voltage to each of the image capturing elements 7 from the reverse bias power source 14 is continued and ON/OFF of each TFT 8 is switched as needed. Further, current is applied to each of the reading circuits 17 and the charge amplifier circuit which constitutes the amplifier circuit 18 is made to be in the operating state, and the mode switching switch 24 is made to be in the OFF state and the reading circuits 17 are made to be in the power supply mode from the waiting mode. In such way, in the third mode "mode 3", the power consumption increases to 8.8 [W], for example, as shown in the table of FIG. 10.

Moreover, when the radiation irradiation to the radiation image capturing apparatus 1 is ended, the reading process of reading out the electric charge which is generated and accumulated in each of the image capturing elements 7 by the radiation irradiation to convert into electric signal starts. Here, in the table of FIG. 10, the power consumption mode of the radiation image capturing apparatus 1 is made to switch to the fourth mode "mode 4" (reading state) from the third mode "mode 3" (electric charge accumulating state) by the reading process being started. However, the accumulation of the electric charge (the third mode "mode 3") and the reading out of the electric charge (the fourth mode "mode 4") of the image capturing elements 7 are a series of process in the radiation image capturing apparatus 1.

Furthermore, when the reading process is started as described above (the fourth mode "mode 4" in the table of FIG. 10), various parts of the reading circuits 17 such as the amplifier circuit 18, the correlated double sampling circuit 19, the analog multiplexer 21, the A/D converter 20, the scan activation circuit 15 and the like start to operate. Therefore, the power consumption increases even more to 13.6 [W], for example.

In the reading process, there is no need to detect the electric current that flows in the connection 10 of the bias lines 9. Therefore, the switch of the electric current detection unit 42 is made to be in the ON state and between the terminals of the resistance of the electric current detection unit 42 is shunted. Further, the ON voltage for signal reading is applied to the scanning line 5 of the first line from the scan activation circuit 15 and the TFT 8 connected to the scanning line 5 is made to be in the ON state, and further, the electric charge (in case of the embodiment, electrons) is released to the signal line 6 from each of the image capturing elements 7 via the TFT 8.

The charging/voltage conversion, amplifying and the like are carried out to the electric charges that flown to the signal lines 6 in the reading circuits 17 to be converted into electric signals and are transmitted to the A/D converter 20 in order via the analog multiplexer 21 to be converted into digital values and to be stored in the storage unit 23 in order. Further, the scan activation circuit 15 switches the voltage to be applied to the scanning line 5 of the first line to the OFF voltage and makes each TFT 8 be in the OFF state, and thereafter, the scan activation circuit 15 switches the line of the scanning lines 5 to which the ON voltage for signal reading is to be applied in order to make the electric charge be released from each of the image capturing elements 7.

In such way, by the electric charges which are read from the image capturing elements 7 being converted into electric signals in order and being stored in the storage unit 23 in order, the reading process of the electric signals from the image capturing element 7 is carried out.

As described above, according to the radiation image capturing apparatus 1 of the embodiment, the control unit 22 detects that the radiation irradiation is started by detecting the increase in the current amount (or the corresponding voltage value V) of the current that flows in the bias lines 9 and the connection 10 detected by the electric current detection unit 42. Further, when the starting of the radiation irradiation is detected, the control unit 22 makes the reading circuits 17 be in the normal power supply mode from the waiting mode in which power consumption is small.

Therefore, the reading circuits 17 are made to switch to the power supply mode from the waiting mode when the reading process is to be carried out right after the radiation is irradiated to the radiation image capturing apparatus 1 radiation image capturing apparatus 1. Therefore, the time period for the reading circuits 17 to be in the power supply mode in which the power consumption is greater comparing to being in the waiting mode can be inhibited from being unnecessarily long. Thus, the amount of power consumption at the time of radiation image capturing can be reduced and the consumption rate of the battery can be reduced.

Furthermore, in the radiation image capturing apparatus 1 of the embodiment, the control unit 22 itself detects that the radiation irradiation is started. Therefore, there is no need to control so as to have interface with the radiation image capturing apparatus. Thus, even when the radiation generation apparatus and the radiation image capturing apparatus 1 are manufactured by different manufacturers, for example the starting of radiation irradiation can be detected easily and accurately in the radiation image capturing apparatus 1 itself and the mode of the reading circuits 17 can be switched.

Here, in the embodiment, the case where the mode switching switch 24 for joining the inverting input terminal 18a1 and the non-inverting input terminal 18a2 of each of the operational amplifier 18a of the amplifier circuits 18 of the reading circuits 17 are provided (see FIG. 8) and where the waiting mode and the power supply mode of the reading circuits 17 are switched therebetween by the switching of the operation state/non-operation state of the charge amplifier circuit which constituted the amplifier circuit 18 and the ON/OFF of the mode switching switch 24 is described as above.

However, the configuration may be such that the above mentioned closed loop is formed by using the characteristic of the charge amplifier circuit which constituted the amplifier circuit 18, for example, instead of providing the mode switching switch 24 for joining the inverting input terminal 18a1 and the non-inverting input terminal 18a2 of the operational amplifier 18a.

For example, there is a case where the operation amplifier 18a of the amplifier circuit 18 is configured so as to be switched between the state where the electric current that flow in the operational amplifier 18a be a high current and the state of low current where the low operation current which is smaller than the above high current flows when the operational amplifier 18a is in the normal operating state of carrying out the charging/voltage conversion and amplifying to the electric charge for each image capturing element 7 when the reading circuits 17 are in the power supply mode. In such operational amplifier 18a, when the switch 18c for resetting the electric charge which is connected parallely to the operational amplifier 18a is made to be in the ON state, the inverting input terminal 18a1 and the non-inverting input terminal 18a2 be the same potential and be virtually grounded.

In view of the above, by using this characteristic of the operational amplifier 18a, when the control unit 22 (see FIG. 8) makes the reading circuits 17 switch to the waiting mode, the control unit 22 switches the operational amplifier 18a of the amplifier circuit 18 so the current that flows therein be low current and also makes the switch 18c for resetting the electric charge be in the ON state and makes the inverting input terminal 18a1 and the non-inverting input terminal 18a2 of the operational amplifier 18a be virtually grounded to form the above mentioned closed loop.

Furthermore, when the control unit 22 makes the reading circuits 17 switch to the power supply mode, the control unit 22 switches the operational amplifier 18a of the amplifier circuit 18 be in a state where the current that flows therein be in a high current. At this time, ON/OFF of the switch 18c for resetting the electric charge is to be switched as needed.

In the case of the above configuration, power needs to be supplied so that low current flows in the operational amplifier 18a of the amplifier circuit 18 of the reading circuits 17 even when the reading circuits 17 are in the waiting mode. However, comparing to the reading circuits 17 being in the power supply mode in which current is applied to the reading circuits 17 and the operation amplifiers 18a are made to be in the state where a high current flows therein, the power consumption can be small and the advantages similar to the case of the above embodiment can be obtained.

Here, in the embodiment, the case where the electric current detection unit 42 is provided to the connection 10 of the bias lines 9 is described. However, the electric current detection unit 42 can detect the current which flows in the radiation image capturing apparatus 1 by the radiation irradiation as described above, the electric current detection unit 42 does not need to be provided to the connection 10 of the bias lines 9 as long as the control unit 22 can detect the starting of radiation irradiation or the like based on the current amount of the electric current.

As described above, when radiation is irradiated to the radiation image capturing apparatus 1 and the radiation is converted into electromagnetic wave in the scintillator 3 and the electromagnetic enters the image capturing elements 7, the electron-hole pairs are generated in the image capturing elements 7. In the embodiment, the electrons are accumulated near the first electrode 74 of each of the image capturing elements 7 and the holes are accumulated near the second electrode 78. Further, in the embodiment, the current of when the holes that leak from the second electrode 78 side of each of the image capturing elements 7 flow in the connection 10 of the bias lines 9 is to be detected by the electric current detection unit 42.

However, when the holes leak from the second electrode 78 side of each of the image capturing element 7, electrons in the same amount as the holes leak to each of the signal lines 6 from the first electrode 74 side of each of the image capturing element 7 via the TFT 8 at the same time. Thousands of image capturing elements 7 are connected to one signal line 6 via the TFT 8 and the electric current due to the electrons leaked form the image capturing elements 7 reaches the level that can be detected by the electric current detection unit.

Therefore, by configuring so as to detect the electric current that flow in one or a predetermined number of signal lines 6 by the electric current detection unit, the electric current is due to the electrons leak from the first electrode 74 side of each of the image capturing elements 7, the electric current (or the corresponding voltage value V) which flows in the signal line 6 according to starting and ending of radiation irradiation is detected by the electric current detection unit as shown in FIG. 11. Thus, the control unit 22 can detect the starting of radiation irradiation or the like based on the current amount of the electric current that flows in the signal line which is detected by the electric current detection unit.

On the other hand, the electric current detection unit can be configured to detect the electric current that flows in the scanning lines 5 or the scan activation circuit 15. Hereinafter, such case will be described.

As described above, in the embodiment, when it is instructed to switch the mode of the radiation image capturing apparatus 1 by an manual operation of an operator such as a radiation technologist or the like or by receiving a signal from an external device at the time of radiation image capturing, the power consumption mode of the radiation image capturing apparatus 1 is switched to the second mode "mode 2" (waiting for irradiation state) and the reserve bias voltage is applied to each of the image capturing elements 7 from the reverse bias power source 14 by the control unit 22 (see FIG. 10). Further, at the same time, each TFT 8 is made to be in the OFF state, therefore, a potential difference which is the reverse bias voltage occurs between the first electrode 74 and the second electrode 78 of each of the image capturing elements 7 at that time (see FIG. 8).

Further, as described above, when the electron-hole pairs are generated in each of the image capturing elements 7 by radiation being irradiated at the time of radiation image capturing, the potential of the first electrode 74 with respect to the second electrode 78 changes according to the amount of the electron-hole pairs generated.

That is, in the embodiment, the reverse bias voltage of a predetermined minus value is applied to the second electrode 78 from the bias power source 14 via the bias line 9 and the potential is fixed. The holes among the electron-hole pairs that are generated in the image capturing element 7 move to the second electrode 78 side and the electros among the electron-hole pairs move to the first electrode 74 side. Therefore, the potential at the first electrode 74 side is reduced. Further, as the potential at the first electrode 74 side of the image capturing element 7 is reduced, the potential at the source electrode 8s (indicated as S in FIG. 8) side of the TFT 8 shown in FIG. 8 is reduced.

Furthermore, at the TFT 8, a type of condensor is formed by the gate electrode 8g, the source electrode 8s and the insulating layer 71 (see FIG. 5) between the gate electrode 8g and the source electrode 8s, and there is a parasitic capacitance between the gate electrode 8g and the source electrode 8s. Further, a predetermined OFF voltage is applied to the gate electrode 8g of the TFT 8 and the potential does not change.

When the potential of the source electrode 8s side of the TFT 8 is reduced with respect to the gate electrode 8g of the TFT 8 in which the potential does not change, the potential difference between the gate electrode 8g and the source electrode 8s of the TFT 8 changes. Therefore, the electric charge corresponding to the changed potential difference is supplied to the gate electrode 8g of the TFT 8 through the scanning line 5. That is, electric current flows through the scanning line 5.

Thousands of TFT 8 are connected to one scanning line 5 and the electric current due to the electrons that leak from the thousands of TFT 8 reaches the level that can be detected by the electric current detection unit. Therefore, for example, by configuring so as to detect the electric current that flows in one of a predetermined number of scanning lines 5, the electrode current being due to the electric change supplied to the gate electrode 8g of each TFT 8, by the electric current detection unit, the electric current (or the corresponding voltage value V) that flows through the scanning lines 5 according to starting or ending of radiation irradiation is to be detected as shown in FIG. 11 by the electric current detection unit. Thus, the starting of radiation irradiation or the like can be detected by the control unit 22 based on the current amount of the electric current that flows through the scanning line 5 which is detected by the electric current detection unit.

Figure 12:
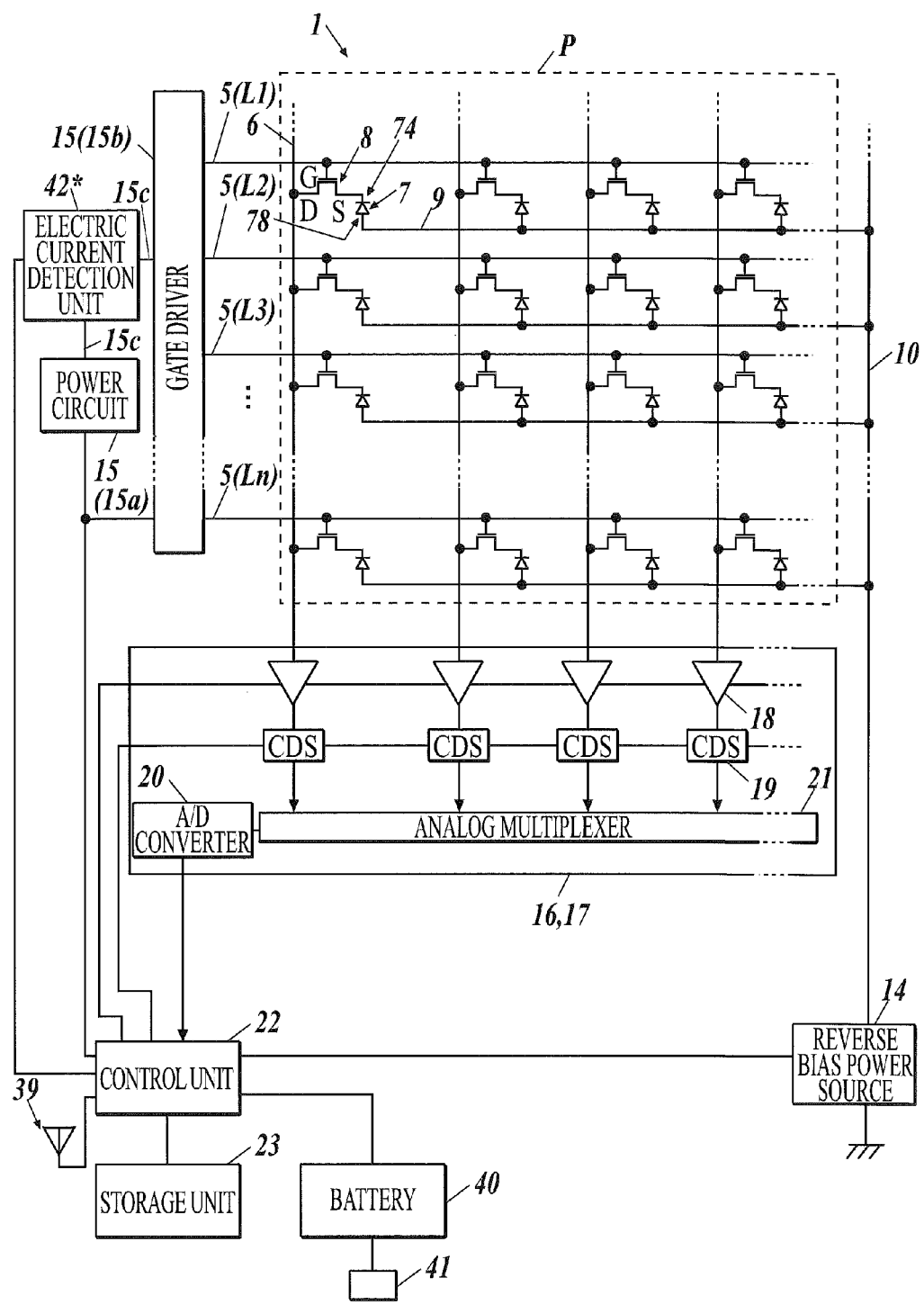
FIG. 12 This is a diagram showing an equivalent circuit schematic of the radiation image capturing apparatus when the position of the electric current detection unit is changed.

Moreover, in a case where it is configured that the scan activation circuit 15 (see FIG. 7) includes the gate driver 15b which applies the ON voltage or OFF voltage to the gate electrode 8g of each TFT 8 via each of lines L1 to Ln which are the scanning lines 5 and the power circuit 15a which supplies the ON voltage or the OFF voltage to the gate driver 15b as shown in FIG. 12, for example, when electric current flows through each of the scanning line 5 in a state where the OFF voltage is being applied to each of the lines L1 to Ln which are the scanning lines 5, the electric current flows in the wiring 15c which joins the power circuit 15a and the gate driver 15b after all.

Therefore, for example, by configuring so as to provided the electric current detection unit 42* on the wiring 15c which joins the power circuit 15a and the gate driver 15b of the scan activation circuit 15 and to detect the electric current that flows between the power circuit 15a and the gate driver 15b by the electric current detection unit 42*, the electric current (or the corresponding voltage value V) that flows through the wiring 15c according to starting or ending of radiation irradiation is detected as shown in FIG. 11 by the electric current detection unit 42*. Thus, starting of radiation irradiation or the like can be detected by the control unit 22 based on the current amount of the electric current that flows through the scanning line 5 which is detected by the electric current detection unit.

Second Embodiment

Next, the radiation image capturing system 100 according to the second embodiment of the present invention which carries out radiation image capturing by using the above radiation image capturing apparatus 1 will be described.

Figure 13:
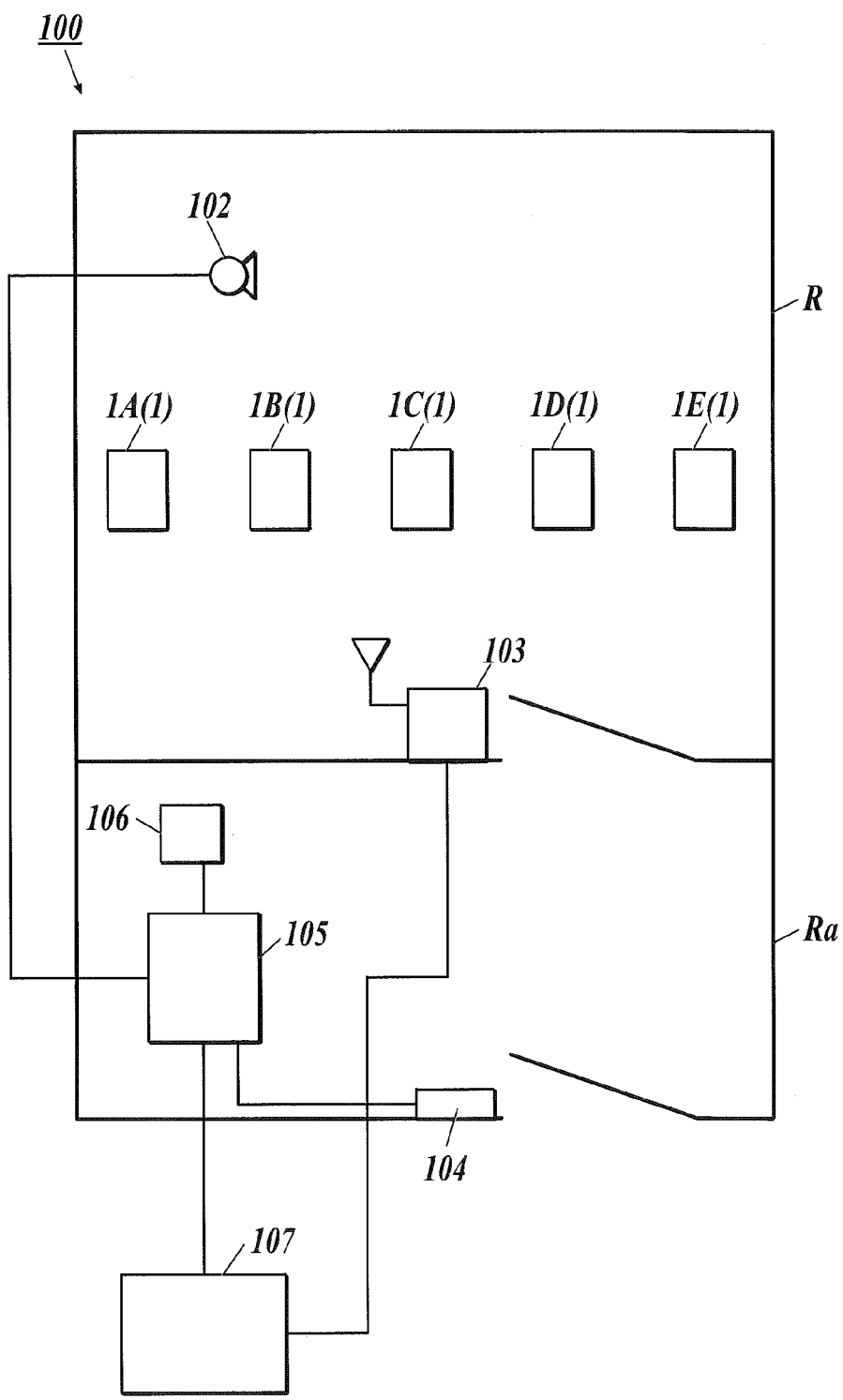
FIG. 13 This is a diagram showing an overall configuration of a radiation image capturing system according to the second embodiment.

The radiation image capturing system 100 of the embodiment is a system assuming the radiation image capturing carried out in a hospital or a clinic. As shown in FIG. 13, the radiation image capturing system 100 includes an image capturing room R in which image capturing of a target body (a part of a patient which is targeted for image capturing) which is a part of a patient is carried out by irradiating radiation, a front room Ra where a radiation technologist, a doctor or the like (hereinafter, called an operator) carries out various types of operation such as control of radiation to be irradiated to the target body and the like and a console 107 which carries out a control of the entire radiation image capturing system 100, for example.

In the image capturing room R, for example, five of the above described radiation image capturing apparatuses 1 are disposed. Hereinafter, the radiation image capturing apparatuses will be respectively indicated as the radiation image capturing apparatus 1A to 1E when individually identifying them, and the radiation image capturing apparatus 1A to 1E will be indicated as the radiation image capturing apparatus 1 collectively when there is no need to individually identifying them.

Further, the image capturing room R includes a bucky 101 (see FIG. 14) in which the radiation image capturing apparatus 1 can be mounted, a radiation generation device 102 which emits radiation to the target body, a wireless access point 103 which relays communication between the radiation image capturing apparatuses 1 and the console 107 and the like. The image capturing room is sealed off by lead or the like so that the radiation does not leak outside.

Further, the front room Ra includes a tag reader 104 for detected the after-mentioned tags which are embedded in the radiation image capturing apparatus 1 and an operation table 105 for controlling the radiation irradiation by the radiation generation device 102.

Here, the number of each of the devices such as the radiation image capturing apparatus 1, the radiation generation device 102 and the like disposed in the image capturing room and the front room Ra is an example, and the number of each of the devices to be disposed is not limited to the examples shown in the drawings.

Hereinafter, the radiation image capturing apparatuses 1, the bucky 101, the radiation generation device 102, the wireless access point 103, the tag reader 104, the operation table 105 and the console 107 which are included in the radiation image capturing system 100 of the embodiment will be described in detail.

(Radiation Image Capturing Apparatus 1)

The configuration of the radiation image capturing apparatus 1 is as described above. However, the radiation image capturing apparatus 1 further includes the following configuration in the radiation image capturing system 100 of the embodiment.

In particular, a cassette ID is assigned to each of the radiation image capturing apparatuses 1A to 1E in advance as identification information to specify each radiation image capturing apparatus 1. For example, the cassette ID "1001" is assigned to the radiation image capturing apparatus 1A, the cassette ID "1002" is assigned to the radiation image capturing apparatus 1B, the cassette ID "1003" is assigned to the radiation image capturing apparatus 1C, the cassette ID "1004" is assigned to radiation image capturing apparatus 1D and the cassette ID "1005" is assigned to the radiation image capturing apparatus 1E.

Further, a tag which is not shown in the drawing is embedded in each of the radiation image capturing apparatuses 1. In the embodiment, a tag so-called RFID (Radio Frequency Identification) tag is used as the tag, and a control circuit to control each part of the tag and a storage unit to store information unique to the radiation image capturing apparatus 1 are embedded in the tag compactly. The information unique to the radiation image capturing apparatus 1 includes the cassette ID which is assigned to the radiation image capturing apparatus 1 itself, type information of the scintillator, size information, resolution level and the like.

Furthermore, in the embodiment, the radiation image capturing apparatus 1 is configured in a size which complies with JIS Z 4905 (the corresponding international standard is IEC 60406) of the conventional cassette for screen/film. That is, the thickness thereof in the radiation incidence direction is within the range of 15 mm+1 mm to 15 mm−2 mm, and the radiation image capturing apparatuses 1 having sizes of 8 inch×10 inch, 10 inch×12 inch, 11 inch×14 inch, 14 inch×14 inch, 14 inch×17 inch (half size) and the like are prepared.

As described above, because the radiation image capturing apparatus 1 complies with the JIS standard regarding the cassette for screen/film, the CR cassette which is similarly formed in compliance with the JIS standard can be used by being mounted to the bucky 10 in the facility where the CR cassette can be mounted.

Here, the radiation image capturing apparatuses 1 can be used by itself without being mounted on the bucky 101. That is, the radiation image capturing apparatuses 1 can be used by arranging the radiation image capturing apparatus 1 to the supporting platform or the bucky for recumbent position image capturing (both of which are not shown in the drawing) which are provided in the image capturing room R by itself, for example, and placing a hand or the like of a patient which is the target body on the radiation incidence surface R (see FIG. 1) or by placing the radiation image capturing apparatus 1 between the hip or a leg of the patient who is in a recumbent position on the bed and the bed.

In the embodiment, the radiation image capturing apparatuses 1 are connected with the console 107 via the antenna device 39 and the wireless access point 103 as the communication unit, and the radiation image capturing apparatuses 1 can send and receive various types of control signals and data with the console 107 by the wireless communication.

Here, although the description overlaps the above description, the flow of switching of the power consumption mode carried out in the radiation image capturing apparatuses 1 at the time of radiation image capturing will be described.

The radiation image capturing apparatuses 1 are disposed in the image capturing room R in the state where the power consumption mode is switched to the first mode "mode 1" (sleep mode). As described above, the first mode "mode 1" (sleep mode) is a mode in which power is supplied only to the necessary units such as the control unit 22, the storage unit 23, the antenna device 39 and the like and power is not supplied to the reading circuits 17, the image capturing elements 7, the TFT 8 and the like.

Further, when the control unit 22 of the radiation image capturing apparatus 1 receives the second mode switching signal which instructs to switch to the second mode "mode 2" (waiting for irradiation state) from the console 107 in the state of being switched to the first mode "mode 1" (sleep state), the control unit 22 starts to apply the reverse bias voltage to the image capturing elements 7 and makes the mode switching switch 24 be in the ON state to switch the reading circuits 17 be in the power supply mode from the waiting mode and to switch the power consumption mode of the radiation image capturing apparatus 1 to the second mode "mode 2" (waiting for irradiation state) from the first mode "mode 1" (sleep state).

As described above, the second mode "mode 2" (waiting for irradiation state) is the mode where starting of radiation irradiation to the radiation image capturing apparatus 1 can be detected based on the voltage value V outputted from the electric current detection unit 42 according to the current amount of the electric current that flows in the connection 10 of the bias lines 9.

Here, in the radiation image capturing system 100 of the present invention, the configuration in which it is determined that radiation irradiation to the radiation image capturing apparatus 1 is started at the time "t start" when the voltage value V outputted from the electric current detection unit 42 exceeded the threshold value Vth and it is determined that the radiation irradiation to the radiation image capturing apparatus 1 is ended at the time "t end" when the voltage value V outputted from the electric current detection unit 42 be equal to or smaller than the threshold value Vth will be described. However, as described above, the configuration may be such that starting and ending of the radiation irradiation is detected based on the change rate ΔV of the voltage value V outputted from the electric current detection unit 42 or the estimated value of the total amount of the voltage value V outputted from the electric current detection unit 42.

When the radiation image capturing apparatus 1 is switched to the second mode "mode 2" (waiting for irradiation state) according to the second mode switching signal from the console 107, as described above, the control unit 22 of the radiation image capturing apparatus 1 monitors the voltage value V outputted from the electric current detection unit 42 and detects the starting of radiation irradiation to the radiation image capturing apparatus 1 by determining whether the voltage value V outputted from the electric detection unit 42 exceeded the threshold value Vth or not.

When the control unit 22 of the radiation image capturing apparatus 1 detects that the radiation irradiation started in the state of being switched to the second mode "mode 2" (waiting for irradiation state), the control unit 22 switches the reading circuits 17 to the power supply mode from the waiting mode and switches the power consumption mode of the radiation image capturing apparatus 1 to the third mode "mode 3" (electric charge accumulating state) from the second mode "mode 2" (waiting for irradiation state).

In the third mode "mode 3" (electric charge accumulating state), as described above, the reverse bias voltage is applied to the image capturing elements 7 and power is supplied to the reading circuits 17, and electric charge is generated in the image capturing elements 7 by the radiation irradiation and the electric charge according to the amount of radiation irradiated is accumulated in each of the image capturing elements 7.

Further, after being switched to the third mode "mode 3" (electric charge accumulating state), the control unit 22 of the radiation image capturing apparatus 1 monitors the voltage value V outputted from the electric current detection unit 42 and detects that the radiation irradiation to the radiation image capturing apparatus 1 is ended by determining whether the voltage value V outputted from the electric current detection unit 42 is equal to or smaller than the threshold value Vth or not.

Here, it may be determined that the radiation irradiation is ended assuming that the radiation irradiation is ended after a predetermined time period elapsed since the starting of the radiation irradiation.

When the ending of the radiation irradiation is detected in a state where the radiation image capturing apparatus 1 is switched to the third mode "mode 3" (electric charge accumulating state), the control unit 22 switches the power consumption mode of the radiation image capturing apparatus 1 to the fourth mode "mode 4" (reading state) from the third mode "mode 3" (electric charge accumulating state) and executes the reading process of reading out the electric charge accumulated in the image capturing elements 7 and converts the electric charge to electric signals. In the reading process, the electric charge accumulated in each of the image capturing elements 7 by the radiation irradiation is converted to an electric signal and stored in the storage unit 23.

The radiation image capturing apparatus 1 which finished the reading process of reading out the electric charge accumulated in each of the image capturing elements 7 carries out various types of correction processes such as the off set/gain correction, the defect correction and the like to the data stored in the storage unit 23 as needed to generated image data (raw data), and generates thinned image data in which the data amount is reduced by thinning the pixels (that is, data outputted from each of the image capturing elements 7) in the generated image data at a predetermined rate. Then, the radiation image capturing apparatus 1 transmits the generated thinned image data to the console 107 via the antenna device 39 and the wireless access point 103. At this time, by the radiation image capturing apparatus 1 transmitting the thinned image data by making the cassette ID which is assigned to itself correspond to the thinned image data, the cassette ID of the radiation image capturing apparatus 1 itself is notified to the console 107.

Further, when the radiation image capturing apparatus 1 receives the instruction signal for requesting the transmission of the original image data (raw data) of the thinned image data from the console 107 via the wireless access point 103 and the antenna device 39, the radiation image capturing apparatus 1 reads out the original image data of the thinned image data from the storage unit 23 to transmit to the console 107 via the antenna device 39 and the wireless access point 103.

After the original image data is transmitted to the console 107, the control unit 22 of the radiation image capturing apparatus 1 switches the power consumption mode of the apparatus to the first mode "mode 1" (sleep mode).

Here, in the image capturing carried out in one image capturing room R except when carrying out image forming of subtraction system, two or more of the radiation image capturing apparatuses 1 will not be used at one radiation image capturing. That is, most of the time, the radiation image capturing is executed by using one radiation image capturing apparatus 1 and the radiation irradiation is carried out to only one radiation image capturing apparatus 1.

Therefore, in one radiation image capturing, there is only one radiation image capturing apparatus 1 that detects radiation irradiation in one image capturing room R, and other radiation image capturing apparatuses 1 which are in the same image capturing room R do not detect radiation irradiation. Further, the console 107 receives image data only from the one radiation image capturing apparatus 1 which detected radiation irradiation.

As will be described later, the cassette ID of each of the radiation image capturing apparatuses 1 in the image capturing room R is read by the tag reader 104 and is notified to the console 107, and the console 107 recognizes each of the radiation image capturing apparatuses 1 that exist in the image capturing room R. Further, when the radiation image capturing apparatus 1 which detected the radiation irradiation transmits the thinned image data along with its own cassette ID to the console 107, the console 107 determines that the radiation image capturing apparatuses 1 having cassette IDs other than the cassette ID which is notified along with the image data as the radiation image capturing apparatuses 1 not being used for the image capturing, and transmits the first mode switching signal which instructs to switch the power consumption mode to the first mode "mode 1" (sleep state) to the radiation image capturing apparatuses 1 which are not used for the image capturing. Then, the radiation image capturing apparatuses 1 which are not used for the image capturing switch their power consumption mode to the first mode "mode 1" (sleep mode) from the second mode "mode 2" (waiting for irradiation state) based on the first mode switching signal which is transmitted from the console 107.

Here, the configuration may be such that the content of various types of correction processes such as the off set/gain correction, the defect correction and the like is made to correspond to the cassette ID of each of the radiation image capturing apparatuses 1 in advance to be stored in the console 107 and the correction processes (that is, the correction processes which are made to correspond to the radiation image capturing apparatus 1 used for the image capturing) which are made to correspond to the cassette ID are carried out in the console 107 side based on the cassette ID notified from the radiation image capturing apparatus 1 which detected the radiation irradiation along with the thinned image data.

(Bucky 101)

Figure 14:
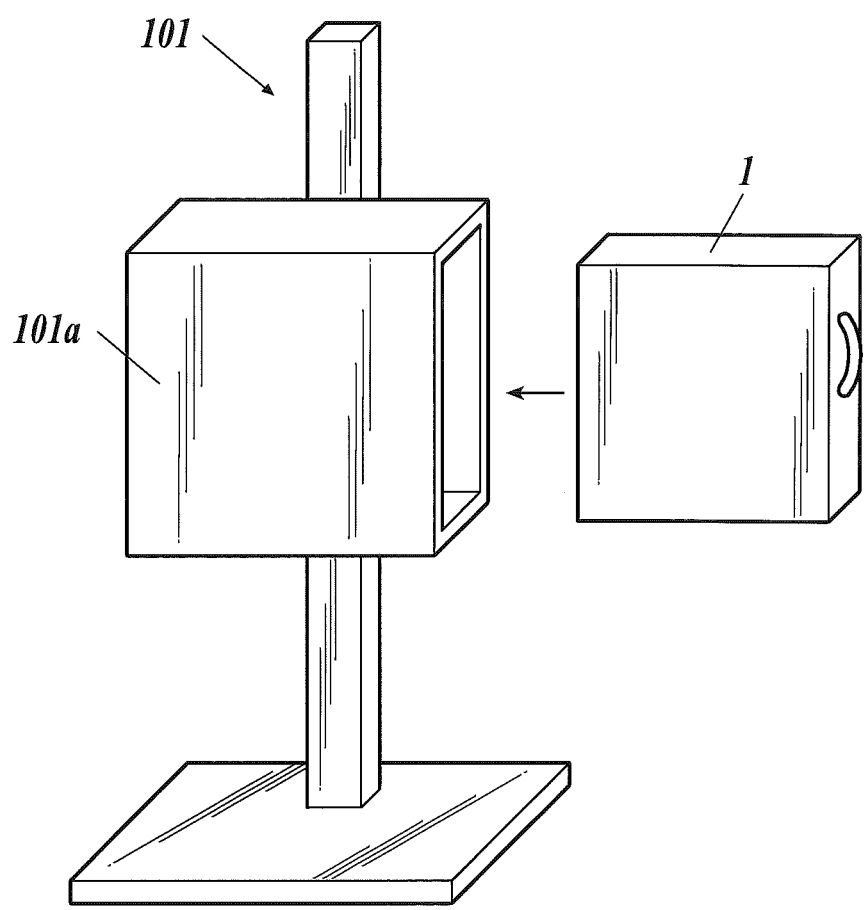
FIG. 14 This is a diagram explaining a bucky including a cassette holding unit and a radiation image capturing apparatus which is to be loaded in the bucky.

As shown in FIG. 14, a cassette holding unit 101*a* for holding the radiation image capturing apparatus 1 at a predetermined position is provided at the bucky 101, and the radiation image capturing apparatus 1 can be mounted to the cassette holding unit 101a. Further, the image capturing room R includes a bucky for recumbent position image capturing (not shown in the drawing) other than the bucky 101 for standing position image capturing shown in FIG. 14.

The bucky 101 is configured so that the conventional CR cassette and FPD cassette (the radiation image capturing apparatuses 1) having the size that complies with the JIS standard of cassette for screen/film can be mounted.
(Radiation Generation Device 102)

The radiation generation device 102 includes a radiation source (not shown in the drawing) which emits radiation to the radiation image capturing apparatus 1 via the target body, and the radiation source emits radiation in the amount corresponding to the voltage when a high voltage is applied. Further, each of the radiation source includes a squeeze (not shown in the drawing) which can be opened and closed freely.

In FIG. 13, only one radiation generation device 102 is shown. However, a plurality of radiation generation devices 102 may be provided to be disposed so that the plurality of radiation generation devices 102 respectively correspond with a plurality of bucky 101. Further, a portable radiation generation device which can be carried to arbitrary places in the image capturing room R and can irradiate radiation in arbitrary directions may be provided.
(Wireless Access Point 103)

The wireless access point 103 relays the communication between the radiation image capturing apparatuses 1 and the console 107. In FIG. 13, the wireless access point is disposed near the entrance of the image capturing room R. However, the number and the disposing position of the wire access point 103 are not limited to the above as long as the wireless access point 103 is disposed at an arbitrary position where the wireless access point can relay the signals between the radiation image capturing apparatuses 1 and the console 107.
(Tag Reader 104)

The tag reader 104 sends out a signal by including a predetermined instruction information in an electric wave or the like via an embedded antenna (not shown in the drawing) and detects the radiation image capturing apparatus 1 which enters or leaves the image capturing room R, that is, the radiation image capturing apparatus 1 which entered a predetermined range of the image capturing room R and the front room Ra. Then, the tag reader 104 reads the information unique to the detected radiation image capturing apparatus 1 stored in the RFID tag thereof, such as the cassette ID, the type information of the scintillator, the size information, the resolution level and the like and transmits the read information unique to the detected radiation image capturing apparatus 1 to the console 107.
(Operation Table 105)

The operation table 105 is configured of a computer including a generalized CPU, a computer including a specialized processor or the like. The operation table 105 is connected to the radiation generation device 102 by a cable or the like and is connected to the console 107 via a cable or the like, and the operation table 105 is configured so as to set the irradiation condition by obtaining image capturing position information and the like from the console 107.

The operation table 105 includes a switch 106 or the like for instructing to start irradiation of radiation from the radiation generation device 102. The switch 106 has a button (not shown in the drawing), and when the button is operated, an activation signal is transmitted from the operation table 105 to the radiation generation device 102 and the radiation source of the radiation generation device 102 is activated by the activation signal.
(Console 107)

Figure 15:
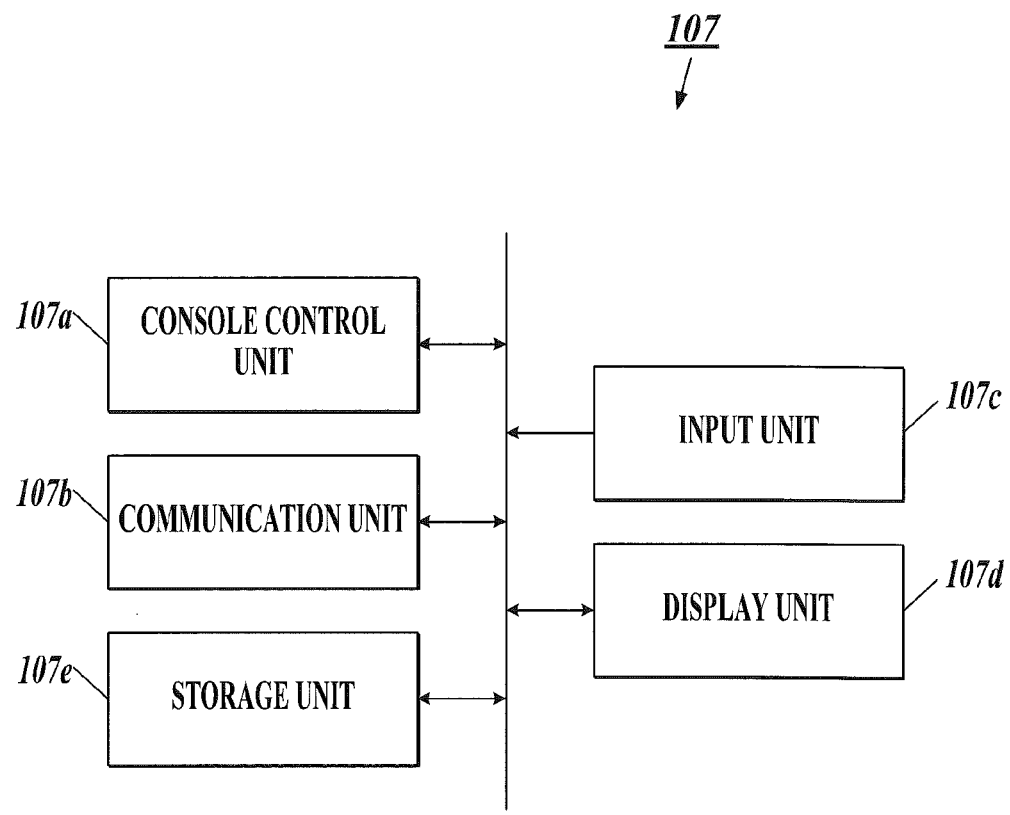
FIG. 15 This is a block diagram showing a functional configuration of a console.

As shown in FIG. 15, the console 107 includes a console control unit 107a, a communication unit 107b, an input unit 107c, a display unit 107d and a storage unit 107e.

For example, the console control unit 107a is constituted of a generalized CPU, a ROM (Read Only Memory), a RAM and the like (all of which are not shown in the drawing), and the console control unit 107a reads out a predetermined program stored in the ROM and expands the program in the working area of the RAM and the CPU executes various types of processes according to the program.

The communication unit 107b is for carrying out communication with the radiation image capturing apparatuses radiation image capturing apparatuses 1 via the wireless access point 103, and the communication unit 107b carries out sending and receiving various types of control signals, data and the like with the radiation image capturing apparatuses 1.

The input unit 107c is constituted of a key board, a mouse and the like for inputting various types of instructions and information, and the input unit 107c is operated when an operator sets information of a patient who is target for the radiation image capturing and an image capturing condition before the radiation image capturing. As will be described later, the patient information and the image capturing condition are set by an operator selecting and inputting the image capturing information as a predetermined information by using the input unit 107c.

The display unit 107d is formed of CRT (Cathode Ran Tube), LCD (liquid Crystal Display) or the like, and the display unit 107d displays images and various types of information such as the image capturing order information which are transmitted from the radiation image capturing apparatus 1.

The storage unit 107e is constituted of a hard disk or the like and stores various types of information.

In particular, a list of the radiation image capturing apparatuses 1 in the image capturing room R is stored in the storage unit 107e. When the information unique to the radiation image capturing apparatus 1 which is detected by the tag reader 104 disposed near the entrance of the front room Ra including the cassette ID of the radiation image capturing apparatus 1 is transmitted to the console 107 as described above, the console 107 refers to the list of the radiation image capturing apparatuses 1 in the image capturing room R, which is registered in the storage unit 107e.

Then, when the information unique to the radiation image capturing apparatus 1 which is transmitted is not registered in the storage unit 107e, the console 107 determines that the radiation image capturing apparatus 1 is newly brought into the image capturing room R and adds the cassette ID and the like of the radiation image capturing apparatus 1 to the above mentioned list and stores in the storage unit 107e.

Further, when the information unique to the radiation image capturing apparatus 1 which is transmitted is already registered in the storage unit 107e, the console 107 determines that the radiation image capturing apparatus 1 was taken out from the image capturing room R and deletes the cassette ID and the like of the radiation image capturing apparatus 1 from the list.

In such way, the console 107 stores the cassettes IDs and the like of the radiation image capturing apparatuses 1 in the image capturing room R in the storage unit 107e and recognizes which of the radiation image capturing apparatuses 1 are in the image capturing room R.

Furthermore, the image capturing order information including the information of a patient who is target for the radiation image capturing to be carried out in the image capturing room R and the image capturing condition is stored in the storage unit 107e. The image capturing order information is to be stored in the storage unit 107e in advance in a list form before the radiation image capturing.

In the embodiment, as shown in FIG. 16, the image capturing order information includes "patient ID" P2, "patient name" P3, "gender" P4 and "age" P5 as the patient information and "image capturing part" P6 and "image capturing direction" P7 as the image capturing condition. Further, "image capturing order ID" P1 is automatically assigned to the image capturing information in the order of acceptance of the image capturing order.

Here, contents of the patient information and the image capturing condition to be written in the image capturing order information are not limited to the above, and for example, information such as the birth date of the patient, the number of times of examinations, the amount of radiation, whether the patient is fat or thin can be included, and the contents can be set arbitrarily. Further, for example, the console 107 can be connected to HIS (Hospital Information System) and RIS (Radiology Information System) (both are not shown in the drawing) via a network and the image capturing order information may be obtained from HIS or RIS.

Furthermore, the image data received from the radiation image capturing apparatus 1 is to be stored in the storage unit 107e by being corresponded with the image capturing order information.

In addition, an imager which stores the radiation image in an image recording medium such as a film based on the image data outputted from the console 107 and outputs the radiation image is arbitrarily connected to the console 107, for example.

In the embodiment, the console 107 is made to correspond with an image capturing rooms R in advance in one-to-one correspondence, and the console 107 can communicate with all of the radiation image capturing apparatuses 1A to 1E in the image capturing room R via the communication unit 107b, the wireless access point 103 and the like. Here, when there are a plurality of image capturing room R with respect to one console 107, the configuration may be such that an operator specifies any one of the image capturing room R before the image capturing to make the specified image capturing room R correspond with the console 107 in one-to-one correspondence.

Then, when image capturing order information is selected and inputted by the input unit 107c, the consoled 107 transmits the second mode switching signal to the radiation image capturing apparatuses 1 which are disposed being in the image capturing room R in the first mode (sleep state) to switch the power consumption mode of all of the radiation image capturing apparatuses 1A to 1E in the image capturing room R to the second mode "mode 2" (waiting for irradiation state) from the first mode "mode 1" (sleep state).

Further, after switching all of the radiation image capturing apparatuses 1A to 1E in the image capturing room R to the second mode "mode 2" (waiting for irradiation state), the console 107 receives the thinned image data which is transmitted from any one of the radiation image capturing apparatuses 1, which detected radiation irradiation, via the wireless access point 103 and the communication unit 107b.

As described above, only one radiation image capturing apparatus 1 is used in one radiation image capturing and radiation is irradiated to the only one radiation image capturing apparatus 1. That is, the console 107 receives the image data which is transmitted from the one radiation image capturing apparatus 1 actually used for the image capturing. Further, when the console 107 receives the image data which is transmitted from the one radiation image capturing apparatus 1 actually used for the image capturing, the console 107 can recognize that all of the radiation image capturing apparatuses 1 other than the radiation image capturing apparatus 1 which transmitted the image data to the console 107 are the radiation image capturing apparatuses 1 which are not used to for the image capturing.

Furthermore, the console 107 which received the thinned image data transmitted from the radiation image capturing apparatus 1 obtains the cassette ID which is corresponded with the received thinned image data and refers to the cassette IDs of all of the radiation image capturing apparatuses 1 in the image capturing room R, which are stored in the storage unit 107e, to specify other radiation image capturing apparatuses 1 other than the radiation image capturing apparatus 1 which transmitted the thinned image data, that is, the radiation image capturing apparatuses 1 which are not used for the image capturing.

Then, after receiving the thinned image data from the radiation image capturing apparatus 1 used for the image capturing (at a predetermined timing), the console 107 transmits the first mode switching signal which instructs to switch to the first mode "mode 1" (sleep state) to the radiation image capturing apparatuses 1 in the image capturing room R other than the radiation image capturing apparatus 1 which transmitted the thinned image data via the communication unit 107b and the wireless access point 103 to make all of the radiation image capturing apparatuses 1 which are not used for the image capturing switch to the first mode "mode 1" (sleet state) from the second mode "mode 2" (waiting for irradiation state) in which radiation irradiation can be detected.

Here, when the subtraction image capturing is to be carried out in the image capturing room R, image data are to be transmitted along with cassette IDs from two radiation image capturing apparatuses 1 to the console 107. Therefore, when the selected image capturing information is for subtraction image capturing, the console 107 does no transmit the first mode switching signal right after obtaining the first image data, but the console 107 transmits the first mode switching signal which instructs to switch to the first mode "mode 1" (sleep state) to the radiation image capturing apparatuses which are not used for the image capturing after obtaining the second image data after a predetermine time period elapsed.

By having such configuration, even when the subtraction image capturing is to be executed, only the radiation image capturing apparatuses 1 which are not used for the image capturing can be made to switch to the first mode "mode 1" (sleep state) and the radiation image capturing apparatus 1 which is in use can be prevented from mistakenly be switched to the first mode "mode 1" (sleep state). The timing of transmitting the first mode switching signal from the console 107 is preferably determined according to whether an assorted information indicating that the image capturing is a subtraction image capturing is included in the selected image capturing order information or not.

Next, the operation of the radiation image capturing system 100 according to the embodiment will be described with reference to the flowchart of FIGS. 17 and 18.

Figure 17:
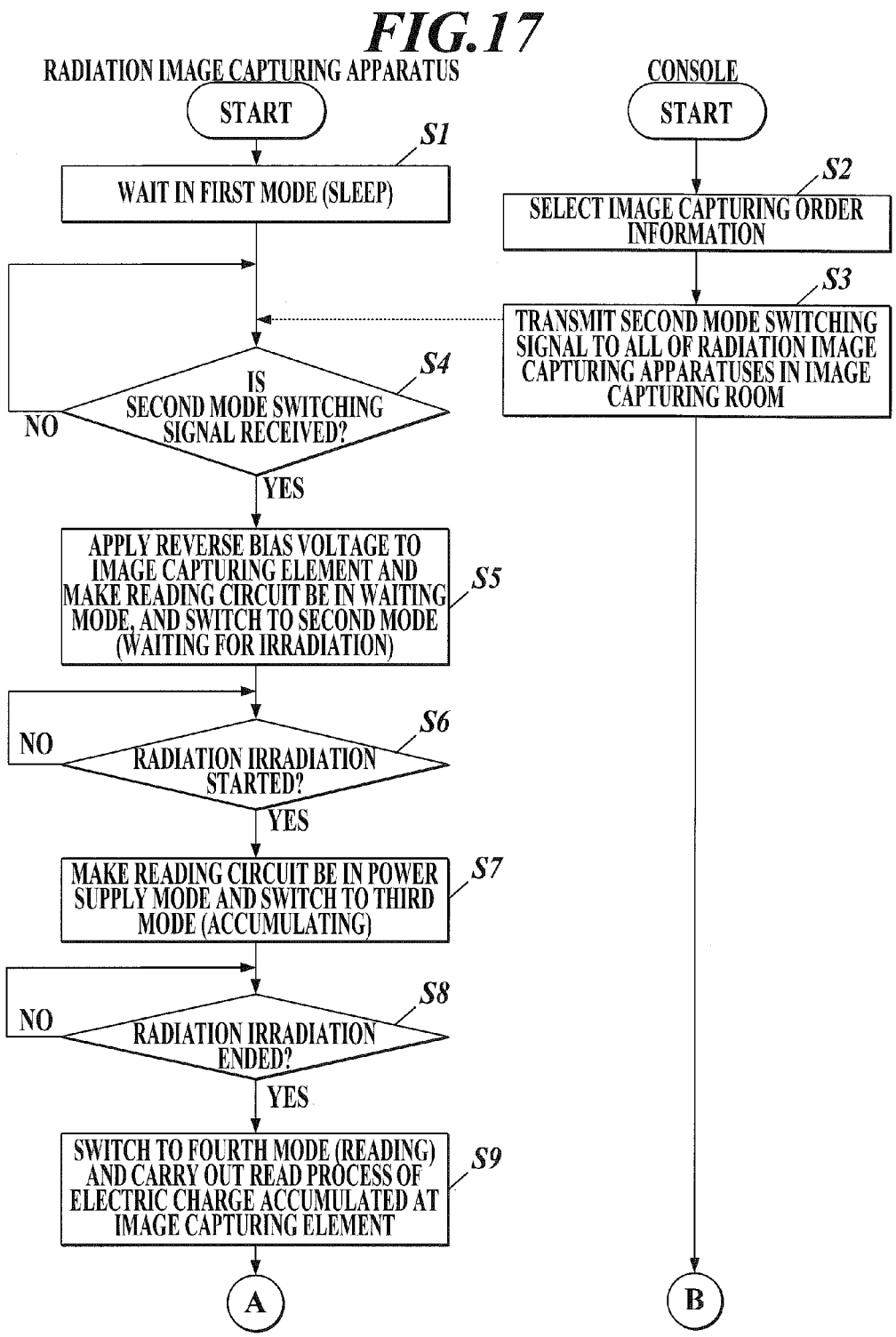
FIG. 17 This is the first diagram of a flowchart showing an example of a process procedure in the radiation image capturing system according to the second embodiment.

First, the radiation image capturing apparatuses 1A to 1E are disposed in the image capturing room R in a state where the power consumption mode thereof are in the first mode "mode 1" (sleep state) (step S1 of FIG. 17).

Before the radiation image capturing, the console control unit 107a of the consoled 107 reads out and obtains image capturing order information stored in the storage unit 107e (or obtains image capturing order information from HIS/RIS via a network) and displayed in the selecting screen H1 of the display unit 107d, for example, as shown in FIG. 19.

In the embodiment, the image capturing order information display column h11 for displaying the list of the image capturing order information stored in the storage unit 107e is provided in the selecting screen H1. Further, on the left side of the image capturing order information display column h11, selecting buttons h12 for selecting the image capturing order information to set the radiation image capturing of this time are provided so as to respectively correspond with the image capturing order information. Further, an OK button h13 and a return button h14 are provided below the image capturing order information display column h11.

On the selecting screen H1, an operator uses the input unit 107c to click the selecting button h12 which corresponds with the image capturing order information of the radiation image capturing of this time and clicks the OK button h13 to select the image capturing order information (step S2 of FIG. 17).

Then, when the image capturing order information of the radiation image capturing is selected and inputted by the input unit 107c of the console 107, the console control unit 107a transmits the second mode switching signal which instructs to switch to the second mode "mode 2" (waiting for irradiation state) to all of the radiation image capturing apparatuses 1A to 1E in the image capturing room R via the communication unit 107b and the wireless access point 103 (step S3 of FIG. 17). Further, the console 107 transmits the image capturing order information which is selected in the selecting screen H1 by an operator to the operation table 105 which is disposed in the front room Ra via a cable or the like.

On the other hand, the control unit 22 of each of the radiation image capturing apparatuses 1A to 1E disposed in the image capturing room R determines whether the second mode switching signal is received from the console 107 or not (step S4 of FIG. 17). When he control unit 22 of each of radiation image capturing apparatuses 1A to 1E determines that the second mode switching signal is received (step S4 of FIG. 17; YES), the control unit 22 applies the reverse bias voltage to the image capturing elements 7 and controls to make the mode switching switch be in the ON state and switches the power consumption mode to the second mode "mode 2" (waiting for irradiation state) from the first mode "mode 1" (sleep state) by switching the reading circuits 17 to the waiting mode where power is not to be supplied (step S5 of FIG. 17).

Here, the second mode switching signal which is transmitted from the console 107 is received by all of the radiation image capturing apparatuses 1A to 1E in the image capturing room R. Therefore, all of the radiation image capturing apparatuses 1A to 1E in the image capturing room R switches to the second mode "mode 2" (waiting for irradiation state) from the first mode "mode 1" (sleep state) by the instruction from the console 107.

Furthermore, the console 107 carries out a so-called dark reading process of performing a reading without radiation irradiation to each of the radiation image capturing apparatuses 1A to 1E in the image capturing room R to obtain a dark reading value. The dark reading value obtained by the dark reading process is used as an off set correcting value to carry out an off set correction in the after-mentioned image correction process.

Here, the timing of executing the dark reading process is not limited to before the image capturing, and the configuration may be such that the dark reading process is to be executed at the timing of after the image capturing.

Further, the configuration may be such that the dark reading process (the off set correcting process) is to be carried out at the radiation image capturing apparatus 1 side.

Next, the control unit 22 of each of the radiation image capturing apparatuses 1A to 1E in the image capturing room R determines whether the radiation irradiation is started or not by determining whether the voltage value V outputted from the electric current detection unit 42 exceeded the threshold value Vth or not (step S6 of FIG. 17).

When an operator finishes the operation of selecting the image capturing order information in the above described console 107, an operator moves into the image capturing room R from the console 107 and executes the radiation image capturing by using the radiation image capturing apparatus 1 which he/she desires to use among the five radiation image capturing apparatuses 1A to 1E which are disposed in the image capturing room R being in the second mode "mode 2" (waiting for irradiation state). In particular, an operator operates the switch 106 of the operation table 105 disposed in the front room Ra to activate the radiation generation device 102 and irradiates the radiation from the radiation generation device 102 to the desired radiation image capturing apparatus 1.

At this time, an operator may execute the radiation image capturing by using any radiation image capturing apparatus 1 among the five radiation image capturing apparatuses 1A to 1E in the image capturing room R which are in the second mode "mode 2" (waiting for irradiation state). That is, an operator may select the radiation image capturing apparatus 1 to be used for the image capturing at the timing when actually carrying out the radiation image capturing in the image capturing room R to carry out the radiation image capturing.

Further, an operator does not need to carry out any operations or work to select the radiation image capturing apparatus 1 to be used for the image capturing as the radiation image capturing apparatus 1 to be used for the image capturing, and an operator simply carries out the radiation image capturing by irradiating the radiation from the radiation generation device 102 to the radiation image capturing apparatus 1 which is to be used for the image capturing.

Hereinafter, in order to describe the process which is carried out in the radiation image capturing apparatus 1 to be used in image capturing and the process which is carried out in the radiation image capturing apparatuses 1 which are not used for the image capturing by discriminating the one process from the other, a case where an operator executes an image capturing by using the radiation image capturing apparatus 1E among the five radiation image capturing apparatuses 1A to 1E in the image capturing room R will be described as an example.

The control unit 22 of each of the radiation image capturing apparatuses 1A to 1D which do not detect radiation irradiation by not being used for the image capturing determines that the radiation irradiation does not start (step S6 of FIG. 17; No) and repeats the process of step S6.

On the other hand, when the control unit 22 of the radiation image capturing apparatus 1E which detects the radiation irradiation by being used for the image capturing detects that the voltage outputted from the electric current detection unit 42 due to the radiation irradiation exceeded the threshold value Vth and determines that the radiation irradiation is started (step S6 of FIG. 17; Yes), the control unit 22 of the radiation image capturing apparatus 1E makes the mode switching switch 24 be in the OFF state and supplies power to the reading circuits 17 and switches the power consumption mode of itself to the third mode "mode 3" (electric charge accumulating state) from the second mode "mode 2" (waiting for irradiation state) by switching the reading circuits 17 to the power supply mode (step S7 of FIG. 17).

That is, among the five radiation image capturing apparatuses 1A to 1E in the image capturing room R, only the radiation image capturing apparatus 1E which is actually used for the image capturing is automatically switched to the third mode "mode 3" (electric charge accumulating state) by receiving the radiation irradiation. On the other hand, the other radiation image capturing apparatuses 1A to 1D which are not used for the image capturing are to be maintained in the second mode "mode 2" (waiting for irradiation state).

Next, the control unit 22 of the radiation image capturing apparatus 1E which is used for the image capturing and which detected the radiation irradiation determines whether the radiation irradiation is ended or not by determining whether the voltage value V outputted from the electric current detection unit 42 is equal to or smaller than the threshold value Vth or not (step S8 of FIG. 17). Then, when the control unit 22 of the radiation image capturing apparatus 1E determines that the radiation irradiation is ended due to the voltage value V outputted from the electric current detection unit 42 being equal to or smaller than the threshold value Vth by the radiation irradiation from the radiation generation device 102 being ended (step S8 of FIG. 17; Yes), the control unit 22 of the radiation image capturing apparatus 1E makes the scan activation circuit 15 apply the ON voltage for signal reading to each of the scanning lines 5 to make the TFT 8 connected to each of the scanning line 5 be in the ON state and switches the power consumption mode of itself to the fourth mode "mode 4" (reading state) from the third mode "mode 3" (electric charge accumulating state). Thereafter, the control unit 22 of the radiation image capturing apparatus 1E executes the reading process of converting the electric charges accumulated in the image capturing elements 7 by the radiation irradiation into electric signals and stores the data obtained from the reading process to the storage unit 23 (step S9 of FIG. 17).

Moreover, the control unit 22 of the radiation image capturing apparatus 1E which detected the radiation irradiation carries out various types of image correction processes such as the offset correction and the like to the data obtained by the reading process to generate image data (raw data) and stores the generated image data (raw data) in the storage unit 22, and generates thinned image data from the generated image data (step S10 of FIG. 18). Then, the control unit 22 of the radiation image capturing apparatus 1E makes the generated thinned image data correspond with the cassette ID "1005" which is assigned to itself to transmit to the console 107 via the antenna device 39 and the wireless access point 103 (step S11 of FIG. 18).

Thereafter, the console 107 receives the thinned data which is transmitted from the radiation image capturing apparatus 1E which is used for the image capturing and which detected the radiation irradiation via the wireless access point 103 and the communication unit 107b (step S12 of FIG. 18).

The console control unit 107a of the console 107 which received the thinned image data which is transmitted from the radiation image capturing apparatus 1E which detected the radiation irradiation specifies the radiation image capturing apparatus 1E which detected the radiation irradiation (that is, the radiation image capturing apparatus 1E used for the image capturing) and the radiation image capturing apparatuses 1A to 1D which do not detect the radiation irradiation (that is, the radiation image capturing apparatuses 1A to 1D not used for the image capturing) among the radiation image capturing apparatuses 1A to 1E in the image capturing room R based on the cassette ID "1005" which is corresponded with the thinned image data and the list of cassette IDs of the radiation image capturing apparatuses 1A to 1E in the image capturing room R, which is stored in the storage unit 107a, and the like.

Ten, the console control unit 107a of the consoled 107 transmits the first mode switching signal which instructs to switch the power consumption mode to the first mode "mode 1" (sleep state) to the radiation image capturing apparatuses 1A to 1D other than the radiation image capturing apparatus 1E which is used for the image capturing, that is, the radiation image capturing apparatuses 1A to 1D which are not used for the image capturing, via the communication unit 107b and the wireless access point 103 (step S13 of FIG. 18).

The first mode switching signal which is transmitted from the console 107 is received by all of the radiation image capturing apparatuses 1A to 1D other than the radiation image capturing apparatus 1E which is used for the image capturing, and the power consumption mode of each of the radiation image capturing apparatuses 1A to 1D which are not used for the image capturing is switched to the first mode "mode 1" (sleep state) from the second mode "mode 2" (waiting for irradiation state).

Next, the control unit 107a of the console 107 makes the thinned image data which is received from the radiation image capturing apparatus 1E which detected the radiation irradiation correspond with the image capturing order information inputted by the input unit 107c and displays the thinned image data in the display unit 107d (step S14 of FIG. 18).

When an operator looks at the image data displayed in the display unit 107d of the console 107 and confirms whether another image capturing is needed or not, whether the image data corresponds with the correct image capturing order information or not and the like and determines that another image capturing is not to be carried out, an operator uses the input unit 107c to carry out an operation to instruct transmission of the original image data (raw data) of the thinned image data (step S15 of FIG. 18).

When the transmission of the original image data of the thinned image that is instructed by the input unit 107c, the console control unit 107a of the console 107 transmits an instruction signal for requesting the transmission of the original image data (raw data) to the radiation image capturing apparatus 1E which transmitted the thinned image data (that is, the radiation image capturing apparatus 1E which detected the radiation irradiation) via the communication unit 107b and the wireless access point 103 (step S16 of FIG. 18).

When the radiation image capturing apparatus 1E which transmitted the thinned image data (that is, the radiation image capturing apparatus 1E which is used for the image capturing and which detected the radiation irradiation) receives the instruction signal that requests the transmission of the original image data (raw data), the radiation image capturing apparatus 1E reads out the original image data (raw data) stored in the storage unit 23 and transmits the original image data to the console 107 via the antenna device 39 and the wireless access point 103 (step S17 of FIG. 18). Further, after transmitting the image data (raw data), the radiation image capturing apparatus 1E automatically switches the power consumption mode thereof to the first mode "mode 1" (sleep state) and ends the process (step S18 of FIG. 18).

On the other hand, when the console 107 receives the image data which is transmitted from the radiation image capturing apparatus 1E (step S19 of FIG. 18), the console 107 makes the received original image data (raw data) correspond with the image capturing order information and stores in the storage unit 107a and displays the received original image data in the display unit 107d along with the image capturing information (step S20 of FIG. 18) and ends the process.

A described above, according to the radiation image capturing system 100 of the present invention, the console 107 switches the power consumption mode of all of the radiation image capturing apparatuses 1A to 1E in the image capturing room R to the second mode "mode 2" (waiting for irradiation state) in which starting of radiation irradiation can be detected at the timing when the image capturing order information is inputted by the input unit 107c. Further, when the control unit 22 of the one radiation image capturing apparatus 1E which is used for the image capturing among the radiation image capturing apparatuses 1A to 1E in the image capturing room R detects the radiation irradiation by monitoring the current amount of the electric current that flows in the bias lines 9 detected by the electric current detection unit 42, the control unit 22 of the radiation image capturing apparatus 1E switches the power consumption mode thereof to the third mode "mode 3" (electric charge accumulating state) in which the reading circuits 17 are made to be in the power supply mode. Furthermore, the radiation image capturing apparatus 1E which is switched to the third mode "mode 3" (electric charge accumulating state) generates image data by reading out the electric charges accumulated in the image capturing elements 7 due to the radiation irradiation and transmits the image data to the console 107.

That is, only by an operator carrying out the operation of inputting image capturing order information, the image data is to be transmitted to the console 107 from the radiation image capturing apparatus 1 which is actually used for the image capturing, even when the radiation image capturing apparatus 1 to be used for the image capturing is not selected before the image capturing.

Therefore, in the radiation image capturing system 100 of the embodiment, an operator does not need to use the radiation image capturing apparatuses 1 by consciously identifying each of the radiation image capturing apparatuses 1, and further, an operator does not need to carry out any operations and works for selecting the radiation image capturing apparatus 1 to be used for the image capturing.

That is, an operator does not need to carry out an operation to identify the cassette ID of the radiation image capturing apparatus 1 which is to be used for the image capturing to search for the radiation image capturing apparatus 1 to which the cassette ID is attached among the plurality of radiation image capturing apparatuses 1. Further, an operator does not need to carry out an operation or a work to switch the power consumption mode of the radiation image capturing apparatus 1 which is used for the image capturing to the mode capable of carrying out the image capturing.

In such way, an operator can decide the radiation image capturing apparatus 1 to be used for the image capturing according to the condition and the like of a patient at the timing when actually carrying out the radiation image capturing and the radiation image capturing can be carried out by using the radiation image capturing apparatus 1 which an operator decided on.

Moreover, even when a case where the radiation image capturing apparatus 1 other than the radiation image capturing apparatus 1 which was planned to be used needs to be used occurs at the timing when carrying out the radiation image capturing, an operator does not need to carry out any operation for executing the image capturing by using another radiation image capturing apparatus 1.

Further, an operator inputs the image capturing order information in the console 107 before the image capturing. Other than that, an operator does not need to carry out any operation such as operating of the switch or taking out the radiation image capturing apparatus 1 from a cradle in the image capturing room R, and an operator simply needs to execute the radiation image capturing by using the desired radiation image capturing apparatus 1.

Furthermore, when carrying out the radiation image capturing, an operator does not need to be conscious about which radiation image capturing apparatus 1 is the radiation image capturing apparatus 1 which he/she is using.

As described above, in the radiation image capturing system 1 of the embodiment, the burden of an operator with regards to operations is very small, and the radiation image capturing system 1 of the embodiment is very convenient for an operator.

Moreover, the image data is transmitted to the console 107 from the radiation image capturing apparatus 1 which is actually used for the image capturing. Therefore, even when an operator mistakenly identifies and uses the radiation image capturing apparatus 1, the console 107 can obtain the correct image data from the radiation image capturing apparatus 1 which is actually used for the image capturing.

That is, for example, when an operator executes the radiation image capturing by mistakenly using the radiation image capturing apparatus 1E to which the cassette ID "1005" is assigned thinking that he/she is using the radiation image capturing apparatus 1D to which the cassette ID "1004" is assigned, the image data is to be transmitted to the console 107 from the radiation image capturing apparatus 1E having the cassette ID "1005" which is actually used for the image capturing. Therefore, the correct image data can be obtained even when the radiation image capturing apparatuses 1 are mixed up.

Accordingly, in the radiation image capturing system 100 of the present invention, even when an operator mixes up the radiation image capturing apparatuses 1, a mistake such as mixing up of image data (for example, handling data of a different patient as the image data of the patient who is targeted for the image capturing) does not occur. Further, a mistake such as carrying out the radiation image capturing by using the radiation image capturing apparatus 1 which is in the sleep state can be prevented.

Therefore, in the radiation image capturing system 100 of the embodiment, medical mistakes can be prevented from occurring and the psychological burden of an operator that he/she cannot make a mistake can be reduced. Further, increase in the burden of an operator and a patient associated with the need to execute the image capturing again and unnecessary consumption of power can be prevented.

Moreover, because the reading circuits 7 are maintained to be in the waiting mode in which the power consumption is small until radiation is irradiated to the radiation image capturing apparatus 1, the time period for the reading circuits 17 be in the power supply mode in which the power consumption is larger comparing the that in the waiting mode can be prevented from becoming unnecessarily long. Therefore, the power consumption at the time of radiation image capturing can be reduced and wasting of power can be inhibited.

Further, because the radiation image capturing apparatuses 1 which are not to be used for the image capturing are switched to the first mode "mode 1" in which the power consumption is even smaller comparing to that in the second mode "mode 2" by the control of the console 107, the power consumption can be reduced even more.

That is, in a case where the radiation image capturing apparatus 1 which is switched to the second mode "mode 2" by the control of the console 107 does not detect radiation irradiation for more than a predetermined time period, unnecessary power consumption in the radiation image capturing apparatuses 1 which are not to be used for the image capturing increases when the time interval for switching to the first mode "mode 1" from the second mode "mode 2" is set sufficiently long in the system where the apparatuses are switched to the first mode voluntarily. On the other hand, when the time interval for switching to the first mode "mode 1" from the second mode "mode 2" is set to be short, there is a possibility that all of the radiation image capturing apparatuses 1 are already switched to the first mode "mode 1" at the time of actually carrying out the radiation image capturing when the time period from when the apparatus is switched to the second mode "mode 2" to the execution of the radiation image capturing is long.

Comparing to the above cases, when it is configured that the radiation image capturing apparatus 1 which is not to be used for the image capturing is switched to the first mode "mode 1" from the second mode "mode 2" by the control of the console 107 as in the radiation image capturing system 100 of the embodiment, the radiation image capturing apparatus 1 which is not to be used for the image capturing can be switched to the first mode "mode 1" at more appropriate timing.

Moreover, because the image capturing order information which is inputted by the input unit 107c is made to correspond with the image data which is transmitted from the radiation image capturing apparatus which is actually used for the image capturing in the console 107, the convenience is improved.

Furthermore, because the radiation image capturing apparatus 1 which is used for the image capturing and which detects the radiation irradiation generates the thinned image data and sends the generated thinned image data to the console 107, an operator can confirm the image on the console 107 to determine whether the image capturing needs to be carried out again or not in an early stage.

Here, in the above embodiment, the case of the configuration where the power consumption mode of the radiation image capturing apparatuses which are not used for the image capturing and which do not detect radiation irradiation are switched to the first mode "mode 1" (sleep state) from the second mode "mode 2" (waiting for irradiation state) according to the first mode switching signal which is transmitted from the console 107 after the image data which is transmitted from the radiation image capturing apparatus 1 which detected the radiation irradiation is received by the console 107 is described. However, the timing of switching the power consumption mode of the radiation image capturing apparatuses 1 which do not detect the radiation irradiation to the first mode "mode 1" (sleep state) is not limited to the above timing.

For example, the configuration may be such that when the radiation image capturing apparatus 1 does not detect radiation irradiation within a predetermined time period after the power consumption mode is switched to the second mode "mode 2" (waiting for irradiation state) from the first mode "mode 1" (sleep state) according to the second mode switching signal transmitted from the console 107, the power consumption mode thereof is automatically switched to the first mode "mode 1" (sleep state) from the second mode "mode 2" (waiting for irradiation state) by the control unit 22. By having the configuration as described above, there is no need to send and receive a signal or the like for switching the power consumption mode of the radiation image capturing apparatus 1 to the first mode "mode 1" (sleep state) between the console 107 and the radiation image capturing apparatus 1, and the control configuration can be simplified.

Furthermore, for example, the configuration may be such that the radiation image capturing apparatus 1 which detected the radiation irradiation notifies to the console 107 of the detection of the radiation irradiation along with the cassette ID of itself right after the radiation irradiation is detected, and the console 107 which received the notification transmits the first mode switching signal which instructs to switch to the first mode to the radiation image capturing apparatuses 1 other than the radiation image capturing apparatus 1 which detected the radiation irradiation to switch the power consumption mode of the radiation image capturing apparatuses 1 which does not detect the radiation irradiation to the first mode "mode 1" (sleep state) from the second mode "mode 2" (waiting for irradiation state). By having such configuration, the power consumption mode of the radiation image capturing apparatuses 1 which are not to be used for the image capturing can be switched to the first mode "mode 1" (sleep state) in an even more early stage, and the power consumption can be reduced even more.

Moreover, in the above embodiment, the case where the console 107 is disposed at a place different from the image capturing room R and the front room Ra. However, the configuration may be such that the console 107 is to be disposed in the front room Ra.

Here, as described above, the input of a predetermined information by the input unit includes the operation of selecting a desired image capturing order information from the image capturing order information which are displayed in a list form in the display unit 107d of the console 107c.

Moreover, in the above embodiment, the case where the power consumption mode of all of the radiation image capturing apparatus 1 in the image capturing room R is switched to the second mode "mode 2" (waiting more irradiation state) based on the image capturing order information being selected and inputted as a predetermined information by the input unit 107c in the console 107 is described. However, the predetermined information is not limited to the image capturing order information and can be any information or operation which is made to correspond with the radiation image capturing. That is, the configuration may be such that when any kind of operation which is made to correspond with the radiation image capturing is carried out in the console 107, it is determined that the predetermined information is inputted by the input unit and the power consumption mode of all of the radiation image capturing apparatuses 1 in the image capturing room R is switched to the second mode "mode 2" (waiting for irradiation state).

For example, the configuration may be such that when the image capturing condition such as the image capturing part or the like is selected by the input unit 107c, the power consumption mode of all of the radiation image capturing apparatuses 1 in the image capturing room R is switched to the second mode "mode 2" (waiting for irradiation state) assuming that the predetermined information is inputted by the input unit.

Moreover, for example, the configuration may be such that when the activation operation is carried out in the console 107, the power consumption mode of all the radiation image capturing apparatuses 1 in the image capturing room R is switched to the second mode "mode 2" (waiting for irradiation state) assuming that the predetermined information is inputted by the input unit. The activation operation includes such operation to activate the console 107 from the sleep state by an operator touching the screen (display unit) of the console 107.

Furthermore, for example, the configuration may be such that by setting the information which instructs to start the radiation image capturing as the predetermined information, the power consumption mode of all of the radiation image capturing apparatuses 1 in the image capturing room R is switched to the second mode "mode 2" (waiting for irradiation state) based on starting of the radiation image capturing being instructed in the input unit 107c.

Further, for example, the configuration may be such that by setting the information to select the image capturing room R in which the radiation image capturing is to be carried out as the predetermined information, the power consumption mode of all of the radiation image capturing apparatuses 1 in the image capturing room R is switched to the second mode "mode 2" (waiting for irradiation state) based on the image capturing room R in which the radiation image capturing is to be carried out being selected by the input unit 107c.

Moreover, in the above embodiment, the configuration where the radiation image capturing apparatus 1 which detected the radiation irradiation transmits the thinned image data to the console 107 prior to the image data (raw data) which is the original of the thinned image data is described. However, the configuration may be such that the thinned image data is not generated and only the image data (raw data) is to be transmitted.

Further, in the above embodiment the case where the radiation image capturing is executed once is described. However, the radiation image capturing system 100 of the present invention can be applied to a case where a plurality of radiation image capturing is executed continuously.

Furthermore, in the above embodiment, the case where the image data is transmitted to the console 107 from the radiation image capturing apparatus 1 when an operator requests the transmission of the image data by the input unit 107c of the console 107 is described. However, the configuration may be such that by providing an image transmission switch for instructing the image data transmission to the radiation image capturing apparatus 1, the image data is transmitted to the console when the image transmission switch is operated by an operator.

Moreover, in the above embodiment, the configuration where the console 107 recognizes the radiation image capturing apparatuses 1 in the image capturing room R in advance is described. However, when each of the radiation image capturing apparatuses 1 in the image capturing room R is switched to the second mode "mode 2", the thinned image data and the original image data are automatically transmitted to the console 107 from the radiation image capturing apparatus 1 which detected the radiation irradiation. Therefore, the console 107 does not need necessarily to recognize the radiation image capturing apparatuses 1 in the image capturing room R.

Thus, in the above embodiment, although the case where the tag for storing the cassette ID and the like is embedded in each of the radiation image capturing apparatuses 1 and the radiation image capturing apparatuses 1 in the image capturing room R are detected by the tag reader 104 is described, the tags of the radiation image capturing apparatuses 1 and the tag reader 104 are not needed necessarily.

Third Embodiment

Next, the radiation image capturing system 200 according to the third embodiment of the present invention in which the radiation image capturing is carried out by using the above described radiation image capturing apparatus 1 will be described.

Figure 20:
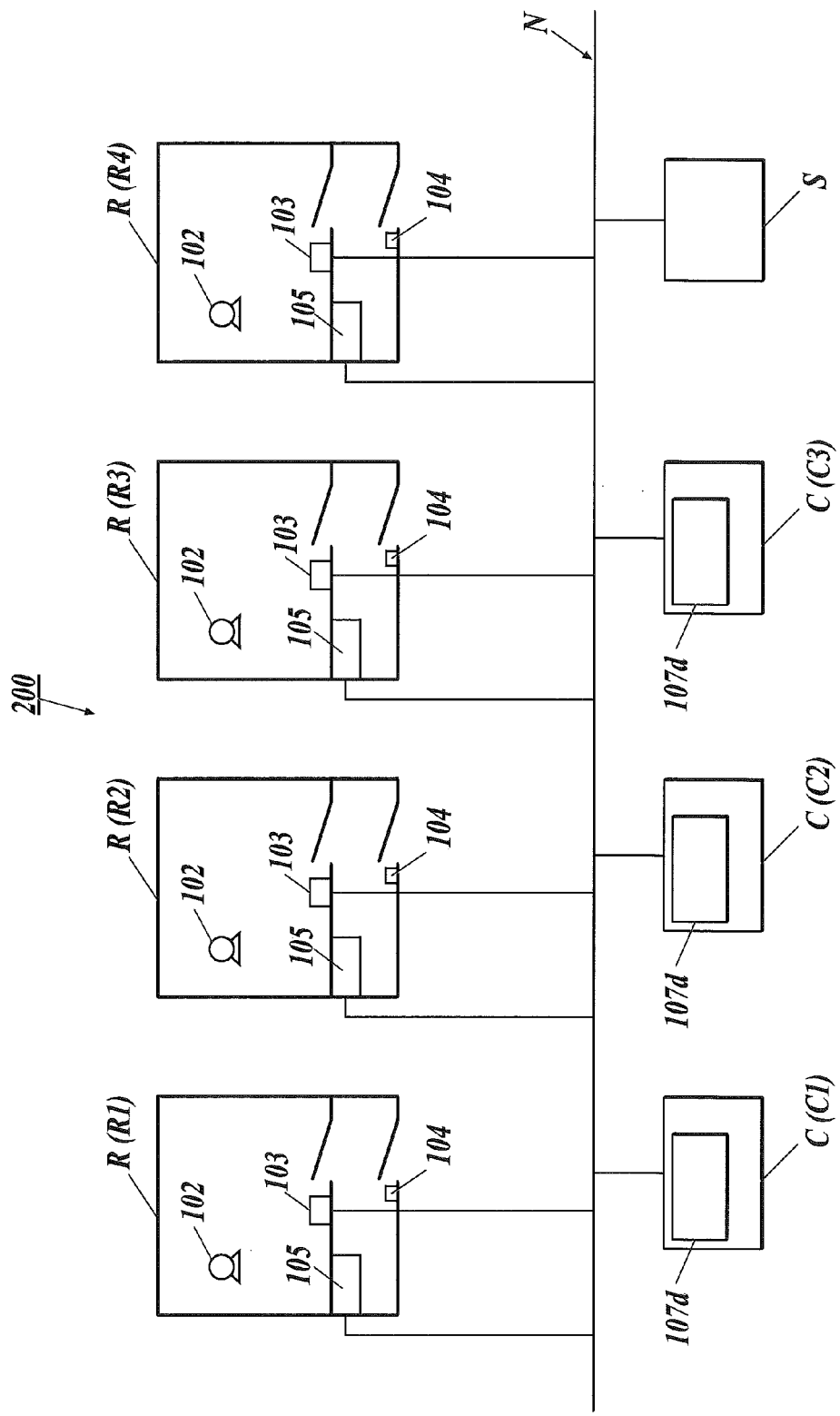
FIG. 20 This is a diagram showing an overall configuration of a radiation image capturing system according to the third embodiment.

The radiation image capturing system 200 according to the embodiment is a system assuming the radiation image capturing carried out in a hospital and a clinic. As shown in FIG. 20, for example, the radiation image capturing system 200 includes a plurality of image capturing rooms R in each of which an image capturing of a target body (a part of a patient which is target for image capturing) which is a part of a patient is carried out by irradiation radiation thereto, a plurality of consoles C which carry out a control of the entire radiation image capturing system 200, a data management server S and the like.

In the embodiment, as shown in FIG. 20, a case where four image capturing rooms of R1 to R4 are provided and three consoles C of C1 to C3 are provided is described. However, the number of image capturing rooms and the number of consoles are not limited to the above numbers. Further, the present invention is also applied to a system in which one console C is provided so as to be shared among a plurality of image capturing rooms R.

Hereinafter, when individually identifying each of the image capturing rooms R, the image capturing rooms will be described by respectively calling them as the image capturing rooms R1 to R4. When there is no need to individually identifying each of the image capturing rooms R, the image capturing rooms R1 to R4 will be described by collectively calling them as the image capturing room R. Similarly, when individually identifying each of the consoles 107, the consoles will be described by respectively calling them as the consoles C1 to C3. When there is no need to individually identifying each of the consoles 107, the consoles C1 to C3 are described by collectively calling them as the console C.

In each image capturing room R, a plurality of the above described radiation image capturing apparatuses 1 are disposed. For example, as shown in FIG. 13, five radiation image capturing apparatuses 1A to 1E are disposed in the image capturing room R1. Further, although it is not shown in the drawings, two radiation image capturing apparatuses 1F and 1G are disposed in the image capturing room R2, three radiation image capturing apparatuses 1H to 1J are disposed in the image capturing room R3 and four radiation image capturing apparatuses 1K to 1N are disposed in the image capturing room R4, for example.

Hereinafter, when individually identifying each of the radiation image capturing apparatuses, the radiation image capturing apparatuses will be described by respectively calling them as the radiation image capturing apparatuses 1A to 1K. When there is no need to individually identifying each of the radiation image capturing apparatuses, the radiation image capturing apparatuses 1A to 1K will be described by collectively calling them as the radiation image capturing apparatus 1.

In the embodiment, the configurations in each of the image capturing rooms R and in the front room Ra are similar to the case in the above described second embodiment, and each of the image capturing room R includes the bucky 101, the radiation generation device 102, the wireless access point 103 and the like and the front room Ra includes the tag reader 104, the operation table 105, the switch 106 and the like (see FIG. 13).

Here, in FIG. 20, one radiation generation device 102 is shown in each of the image capturing rooms R1 to R4. However, a plurality of radiation generation devices 102 may be included in one image capturing room R and the radiation generation devices 102 may be disposed so as to respectively correspond to the plurality of bucky 101. Furthermore, a portable radiation generation device which can be carried to arbitrary places in the image capturing room R1 and which can irradiate radiation in arbitrary directions may be provided.

Moreover, the configuration of the radiation image capturing apparatus 1 is as described in the first embodiment, and as described in the second embodiment, the cassette ID is assigned to the radiation image capturing apparatus 1, and further, the tag (not shown in the drawing) is embedded in the radiation image capturing apparatus 1. Furthermore, also in the embodiment, the radiation image capturing apparatus 1 is configured in a size that complies with JIS Z 4905 (the corresponding international standard is IEC 60406) of the conventional cassette for screen/film.

Further, the radiation image capturing apparatus 1 can be used by itself in a state where the radiation image capturing apparatus 1 is not mounted in the bucky 101. That is, the radiation image capturing apparatuses 1 can be used by arranging the radiation image capturing apparatus 1 to the supporting platform or the bucky for recumbent position image capturing which are provided in the image capturing room R by itself, for example, and placing a hand or the like of a patient which is the target body on the radiation incidence surface R (see FIG. 1) thereof or by placing the radiation image capturing apparatus 1 between the hip or a leg of the patient who is in a recumbent position on the bed and the bed.

In the embodiment, the radiation image capturing apparatus 1 is connected to the consoles C1 to C3 via the antenna device 39 and the wireless access point 103 as the communication unit, and the radiation image capturing apparatus 1 receives and sends various types of control signals and data with each of the consoles C1 to C3 by the wireless communication.

Here, although the description overlaps with the above given description, flow of the switching of the power consumption mode which is carried out in the radiation image capturing apparatus 1 when executing the radiation image capturing will be described.

The radiation image capturing apparatuses 1 are disposed in the image capturing room R in the state where the power consumption mode is switched to the first mode "mode 1" (sleep mode). As described above, the first mode "mode 1" (sleep mode) is a mode in which power is supplied only to the necessary units such as the control unit 22, the storage unit 23, the antenna device 39 and the like and power is not supplied to the reading circuits 17, the image capturing elements 7, the TFT 8 and the like.

Further, when the control unit 22 of the radiation image capturing apparatus 1 receives the second mode switching signal which instructs to switch to the second mode "mode 2" (waiting for irradiation state" from the console C in the state of being switched to the first mode "mode 1" (sleep state), the control unit 22 starts to apply the reverse bias voltage to the image capturing elements 7 and makes the mode switching switch 24 be in the ON state to switch the reading circuits 17 be in the power supply mode from the waiting mode and to switch the power consumption mode of the radiation image capturing apparatus 1 to the second mode "mode 2" (waiting for irradiation state) from the first mode "mode 1" (sleep state).

As described above, the second mode "mode 2" (waiting for irradiation state) is the mode where starting of radiation irradiation to the radiation image capturing apparatus 1 can be detected based on the voltage value V outputted from the electric current detection unit 42 according to the current amount of the electric current that flows in the connection 10 of the bias lines 9.

Here, also in the radiation image capturing system 200 of the present invention, the configuration in which it is determined that radiation irradiation to the radiation image capturing apparatus 1 is started at the time "t start" when the voltage value V outputted from the electric current detection unit 42 exceeded the threshold value Vth and it is determined that the radiation irradiation to the radiation image capturing apparatus 1 is ended at the time "t end" when the voltage value V outputted from the electric current detection unit 42 be equal to or smaller than the threshold value Vth will be described. However, as described above, the configuration may be such that starting and ending of the radiation irradiation is detected based on the change rate $\Delta V$ of the voltage value V outputted from the electric current detection unit 42 or the estimated value of the total amount of the voltage value V outputted from the electric current detection unit 42.

When the radiation image capturing apparatus 1 is switched to the second mode "mode 2" (waiting for irradiation state" according to the second mode switching signal from the console C, as described above, the control unit 22 of the radiation image capturing apparatus 1 monitors the voltage value V outputted from the electric current detection unit 42 and detects the starting of radiation irradiation to the radiation image capturing apparatus 1 by determining whether the voltage value V outputted from the electric detection unit 42 exceeded the threshold value Vth or not.

When the control unit 22 of the radiation image capturing apparatus 1 detects that the radiation irradiation is started in the state of being switched to the second mode "mode 2" (waiting for irradiation state), the control unit 22 switches the reading circuits 17 to the power supply mode from the waiting mode and switches the power consumption mode of the radiation image capturing apparatus 1 to the third mode "mode 3" (electric charge accumulating state) from the second mode "mode 2" (waiting for irradiation state).

In the third mode "mode 3" (electric charge accumulating state), as described above, the reverse bias voltage is applied to the image capturing elements 7 and power is supplied to the reading circuits 17, and electric charge is generated in the image capturing elements 7 by the radiation irradiation and the electric charge according to the amount of radiation irradiated is accumulated in each of the image capturing elements 7.

Further, after being switched to the third mode "mode 3" (electric charge accumulating state), the control unit 22 of the radiation image capturing apparatus 1 monitors the voltage value V outputted from the electric current detection unit 42 and detects that the radiation irradiation to the radiation image capturing apparatus 1 is ended by determining whether the voltage value V outputted from the electric current detection unit 42 is equal to or smaller than the threshold value Vth or not.

Here, it may be determined that the radiation irradiation is ended assuming that the radiation irradiation is ended after a predetermined time period elapsed since the starting of the radiation irradiation.

When the ending of the radiation irradiation is detected in a state where the radiation image capturing apparatus 1 is switched to the third mode "mode 3" (electric charge accumulating state), the control unit 22 switches the power consumption mode of the radiation image capturing apparatus 1 to the fourth mode "mode 4" (reading state) from the third mode "mode 3" (electric charge accumulating state) and executes the reading process of reading out the electric charge accumulated in the image capturing elements 7 and converts the electric charge to electric signals. In the reading process, the electric charge accumulated in each of the image capturing elements 7 by the radiation irradiation is converted to an electric signal and stored in the storage unit 23.

As for the radiation image capturing apparatus 1 which finished the reading process of reading out the electric charge accumulated in each of the image capturing elements 7 generating the image data (raw data) by carrying out various types of correction processes as needed and generation the thinned image data from the generated image data, the procedure is as described in the second embodiment.

Then, in the embodiment, the radiation image capturing apparatus 1 transmits the generated thinned image data to the console 107 via the antenna device 39 and the wireless access point 103. At this time, by the radiation image capturing apparatus 1 transmitting the thinned image data by making the cassette ID which is assigned to itself correspond to the thinned image data, the cassette ID of the radiation image capturing apparatus 1 itself is notified to the console 107.

Further, when the radiation image capturing apparatus 1 receives the instruction signal for requesting the transmission of the original image data (raw data) of the thinned image data from the console C which is the destination of the image data via the wireless access point 103 and the antenna device 39, the radiation image capturing apparatus 1 reads out the original image data of the thinned image data from the storage unit 23 to transmit to the console C which is the destination of the image data via the antenna device 39 and the wireless access point 103.

Here, in the image capturing carried out in one image capturing room R except when carrying out image forming of subtraction system, two or more of the radiation image capturing apparatuses 1 will not be used at one radiation image capturing. That is, most of the time, the radiation image capturing is executed by using one radiation image capturing apparatus 1 and the radiation irradiation is carried out to only one radiation image capturing apparatus 1.

Therefore, in one radiation image capturing, there is only one radiation image capturing apparatus 1 that detects radiation irradiation in one image capturing room R, and other radiation image capturing apparatuses 1 which are in the same image capturing room R do not detect radiation irradiation. Further, the console C receives image data only from the one radiation image capturing apparatus 1 which detected radiation irradiation in one image capturing room R.

As will be described later, the cassette ID of the radiation image capturing apparatus 1 in the image capturing room R is read by the tag reader 104 and the cassette ID is notified to the console C, and the console C recognizes each radiation image capturing apparatus 1 in the image capturing rooms R. Further, the power consumption mode of each radiation image capturing apparatus 1 in the image capturing room R in which the image capturing is carried out is switched to the first mode "mode 1" (sleep state) from the second mode "mode 2" (waiting for irradiation state) based on the first mode switching signal which is transmitted from the console C after the image data which is transmitted by the radiation image capturing apparatus 1 in the image capturing room R is made to correspond with the image capturing order information and the correspondence is decided by an operator in the console C.

Further, even when each radiation image capturing apparatus 1 does not detect the radiation irradiation within a predetermined time period after switching to the second mode "mode 2" (waiting for irradiation state), the power consumption mode thereof is to be automatically switched to the first mode "mode 1" (sleep state) from the second mode "mode 2" (waiting for irradiation state).

(Console C)

Similarly to the console 107 of the second embodiment, the console C (see FIG. 20) includes a console control unit 107a, a communication unit 107b, an input unit 107c, a display unit 107d and a storage unit 107e (see FIG. 15).

For example, the console control unit 107a is constituted of a generalized CPU, a ROM, a RAM and the like (all of which are not shown in the drawing), and the console control unit 107a reads out a predetermined program stored in the ROM and expands the program in the working area of the RAM and the CPU executes various types of processes according to the program.

The communication unit 107b is for carrying out communication with the radiation image capturing apparatuses radiation image capturing apparatuses 1 via the wireless access point 103, and the communication unit 107b carries out sending and receiving of various types of control signals, data and the like with the radiation image capturing apparatuses 1.

The input unit 107c is constituted of a key board, a mouse and the like for inputting various types of instructions and information.

In particular, the input unit 107c is operated as the selecting unit when an operator selects the image capturing room R in which the image capturing is to be carried out among the plurality of image capturing rooms R1 to R4 before the radiation image capturing.

Further, the input unit 107c is operated when an operator inputs the operator ID before the radiation image capturing and also, is operated when the operator inputs the operator ID again after the image capturing in the image capturing room R.

Furthermore, the input unit 107c is operated as the second selecting unit when an operator selects the console c as the destination of the image data to which the image data obtained by the radiation image capturing is to be transmitted among the plurality of consoles C1 to C3 before the radiation image capturing.

Moreover, the input unit 107c is operated when an operator sets information of a patient who is target for the radiation image capturing and an image capturing condition before the radiation image capturing. As will be described later, the patient information and the image capturing condition are set by an operator selecting and inputting the image capturing information as a predetermined information by using the input unit 107c. The selection (input) of the image capturing order information can be carried out at any timing before the radiation image capturing or after the radiation image capturing.

Further, the input unit 107c is operated when an operator decides on the correspondence of the one or plurality of image data which is transmitted from the radiation image capturing apparatus 1 which is used for the radiation image capturing in the image capturing room R and the image capturing order information which are inputted before the image capturing or after the image capturing after the radiation image capturing in the selected image capturing room R.

The display unit 107d is formed of CRT, LCD or the like, and the display unit 107d displays images and various types of information such as the image capturing order information which are transmitted from the radiation image capturing apparatus 1. When a plurality of image data are transmitted from the same image capturing room R, the display unit 107d displays the image data in the same screen together by the image capturing room R units.

The storage unit 107e is constituted of a hard disk or the like and stores various types of information.

In particular, the storage unit 107e stores the status of usage of each of the image capturing rooms R1 to R4, that is, whether each of the image capturing rooms R1 to R4 are "in use" or "vacant". The console C determines that the image capturing room R which is not selected by any of operators can be selected as the image capturing room R to be used for image capturing and stores that the image capturing room R is "vacant" in the storage unit 107e.

Further, when an operator selects the selected room R by the input unit 107c before the radiation image capturing, the console C determines that the image capturing room R which is selected by the operator cannot be selected and changes the status of usage of the image capturing room R in the storage unit 107e to "in use" from "vacant".

Furthermore, a list of the radiation image capturing apparatuses 1 in each of the image capturing room R is stored in the storage unit 107e. In the list of the radiation image capturing apparatuses 1 stored in the storage unit 107e, the cassette ID, the type information of the scintillaor, the size information, the resolution level and the like of each of the radiation image capturing apparatuses 1A to 1N in the image capturing rooms R1 to R4 are stored. When the information unique to the radiation image capturing apparatus 1 which is detected b the tag reader 104 disposed near the entrance of the front room Ra including the cassette ID of the radiation image capturing apparatus 1 is transmitted to the console C as described above, the console 107 refers to the list of the radiation image capturing apparatuses 1 in the image capturing rooms R, which is registered in the storage unit 107e.

Then, when the information unique to the radiation image capturing apparatus 1 which is transmitted is not registered in the storage unit 107e, the console C determines that the radiation image capturing apparatus 1 is newly brought into the image capturing rooms R and adds the cassette ID and the like of the radiation image capturing apparatus 1 to the above mentioned list and stores in the storage unit 107e.

Further, when the information unique to the radiation image capturing apparatus 1 which is transmitted is already registered in the storage unit 107e, the console C determines that the radiation image capturing apparatus 1 was taken out from the image capturing rooms R and deletes the cassette ID and the like of the radiation image capturing apparatus 1 from the list.

In such way, the console C stores the cassettes IDs and the like of the radiation image capturing apparatuses 1 in the image capturing room R in the storage unit 107e and recognizes which of the radiation image capturing apparatuses 1 are in the image capturing rooms R.

Furthermore, the image capturing order information including the information of a patient who is target for the radiation image capturing in the image capturing room R1 and the image capturing condition is stored in the storage unit 107e. The image capturing order information is to be stored in the storage unit 107e in advance in a list form before the radiation image capturing.

In the embodiment, as shown in FIG. 16, the image capturing order information includes "patient ID" P2, "patient name" P3, "gender" P4 and "age" P5 as the patient information and "image capturing part" P6 and "image capturing direction" P7 as the image capturing condition. Further, "image capturing order ID" P1 is automatically assigned to the image capturing information in the order of acceptance of the image capturing order.

Here, contents of the patient information and the image capturing condition to be written in the image capturing order information are not limited to the above, and for example, information such as the birth date of the patient, the number of times of examinations, the amount of radiation, whether the patient is fat or thin can be included, and the contents can be set arbitrarily. Further, for example, the console 107 can be connected to HIS (Hospital Information System) and RIS (Radiology Information System) (both are not shown in the drawing) via a network and the image capturing order information may be obtained from HIS or RIS.

Furthermore, the image data received from the radiation image capturing apparatus 1 is to be stored in the storage unit 107e by being corresponded with the image capturing order information.

Moreover, the storage unit 107e makes the image data which is received from the radiation image capturing apparatus 1 in the image capturing room R in which the image capturing is carried out correspond with the image capturing room ID of the image capturing room R in which the image capturing is carried out to store the image data received from the image capturing room R in units of each image capturing room R.

Further, when a plurality of image data are transmitted from the radiation image capturing apparatus in the one image capturing room R which is selected, the storage unit 107e groups the image data and makes the image data in each group to correspond with the image capturing room ID of the image capturing room R to store them.

Furthermore, when an operator ID is inputted and the image capturing room R is selected by the input unit 107c before the radiation image capturing, the storage unit 107e makes the image capturing room ID of the selected image capturing room R correspond with the operator ID to store.

When the console control unit 107a of the console C receives the image data which is transmitted from the radiation image capturing apparatus in the image capturing room R via the wireless access point 103 and the communication unit 107b, the console control unit 107a determines the wireless access point 103 which the image data went through based on the address of the wireless access point 103 which is attached to the received image data as the head information. Then, the console control unit 107a specifies the image capturing room R which corresponds with the wireless access point which the image data went through as the image capturing room R in which the radiation image capturing apparatus which transmitted the image data is disposed.

Moreover, when an operator who finished the image capturing in the image capturing room R moves to the console C which is selected as the destination of the image from the image capturing room R and inputs the operator ID by the input unit 107c, the console control unit 107a reads out the image capturing room ID of the image capturing room R which is made to correspond with the inputted operator ID from the storage unit 107e and determines whether the image capturing room ID of the image capturing room R which is read out and the image capturing room ID of the image capturing room R in which the radiation image capturing apparatus 1 which transmitted the image data is disposed match each other or not. When they match, it is determined that the it is the correct image capturing room R, that is, it is determined that the image capturing was carried out in the image capturing room R which was selected by the operator. On the other hand, when they do not match, it is determined that the image capturing was carried out in a wrong image capturing room R which is different from the image capturing room R selected by the operator.

Further, when the storage unit 107e of itself is updated, each of the consoles C1 to C3 transmits the updated content to other consoles C which are connected to the same network N. Then, the content of the storage unit 107e of each of the console C1 to C3 is to be updated based on the updated data which are transmitted from other consoles C.

Here, the configuration may be such that the list of radiation image capturing apparatuses 1, image capturing order information, image data and the like stored in the storage unit 107e of each console C are stored in the data management server S and the data management server S transmits data to the console C according to the request from the console C.

In addition, an imager which stores the radiation image in an image recording medium such as a film based on the image data outputted from the console C and outputs the radiation image is arbitrarily connected to the console C, for example.

In the embodiment, the console C can communicate with all of the radiation image capturing apparatus 1A to 1N in the image capturing rooms R via the communication unit 107b and the wireless access point 103 provided in each of the image capturing rooms R. Further, when an operator selects the image capturing room R to be used for the image capturing by the input unit 107c, the console C is made to correspond with the selected image capturing room R.

When the image capturing room R to be used for the image capturing is selected by the input unit 107c, the console C transmits the second mode switching signal to the radiation image capturing apparatuses 1 which are disposed in the selected image capturing room R by being in the first mode (sleep state) to switch the power consumption mode of all of the radiation image capturing apparatuses 1 in the image capturing room R to the second mode "mode 2" (waiting for irradiation state) from the first mode "mode 1" (sleep state).

Further, when transmitting the second mode switching signal, the console C notifies the radiation image capturing apparatuses 1 in the selected image capturing R of the console C which is selected and input as the destination of the image data by the input unit 107c. For example, the console C transmitting the identification information for specifying the console C which is selected as the destination of the image data along with the second mode switching signal, the console C notifies the radiation image capturing apparatuses 1 of the console C which is selected as the destination of the image data.

Furthermore, when the console C itself is selected as the console C which is the destination of the image data, the console C receives the thinned image data which is transmitted from any one of radiation image capturing apparatus 1 which detected radiation irradiation via the wireless access point 103 and the communication unit 107b.

Then, the console C which is selected as the destination of the image data and which received the thinned image data which is transmitted from the radiation image capturing apparatus 1 obtains the cassette ID of the radiation image capturing apparatus 1 corresponded with the received thinned image data. At this time, the console C displays the thinned image data which is transmitted from the image capturing room R (that is, the image capturing room R in which an operator carried out the image capturing) having the image capturing room ID which is made to correspond with the operator ID inputted by the input unit 107c in the display unit 107d.

Further, when the operator who looked as the images in the display unit 107d determines whether the image capturing needs to be carried out again or not and the like and carries out the operation to request the transmission of the image data which is original of the thinned image data, the instruction to request the transmission of the image data which is the original of the thinned image data is to be transmitted to the radiation image capturing apparatus 1 which transmitted the thinned image data based on the cassette ID of the radiation image capturing apparatus 1 which transmitted the thinned image data via the communication unit 107b and the wireless access point 103.

Moreover, when the console C which is selected as the destination of the image data and which received the thinned image data receives the image data which is the original of the thinned image data from the radiation image capturing apparatus 1 used for the image capturing, the console C makes the image based on the image data which is the original of the received thinned image data correspond with the image capturing order information which is inputted by the input unit 107c and displays the image in the display unit 107d. Further, when the correspondence of the image data which is the original of the thinned image data and the image capturing order information is decided on, the console C determines that the radiation image capturing in the image capturing room R is finished and transmits the first mode switching signal which instructs to switch to the first mode "mode 1" (sleep state) via the communication unit 107b and the wireless access point 103 to make all of the radiation image capturing apparatuses 1 in the image capturing room R switch to the first mode "mode 1" (sleep state) from the second mode "mode 2" (waiting for irradiation state) in which radiation irradiation can be detected.

After the console C determines that the radiation image capturing in the selected image capturing room R is finished, the console C changes the status of usage of the image capturing room R stored in the storage unit 107e to "vacant" from "in use". Thereby, the image capturing room R is switched to the image capturing room R which is selectable from the image capturing room which cannot be selected.

Next, the operation of the radiation image capturing system 200 according to the embodiment will be described with reference to the flowchart of FIGS. 21 to 23.

Figure 21:
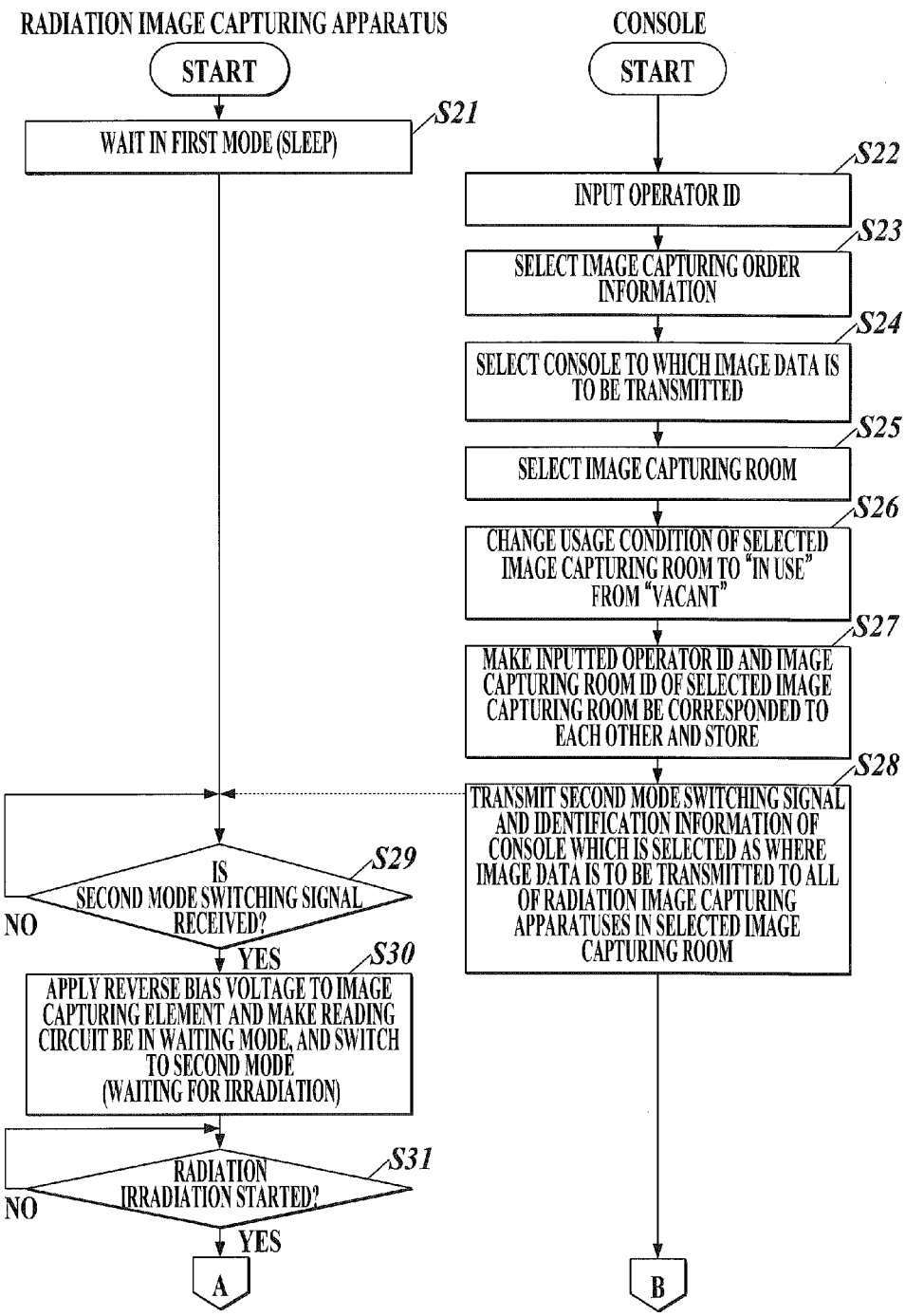
FIG. 21 This is the first diagram of a flowchart showing an example of a process procedure in the radiation image capturing system according to the third embodiment.

First, the radiation image capturing apparatus 1 in the image capturing room R which is not in use is disposed in the image capturing room R in a state where the power consumption mode thereof is in the first mode "mode 1" (sleep state) (step S21 of FIG. 21).

Before the radiation image capturing, an operator who carries out the radiation image capturing inputs the operator ID which is assigned to her/him in advance by the input unit 107*c* or the like of the console C (step S22 of FIG. 21).

Next, the console control unit 107*a* of the console C reads out and obtains image capturing order information stored in the storage unit 107*e* (or obtains image capturing order information from HIS/RIS via a network) and displays in the selecting screen H1 of the display unit 107*d*, for example, as shown in FIG. 19.

In the embodiment, the image capturing order information display column h11 for displaying the list of the image capturing order information stored in the storage unit 107*e* is provided in the selecting screen H1. Further, on the left side of the image capturing order information display column h11, selecting buttons h12 for selecting the image capturing order information to set the radiation image capturing of this time are provided so as to respectively correspond with the image capturing order information. Further, an OK button h13 and a return button h14 are provided below the image capturing order information display column h11.

On the selecting screen H1, an operator uses the input unit 107*c* to click the selecting button h12 which corresponds with the image capturing order information of the radiation image capturing of this time and clicks the OK button h13 to select the image capturing order information (step S23 of FIG. 21).

Next, the console control unit 107*a* of the console C displays the selecting screen (not shown in the drawing) for selecting the console C as the destination for the image data in the display unit 107*d*. In the selecting screen, an operator selects the console C as the destination of the image data transmitted from the radiation image capturing apparatus 1 among the consoles C1 to C3 which are selectable (step S24 of FIG. 21).

Here, in the default setting for selecting the destination of the image data, the console C by which the selecting of image capturing order information and image capturing room R is carried out is to be selected as the console as the destination for the image data. Therefore, unless an operator selects a different console C as the destination of the image, the console C by which the selecting of image capturing order information and image capturing room R is carried out is automatically selected as the destination of the image data.

Next, the console control unit 107*a* of the console C displays the selecting screen H2 for selecting the image capturing room R in which the image capturing is to be carried out in the display unit 107*d* as shown in FIG. 24.

In the embodiment, the image capturing room display column h15 for displaying the image capturing rooms R1 to R4 is provided in the selecting screen H2.

Further, on the left side of the image capturing room display column h15, the selecting buttons h16 for selecting the image capturing room R which can be selected for the radiation image capturing of this time are provided by respectively being corresponded with the selectable image capturing rooms R. The selecting buttons h16 are provided so as to be corresponded only with the selectable image capturing rooms R1, R3 and R4 which are indicated as "vacant" in the storage unit 107*e*, and the image capturing room R2 which cannot be selected which is indicated as "in use" in the storage unit 107*e* cannot be selected. Furthermore, in the section of the image capturing room R2 which is in used in the image capturing room display column h15, an indication showing that the image capturing room R2 is "in use" is displayed. Thereby, an operator can recognize the vacant image capturing rooms R1, R3 and R4 in which the radiation image capturing is not carried out and the image capturing room R2 in use in which the radiation image capturing is carried out by looking at the selecting screen H2 of FIG. 24.

Moreover, on the right side of the image capturing room display column h15, the radiation image capturing apparatus display column h17 for displaying information relating to the radiation image capturing apparatuses 1 in the image capturing rooms R is provided. For example, as shown in FIG. 24, the cassette IDs of the radiation image capturing apparatuses 1A to 1N in the image capturing rooms R are displayed in the radiation image capturing apparatus display column h17 and for example, an operator can recognize that five radiation image capturing apparatuses 1A to 1E to which the cassette IDs "1001" to "1005" are respectively assigned are disposed in the image capturing room R. In such way, an operator can select the image capturing room R which is to be used for the image capturing by recognizing the radiation image capturing apparatuses 1 which are in each of the image capturing rooms R.

Here, the information relating to each of the radiation image capturing apparatuses 1 in the image capturing room R to be displayed in the selecting screen H2 is not limited to the cassette ID and for example, the information may be information such as the type information of scintillator, size information, resolution level or the like of each of the radiation image capturing apparatuses.

Further, the OK button h18 and the return button h19 are provided below the image capturing order information display column h11.

On the selecting screen H2, an operator clicks the selecting button h16 which corresponds with the image capturing order information of the radiation image capturing of this time and clicks the OK button h18 to select the image capturing room R to be used for the radiation image capturing of this time (step S25 of FIG. 21).

Then, in the status of usage of the image capturing rooms R stored in the storage unit 107*e*, the console control unit 107*a* of the console C changes the status of usage of the selected image capturing room R to "in use" from "vacant" (step s26 of FIG. 21). Thereby, the image capturing room R1 cannot be selected as the image capturing room R to be used for image capturing until the image capturing is finished.

Further, the console control unit 107*a* of the console C makes the image capturing room ID which is assigned to the selected image capturing room R in advance correspond with the operator ID inputted by an operator in the process of step S22 to store in the storage unit 107*e* (step S27 of FIG. 21).

Hereinafter, a case where an operator selects the image capturing room R1 as the image capturing room R to be used for the image capturing among four image capturing rooms R1 to R4, for example, will be described so that the process carried out in the image capturing room R which is selected as the image capturing room R to be used for the image capturing can be discriminated from the process carried out in other image capturing rooms R. Further, a case where an operator selects the console C1 as the console C which is the destination of image data among three consoles C1 to C3, for example, will be described so that the process carried out in the console C which is selected as the destination of image data can be discriminated from the process carried out in other consoles C.

Next, the console control unit 107a transmits the second mode switching signal which instructs to switch to the second mode "mode 2" (waiting for irradiation state) to all of the radiation image capturing apparatuses 1A to 1E in the selected image capturing room R1 along with the identification information of the console C1 which is selected as the destination of image data via the communication unit 107b and the wireless access point 103 (step S28 of FIG. 21). Further, the console C transmits the image capturing order information which is selected in the selecting screen H1 by an operator to the operation table 105 which is disposed in the front room Ra of the selected image capturing room R1 via a cable or the like.

On the other hand, the control unit 22 of each of the radiation image capturing apparatuses 1A to 1E disposed in the elected image capturing room R1 determines whether the second mode switching signal is received from the console C or not (step S29 of FIG. 21). When the control unit 22 of each of the radiation image capturing apparatuses 1A to 1E determines that the second mode switching signal is received (step S29 of FIG. 21; Yes), the control unit 22 applies the reverse bias voltage to the image capturing elements 7 and controls the mode switching switch to be in the ON state and switches the reading circuits 17 to the waiting mode in which power is not supplied to switch the power consumption mode thereof to the second mode "mode 2" (waiting for irradiation state) from the first mode "mode 1" (sleep state) (step S30 of FIG. 21).

Here, the second mode switching signal which is transmitted from the console C is received by all of the radiation image capturing apparatuses 1A to 1E in the image capturing room R1 which is selected as the image capturing room R in which image capturing is to be carried out. Therefore, all of the radiation image capturing apparatuses 1A to 1E in the image capturing room R1 which is selected are to be switched to the second mode "mode 2" (waiting for irradiation state) from the first mode "mode 1" (sleep state) by the instruction from the console C.

Furthermore, the console C carries out a so-called dark reading process of performing a reading without radiation irradiation to each of the radiation image capturing apparatuses 1A to 1E disposed in the selected image capturing room R1 to obtain a dark reading value. The dark reading value obtained by the dark reading process is used as an off set correcting value to carry out an off set correction in the after-mentioned image correction process.

Here, the timing of executing the dark reading process is not limited to before the image capturing, and the configuration may be such that the dark reading process is to be executed at the timing of after the image capturing.

Further, the configuration may be such that the dark reading process (the off set correcting process) is to be carried out at the radiation image capturing apparatus 1 side.

Next, the control unit 22 of each of the radiation image capturing apparatuses 1A to 1E in the selected image capturing room R1 determines whether the radiation irradiation is started or not by determining whether the voltage value V outputted from the electric current detection unit 42 exceeded the threshold value Vth or not (step S31 of FIG. 21).

When an operator finishes the operation of selecting the image capturing order information, the image capturing room R1 in which the image capturing is to be carried out and the console C1 as the destination of image data in the above described console C, an operator moves into the image capturing room R1 from the console C and executes the radiation image capturing by using the radiation image capturing apparatus 1 which he/she desires to use among the five radiation image capturing apparatuses 1A to 1E which are disposed in the image capturing room R1 by being in the second mode "mode 2" (waiting for irradiation state). In particular, an operator operates the switch 106 of the operation table 105 disposed in the front room Ra of the image capturing room R2 to activate the radiation generation device 102 and irradiates the radiation from the radiation generation device 102 to the desired radiation image capturing apparatus 1.

At this time, an operator may execute the radiation image capturing by using any radiation image capturing apparatus 1 among the five radiation image capturing apparatuses 1A to 1E in the selected image capturing room R1, being in the second mode "mode 2" (waiting for irradiation state). That is, an operator may select the radiation image capturing apparatus 1 to be used for the image capturing at the timing when actually carrying out the radiation image capturing in the selected image capturing room R1 to carry out the radiation image capturing.

Further, an operator does not need to carry out any operations or work to select the radiation image capturing apparatus 1 to be used for the image capturing as the radiation image capturing apparatus 1 to be used for the image capturing, and an operator simply carries out the radiation image capturing by irradiating the radiation from the radiation generation device 102 to the radiation image capturing apparatus 1 used for the image capturing.

Hereinafter, in order to describe the process which is carried out in the radiation image capturing apparatus 1 to be used in image capturing and the process which is carried out in the radiation image capturing apparatuses 1 which are not used for image capturing by discriminating the one process from the other, a case where an operator executes an image capturing by using the radiation image capturing apparatus 1E among the five radiation image capturing apparatuses 1A to 1E in the image capturing room R1 will be described as an example.

The control unit 22 of each of the radiation image capturing apparatuses 1A to 1D which do not detect radiation irradiation by not being used for the image capturing determines that the radiation irradiation does not start (step S31 of FIG. 21; No) and repeats the process of step S31.

On the other hand, when the control unit 22 of the radiation image capturing apparatus 1E which detects the radiation irradiation by being used for the image capturing detects that the voltage outputted from the electric current detection unit 42 due to the radiation irradiation exceeded the threshold value Vth and determines that the radiation irradiation is started (step S31 of FIG. 21; Yes), the control unit 22 of the radiation image capturing apparatus 1E makes the mode switching switch 24 be in the OFF state and supplies power to the reading circuits 17 and switches the power consumption mode of itself to the third mode "mode 3" (electric charge accumulating state) from the second mode "mode 2" (waiting for irradiation state) by switching the reading circuits 17 to the power supply mode (step S32 of FIG. 22).

That is, among the five radiation image capturing apparatuses 1A to 1E in the selected image capturing room R1, only the radiation image capturing apparatus 1E which is actually used for the image capturing is automatically switched to the third mode "mode 3" (electric charge accumulating state) by receiving the radiation irradiation. On the other hand, the other radiation image capturing apparatuses 1A to 1D which are not used for the image capturing are to be maintained in the second mode "mode 2" (waiting for irradiation state).

Figure 22:
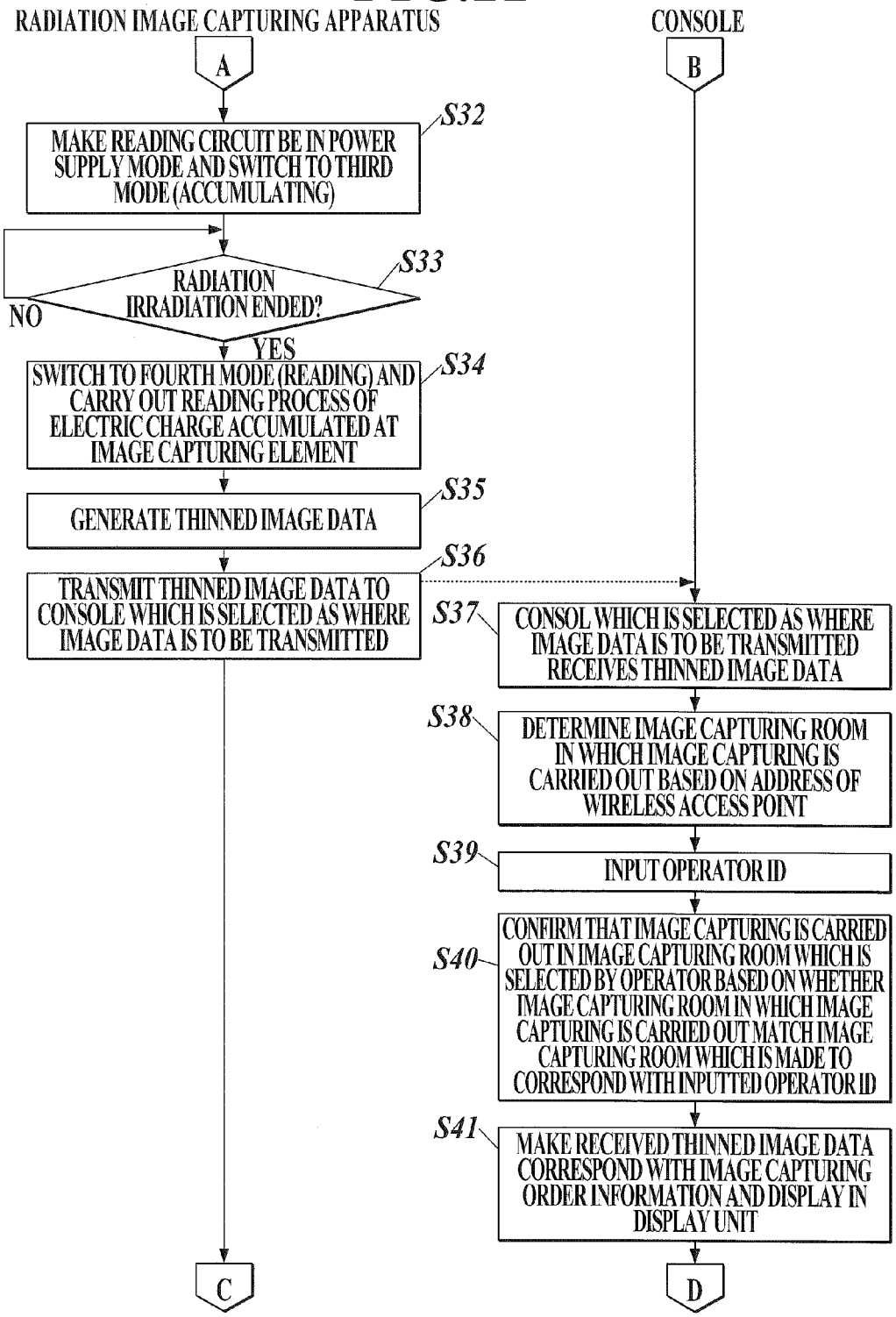
FIG. 22 This is the second diagram of the flowchart showing an example of the process procedure in the radiation image capturing system according to the third embodiment.

Next, the control unit 22 of the radiation image capturing apparatus 1E which is used for the image capturing and which detected the radiation irradiation determines whether the radiation irradiation is ended or not by determining whether the voltage value V outputted from the electric current detection unit 42 is equal to or smaller than the threshold value Vth or not (step S33 of FIG. 22). Then, when the control unit 22 of the radiation image capturing apparatus 1E determines that the radiation irradiation is ended due to the voltage value V outputted from the electric current detection unit 42 being equal to or smaller than the threshold value Vth by the radiation irradiation from the radiation generation device 102 is ended (step S33 of FIG. 22; Yes), the control unit 22 of the radiation image capturing apparatus 1E makes the scan activation circuit 15 apply the ON voltage for signal reading to each of the scanning lines 5 to make the TFT 8 connected to each of the scanning line 5 be in the ON state and switches the power consumption mode of itself to the fourth mode "mode 4" (reading state) from the third mode "mode 3" (electric charge accumulating state). Thereafter, the control unit 22 of the radiation image capturing apparatus 1E executes the reading process of converting the electric charges accumulated in the image capturing elements 7 by the radiation irradiation into electric signals and stores the data obtained from the reading process to the storage unit 23 (step S34 of FIG. 22).

Moreover, the control unit 22 of the radiation image capturing apparatus 1E which detected the radiation irradiation carries out various types of image correction processes such as the off set/gain correction, the defect correction and the like to the data obtained by the reading process as needed to generate image data (raw data) and stores the generated image data (raw data) in the storage unit 22, and generates thinned image data from the generated image data (step S35 of FIG. 22). Then, the control unit 22 of the radiation image capturing apparatus 1E makes to generated thinned image data correspond with the cassette ID "1005" which is assigned to itself to transmit to the console C1 as the destination of the image data via the antenna device 39 and the wireless access point 103 (step S36 of FIG. 22).

The console C receives the thinned data which is transmitted from the radiation image capturing apparatus 1E which is used for the image capturing and which detected the radiation irradiation via the wireless access point 103 and the communication unit 107b (step S37 of FIG. 22).

Next, the console control unit 107a of the console C1 determines the wireless access point 103 which the image data went through based on the address of the wireless access point 103 which is attaches as the head information of the image data and determines in which image capturing room R the image capturing is carried out (step S28 of FIG. 22).

Next, the operator who finished the radiation image capturing in the image capturing room R1 returns to the console C1 which is assigned as the destination of the image data from the image capturing room R1 and inputs the operator ID which is assigned to her/him by the input unit 107c (step S39 of FIG. 22).

When the operator ID is inputted by the input unit 107c, the console control unit 107a of the console C1 reads out the image capturing room ID of the image capturing room R which is made to correspond with the operator ID which is inputted and confirms that the image capturing was carried out in the image capturing room R1 which is selected by the operator based on whether the image capturing room ID of the image capturing room R1 (that is, the image capturing room R1 which is selected as the image capturing room R to be used for the image capturing) which is read out and the image capturing room ID of the image capturing room R in which the image capturing is actually carried out match each other or not (step S40 of FIG. 22). Here, when the image capturing room ID of the image capturing room R1 which is made to correspond with the operator ID which is inputted and the image capturing room ID of the image capturing room R in which the image capturing is actually carried out do not match each other, it is determined that the image capturing was carried out in an wrong image capturing room R and this fill be notified to the operator in the display unit 107d.

Next, the console control unit 107a of the console C1 as the destination of image data makes the thinned image data which is received from the image capturing room R1 in which the operator carried out image capturing, that is, the thinned image data which is received from the radiation image capturing apparatus 1E which the operator used for the image capturing and which detected the radiation irradiation correspond with the image capturing order information which is selected and inputted by the input unit 107c to display in the display unit 107d (step S41 of FIG. 22).

The operator confirms whether the image capturing needs to be carried out again or not, whether the image data is made to correspond with the correct image capturing order information or not and the like by looking at the image data displayed in the display unit 107d of the console C1 as the destination of image data. When the image data is not to be carried out again, the operator uses the input unit 107c to carry out the operation to instruct the transmission of the original image data (raw data) of the thinned image data (step S42 of FIG. 23).

Here, when the console control unit 107a of the console C1 receives a plurality of thinned image data from the same image capturing room R1, the console control unit 107a groups the image data which are received from the same image capturing room R1 to display them in the display unit 107d. Thereby, when displaying a plurality of thinned image data which are received from the same image capturing room R1 in the display unit 107d, an operator such as a technologist or the like corrects the correspondence relation between each of the thinned image data displayed in the display unit 107d and the image capturing order information and pushes the OK button or the like (not shown in the drawing) to suitably correct and store the correspondence relation between each of the thinned image data and the image capturing order information.

Figure 23:
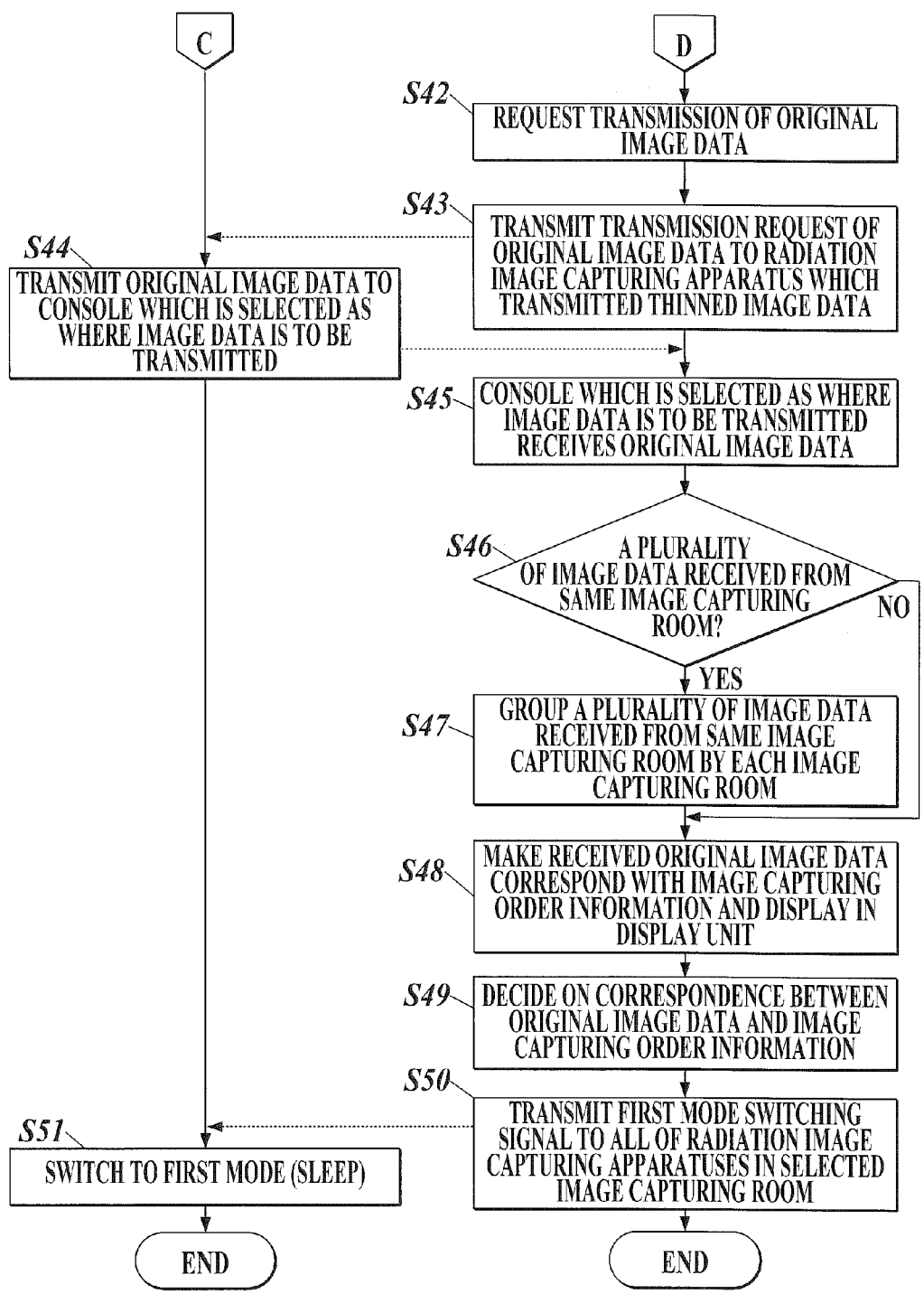
FIG. 23 This is the third diagram of a flowchart showing an example of the process procedure in the radiation image capturing system according to the third embodiment.

When the transmission of the original image data (raw data) of the thinned image data is instructed by the input unit 107c, the console control unit 107a of the console C which is selected as the destination of the image data transmits the instruction signal for requesting the transmission of the original image data (raw data) to the radiation image capturing apparatus 1E (that is, the radiation image capturing apparatus 1E which was used for the image capturing and which detected the radiation irradiation) which transmitted the thinned image data via the communication unit 107b and the wireless access point 103 (step S43 of FIG. 23).

When the radiation image capturing apparatus 1E (that is, the radiation image capturing apparatus 1E which was used for the image capturing and which detected the radiation irradiation) which transmitted the thinned image data receives the instruction signal requesting the transmission of the original image data (raw data), the radiation image capturing apparatus 1E reads out the original image data (raw data) which is stored in the storage unit 23 and transmits the original image data to the console C1 which is the destination of the image data via the antenna device 39 and the wireless access point 103 (step S44 of FIG. 23).

On the other hand, when the console control unit 107a of the console C1 which is the destination of the image data receives the original image data (raw data) which is transmitted from the radiation image capturing apparatus 1E (step S45 of FIG. 23), the radiation image capturing apparatus 1E determines whether a plurality of original image data (raw data) are received from the same image capturing room R or not (step S46 of FIG. 23). Then, when the radiation image capturing apparatus 1E determines that a plurality of original image data (raw data) are received from the same image capturing room R (step S46 of FIG. 23; Yes), the radiation image capturing apparatus 1E makes the plurality of original image data (raw data) correspond with the image capturing room ID of the image capturing room R to group the original image data (raw data) in the image capturing room R units (step S47 of FIG. 23).

Here, a process similar to the above grouping process of the original image data (raw data) in the image capturing room R units is also carried out when the thinned image data are obtained.

Further, the console control unit 107a of the console C1 displays the image based on the received original image data (raw data) in the display unit 107d along with the image capturing order information (step S48 of FIG. 23). At this time, when there are plurality of image data which are received from the same image capturing room R, the console control unit 107a groups those image data to be displayed in the same screen.

Furthermore, when an operator who looked as the image in the display unit 107d carries out the operation of deciding on the correspondence between the received original image data and the image capturing order information by the input unit 107c (step S49 of FIG. 23), the console control unit 107a decides on the correspondence between the received original image data (raw data) and the image capturing order information and makes the image capturing room ID of the image capturing room R in which the image capturing was carried out correspond with the decided correspondence to store the original image data (raw data) in the storage unit 107e in the units of image capturing room R.

When the correspondence between the original image data and the image capturing order information is decided on, the console control unit 107a determines that the image capturing in the image capturing room R1 is finished and transmits the first mode switching signal which instructs to switch the power consumption mode to the first mode "mode 1" (sleep mode) to all of the radiation image capturing apparatuses 1A to 1E in the image capturing room R1 via the communication unit 107b and the wireless access point 103 (step S50 of FIG. 23).

When the radiation image capturing apparatuses 1A to 1E which are disposed in the image capturing room R1 receive the first mode switching signal from the console C, the power consumption mode thereof is switched to the first mode "mode 1" (sleep state) from the second mode "mode 2" (waiting for irradiation state) (step S51 of FIG. 23) and the process is ended.

Then, the first mode switching signal which is transmitted from the console C1 which is selected as the destination of image data is to be received by all of the radiation image capturing apparatuses 1A to 1E disposed in the image capturing room R1. Thereby, the power consumption mode of all of the radiation image capturing apparatuses 1A to 1E in the image capturing room R1 which is used for the image capturing is switched to the first mode "mode 1" (sleep state) from the second mode "mode 2" (waiting for irradiation state). Further, the image capturing room R1 is switched to the vacant state and the series of the process ends.

As described above, according to the radiation image capturing system 200 according to the embodiment, the console C switches the power consumption mode of all of the radiation image capturing apparatuses 1A to 1E in the selected image capturing room R1 to the second mode "mode 2" (waiting for irradiation state) in which starting of radiation irradiation can be detected at the timing when the image capturing room R1 in which the image capturing is to be carried out is selected by the input unit 107c. Then, when the control unit 22 of the one radiation image capturing apparatus 1E which is to be used for the image capturing among the radiation image capturing apparatuses 1A to 1E disposed in the selected image capturing room R1 detects the radiation irradiation by monitoring the current amount of the electric current that flows in the bias lines 9 detected by the electric current detection unit 42, the control unit 22 of the radiation image capturing apparatus 1E switches the power consumption mode thereof to the third mode "mode 3" (electric charge accumulating state) in which the reading circuits 17 are made to be in the power supply mode. Furthermore, the radiation image capturing apparatus 1E which is switched to the third mode "mode 3" (electric charge accumulating state) generates image data by reading out the electric charges accumulated in the image capturing elements 7 due to the radiation irradiation and transmits the image data to the console 107.

That is, only by an operator carrying out the operation of selecting the image capturing room, the image data is to be transmitted to the console C from the radiation image capturing apparatus 1 which is actually used for the image capturing, even when the radiation image capturing apparatus 1 to be used for the image capturing is not selected before the image capturing.

Therefore, in the radiation image capturing system 200 of the embodiment, an operator does not need to use the radiation image capturing apparatuses 1 by consciously identifying each of the radiation image capturing apparatuses 1, and further, an operator does not need to carry out any operations and works for selecting the radiation image capturing apparatus 1 to be used for the image capturing.

That is, an operator does not need to carry out an operation to identify the cassette ID of the radiation image capturing apparatus 1 which is to be used for the image capturing to search for the radiation image capturing apparatus 1 to which the cassette ID is attached among the plurality of radiation image capturing apparatuses 1. Further, an operator does not need to carry out an operation or a work to switch the power consumption mode of the radiation image capturing apparatus 1 which is used for the image capturing to the mode capable of carrying out the image capturing.

In such way, an operator can decide the radiation image capturing apparatus 1 to be used for the image capturing according to the condition and the like of a patient at the timing when actually carrying out the radiation image capturing and the radiation image capturing can be carried out by using the radiation image capturing apparatus 1 which an operator decided on.

Moreover, even when a case where the radiation image capturing apparatus 1 other than the radiation image capturing apparatus 1 which was planned to be used needs to be used occurs at the timing when carrying out the radiation image capturing, an operator does not need to carry out any operation for executing the image capturing by using another radiation image capturing apparatus 1.

Furthermore, when carrying out the radiation image capturing, an operator does not need to be conscious about which radiation image capturing apparatus 1 is the radiation image capturing apparatus 1 which he/she is using.

Further, an operator only selects the image capturing room R in the console C. Other than that, an operator does not need to carry out any operation such as operating of the switch or taking out the radiation image capturing apparatus 1 from a cradle in the image capturing room R1, and an operator simply needs to execute the radiation image capturing by using the desired radiation image capturing apparatus 1.

Moreover, the image data obtained by the console C are made to correspond with the selected image capturing room R and stored by the image capturing room R units. Therefore, even when any of the image capturing room R is selected among the plurality of image capturing rooms R, an operator such as a technologist can extract only the image data which he/she is handled the image capturing thereof by inputting the number of the image capturing room R which was used for the image capturing room or the like in the console C. Further, even when the system is configured so as to share the console C between a plurality of operators such as technologists and between a plurality of image capturing rooms R, mixing up of image data can be prevented and image data can be made to respectively correspond with image capturing information correctly.

As described above, in the radiation image capturing system 1 of the embodiment, the burden of an operator with regards to operations is very small, and the radiation image capturing system 1 of the embodiment is very convenient for an operator.

Moreover, the image data is transmitted to the console C from the radiation image capturing apparatus 1 which is actually used for the image capturing. Therefore, even when an operator mistakenly uses the radiation image capturing apparatus 1 (when uses the radiation image capturing apparatus 1 different from the radiation image capturing apparatus 1 which was planned to be used for the image capturing in advance), the console C can obtain the correct image data from the radiation image capturing apparatus 1 which is actually used for the image capturing.

That is, for example, when an operator executes the radiation image capturing by mistakenly using the radiation image capturing apparatus 1E to which the cassette ID "1005" is assigned thinking that he/she is using the radiation image capturing apparatus 1D to which the cassette ID "1004" is assigned, the image data is to be transmitted to the console 107 from the radiation image capturing apparatus 1E having the cassette ID "1005" which is actually used for the image capturing. Therefore, the correct image data can be obtained even when the radiation image capturing apparatuses 1 are confused.

Moreover, because the reading circuit 7 is maintained to be in the waiting mode in which the power consumption is small until radiation is irradiated to the radiation image capturing apparatus 1, the time period for the reading circuit 17 be in the power supply mode in which the power consumption is larger comparing to that in the waiting mode can be prevented from becoming unnecessarily long. Therefore, the power consumption at the time of radiation image capturing can be reduced and wasting of unneeded power can be inhibited.

Further, because the image capturing order information inputted by the input unit 107c is made to correspond with the image data which is transmitted from the radiation image capturing which is actually used for the image capturing in the console C which is selected as the destination of the image data, the convenience of the system is improved.

Furthermore, because the radiation image capturing apparatus 1 which was used for the image capturing and which detected the radiation irradiation generates the thinned image data and transmits the generated thinned image data to the console C, the operator can confirm the image in the console C in an early stage and can determined whether the image capturing needs to be carried out again or not.

Moreover, because an operator can select the image capturing room R to be used for the image capturing from the plurality of image capturing rooms R, the operator can carry out the image capturing in the desired image capturing room R. Therefore, the system can be a user friendly system for the operator.

When selecting the image capturing room R to be used for the image capturing, the cassette IDs of the radiation image capturing apparatus 1 in each of the image capturing rooms R are displayed in the display unit 107d in the image capturing room R units. Therefore, an operator can select the image capturing room R to be used for the image capturing after recognizing which radiation image capturing apparatuses 1 are disposed in each of the image capturing rooms R.

Moreover, when a plurality of consoles C are provided in the radiation image capturing system of the embodiment and are shared among the plurality of image capturing rooms R, a console C can be selected as the destination of image data to which the image data is to be transmitted from the radiation image capturing apparatus 1 among the plurality of consoles C. Therefore, an operator can confirm the image data in the desired console C and the system can be a user friendly system for the operator.

Further, when both of the console C of default setting and the console C which is newly selected as the console C which is the destination of image data receive a plurality of image data which are transmitted from the plurality of radiation image capturing apparatuses 1 in the same image capturing room R, because the plurality of image data which are received are grouped by image capturing room units, an operator can recognize the plurality of image data obtained by the image capturing together in the console C even when a plurality of times of image capturing are carried out by using a plurality of radiation image capturing apparatuses 1 in one image capturing room R.

Here, in the above embodiment, the case of the configuration where the power consumption mode of the radiation image capturing apparatuses 1 in the image capturing room R which is selected as the image capturing room R to be used for the image capturing is switched to the first mode "mode 1" (sleep state) from the second mode "mode 2" (waiting for irradiation state) according to the first mode switching signal which is transmitted from the console C after the correspondence between the image data (raw data) which is original of the thinned image data transmitted from the radiation image capturing apparatus 1 in the image capturing room R and the image capturing order information is decided on is described. However, the timing of switching the power consumption mode of the radiation image capturing apparatuses 1 which do not detect the radiation irradiation to the first mode "mode 1" (sleep state) is not limited to the above timing.

For example, the configuration may be such that when the radiation image capturing apparatus 1 does not detect radiation irradiation within a predetermined time period after the power consumption mode is switched to the second mode "mode 2" (waiting for irradiation state) from the first mode "mode 1" (sleep state) according to the second mode switching signal transmitted from the console 107, the power consumption mode thereof is automatically switched to the first mode "mode 1" (sleep state) from the second mode "mode 2" (waiting for irradiation state) by the control unit 22. By having the configuration as described above, there is no need to send and receive a signal or the like for switching the power consumption mode of the radiation image capturing apparatus 1 to the first mode "mode 1" (sleep state) between the console 107 and the radiation image capturing apparatus 1, and the control configuration can be simplified.

Moreover, the configuration may be such that when the radiation image capturing is to be carried out in one image capturing room R for only one time, the console C switches all of the radiation image capturing apparatuses 1 other than the radiation image capturing apparatus 1 which is used for the image capturing to the first node "mode 1" (sleep mode) from the second mode "mode 2" (waiting for irradiation state) after the console C receives the thinned image data from the radiation image capturing apparatus 1 which is used for the image capturing. Whether a plurality of times of radiation image capturing are to be carried out or not can be determined based on the number of image capturing order information inputted before the image capturing, for example.

Further, the configuration may be such that when the radiation image capturing is to be carried out in one image capturing room R for only one time, the radiation image capturing apparatus 1 which detected the radiation irradiation further informs the console C of that the radiation irradiation is detected along with the cassette ID of itself right after when the radiation irradiation is detected, and the console C which received the notification transmits the first mode switching signal which instructs to switch to the first mode to the radiation image capturing apparatuses 1 other than the radiation image apparatus 1 which detected the radiation irradiation to switch the power consumption mode of the radiation image capturing apparatuses 1 which does not detect the radiation irradiation to the first mode "mode 1" (sleep state) from the second mode "mode 2" (waiting for irradiation state). By having such configuration, the power consumption mode of the radiation image capturing apparatus 1 which is to be used for the image capturing can be switched to the first mode "mode 1" (sleep state) in an even earlier stage and the power consumption can be reduced even more.

As described above, because the radiation image capturing apparatuses 1 which are to be used for the image capturing are switched to the first mode "mode 1" in which power consumption is even smaller than in the second mode "mode 2" by the control of the console C, the power consumption can be reduced even more.

That is, in a case where the radiation image capturing apparatus 1 which is switched to the second mode "mode 2" by the control of the console C does not detect radiation irradiation for more than a predetermined time period, unnecessary power consumption in the radiation image capturing apparatus 1 which is not to be used for the image capturing increases when the time interval for switching to the first mode "mode 1" from the second mode "mode 2" is set sufficiently long in the system where the apparatus is switched to the first mode voluntarily. On the other hand, when the time interval for switching to the first mode "mode 1" from the second mode "mode 2" is set to be short, there is a possibility that all of the radiation image capturing apparatuses 1 are already switched to the first mode "mode 1" at the time of actually carrying out the radiation image capturing when the time period from when the apparatus is switched to the second mode "mode 2" to the execution of the radiation image capturing is long.

Comparing to the above cases, when it is configured that the radiation image capturing apparatus 1 which is not to be used for the image capturing is switched to the first mode "mode 1" from the second mode "mode 2" by the control of the console C as in the radiation image capturing system 200 of the embodiment, the radiation image capturing apparatus 1 which is not to be used for the image capturing can be switched to the first mode "mode 1" at more appropriate timing.

Further, the configuration may be such that the control unit 22 of the radiation image capturing apparatus 1 which is used for the image capturing and which detects the radiation irradiation switches the power consumption mode of the apparatus to the first mode "mode 1" (sleep state) after transmitting the original image data (raw data) to the console C.

Moreover, in the above embodiment, the configuration where the radiation image capturing apparatus 1 which detected the radiation irradiation transmits the thinned image data to the console 107 prior to the image data which is the original of the thinned image data is described. However, the configuration may be such that the thinned image data is not generated and only the image data (raw data) is to be transmitted.

Furthermore, in the above embodiment, the case where the image data is transmitted to the console C from the radiation image capturing apparatus 1 when an operator requests the transmission of the image data by the input unit 107c of the console C is described. However, the configuration may be such that by providing an image transmission switch for instruction the image data transmission to the radiation image capturing apparatus 1, the image data is transmitted to the console C when the image transmission switch is operated by an operator.

Here, in the second embodiment and the third embodiment, the configuration may be such that the radiation irradiation is detected by detecting the electric current that flows in the apparatus due to the radiation irradiation by detecting the electric current that flows in the scanning line and the signal lines, by detecting the electric current that flows between the power circuit 15a and the gate driver 15b of the scan activation circuit 15 by the electric current detection unit 42\* (see FIG. 12) or the like as described in the first embodiment instead of detection radiation irradiation by monitoring the current amount of the electric current that flows in the bias lines 9 detected by the electric current detection unit 42 in the radiation image capturing apparatus 1.

Here, it is needless to say that the present invention is not limited to the above described embodiments and modifications and that the present invention can be changed arbitrarily.

INDUSTRIAL APPLICABILITY

The present invention can be applied in the field (especially in the medical field) of carrying out radiation image capturing.

EXPLANATION OF REFERENCE NUMERALS 1 radiation image capturing apparatus (portable radiation image capturing apparatus)
1A~1E A plurality of radiation image capturing apparatuses (a plurality of portable radiation image capturing apparatus)
5 scanning line
6 signal line
7 image capturing element
9 bias line
14 reverse bias power source
15 scan activation circuit
15$a$ power circuit
15$b$ gate driver
17 reading circuit
18$a$ operational amplifier
18$a$1 inverting input terminal
18$a$2 non-inverting input terminal
18$a$3 output terminal
18$c$ switch for resetting electric charge
22 control unit
39 antenna device (communication unit)
40 battery
42, 42* electric current detection unit
100, 200 radiation image capturing system
102 radiation generation device
107, C console
107$c$ input unit
C1~C3 a plurality of consoles
mode 1 first mode
mode 2 second mode
mode 3 third mode
R image capturing room
r area
R1~R4 a plurality of image capturing rooms
V voltage value corresponding to current amount of electric current In the claims:

1. A radiation image capturing system comprising:
a radiation generation device which emits radiation and which is disposed in an image capturing room;
a portable radiation image capturing apparatus which includes a plurality of image capturing elements each of which generates an electric charge according to an amount of radiation irradiation from the radiation generation device and which generates image data based on the electric charges read from the image capturing elements; and
a console which is made to correspond with the image capturing room in advance and which communicates with the portable radiation image capturing apparatus in the image capturing room,
wherein
the radiation image capturing system includes a plurality of portable radiation image capturing apparatuses structured to detect starting of radiation irradiation by the radiation generation device, the plurality of portable radiation image capturing apparatuses being included in the image capturing room, and
the portable radiation image capturing apparatus is structured such that, when at least one of the plurality of portable radiation image capturing apparatuses in the image capturing room detects that the radiation irradiation by the radiation generation device started, the portable radiation image capturing apparatus generates image data based on the electric charges read from the image capturing elements and transmits the generated image data to the console which corresponds with the image capturing room.

2. The radiation image capturing system of claim 1, wherein
each portable radiation image capturing apparatus has a first power consumption mode and a second power consumption mode in which starting of the radiation irradiation is detectable;
the first power consumption mode has a power consumption lower than that of the second power consumption mode, and
the console includes an input unit for inputting predetermined information and the console switches power consumption modes of all of the portable radiation image capturing apparatuses in the image capturing room to the second power consumption mode from the first power consumption mode in response to the input of the predetermined information by the input unit.

3. The radiation image capturing system of claim 1, wherein
the image capturing room is one of a plurality of image capturing rooms;
each portable radiation image capturing apparatus has a first power consumption mode and a second power consumption mode in which starting of the radiation irradiation is detectable;
the first power consumption mode has a power consumption lower than that of the second power consumption mode, and
the console comprises a selecting unit structured to select an image capturing room of the plurality of image capturing rooms to be used for image capturing and the console switches power consumption modes of all of the portable radiation image capturing apparatuses in the image capturing room which is selected by the selecting unit to the second power consumption mode from the first power consumption mode in response to the selecting of the image capturing room which is to be used for the image capturing.

* * * * *